(12) United States Patent
Palecek et al.

(10) Patent No.: US 11,591,569 B2
(45) Date of Patent: Feb. 28, 2023

(54) METHODS FOR EPICARDIAL DIFFERENTIATION OF HUMAN PLURIPOTENT STEM CELLS

(71) Applicant: Wisconsin Alumni Research Foundation, Madison, WI (US)

(72) Inventors: Sean P. Palecek, Verona, WI (US);
Xiaoping Bao, Madison, WI (US);
Xiaojun Lian, Solna (SE)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/156,677

(22) Filed: Oct. 10, 2018

(65) Prior Publication Data

US 2019/0085293 A1 Mar. 21, 2019

Related U.S. Application Data

(62) Division of application No. 15/091,239, filed on Apr. 5, 2016, now Pat. No. 10,131,878.

(60) Provisional application No. 62/143,359, filed on Apr. 6, 2015.

(51) Int. Cl.
*C12N 5/077* (2010.01)
*A61K 35/34* (2015.01)

(52) U.S. Cl.
CPC ............ *C12N 5/0657* (2013.01); *A61K 35/34* (2013.01); *C12N 2500/38* (2013.01); *C12N 2500/95* (2013.01); *C12N 2501/15* (2013.01); *C12N 2501/415* (2013.01); *C12N 2501/727* (2013.01); *C12N 2501/998* (2013.01); *C12N 2501/999* (2013.01); *C12N 2506/02* (2013.01); *C12N 2533/54* (2013.01)

(58) Field of Classification Search
CPC .............. C12N 5/0657; C12N 2500/95; C12N 2501/999; C12N 2501/15; A61K 35/34
See application file for complete search history.

(56) References Cited

U.S. PATENT DOCUMENTS

2013/0189785 A1 7/2013 Palecek et al.

FOREIGN PATENT DOCUMENTS

WO WO2015035506 A1 * 3/2015 ............. C12N 5/077
WO WO2015042356 A1 * 3/2015 ........... C12N 5/0735

OTHER PUBLICATIONS

Asli et al. Epicardial Origin of Resident Mesenchymal Stem Cells in the Adult Mammalian Heart. J. Dev. Biol. 2014, 2, 117-137 (Year: 2014).*
Le et al. Cardiac progenitor cells for heart repair. Cell Death Discovery (2016) 2, 16052, p. 1-4 (Year: 2016).*
Witty, et al., Generation of the epicardial lineage from human pluripotent stem cells. Nat. Biotechnol. 32, 1026-1035 (2014).
Xiao, et al., SB-431542 inhibition of scar formation after filtration surgery and its potential mechanism. Invest. Ophthalmol. Vis. Sci. 50, 1698-706 (2009).
Yu, et al., Induced Pluripotent Stem Cell Lines Derived from Human Somatic Cells, Science 318:1917-1920 (2007).
Yu, et al., Human Induced Pluripotent Stem Cells Free of Vector and Transgene Sequences, Science 324 (5928):797-801 (2009).
Zhou, et al., Epicardial epithelial to mesenchymal transition in injured heart. J. Cell. Mol. Med. 15, 2781-2783 (2011).
Zhou, et al., Adult mouse epicardium modulates myocardial injury by secreting paracrine factors. J. Clin. Invest. 121, 1894-1904 (2011).
Zhou, et al., Epicardial progenitors contribute to the cardiomyocyte lineage in the developing heart. Nature 454, 109-13 (2008).
Zhou, et al., Nkx2-5- and Isl1-expressing cardiac progenitors contribute to proepicardium. Biochem. Biophys. Res. Commun. 375, 450-3 (2008).
Ashton, et al., Progress and prospects for stem cell engineering. Annu. Rev. Chem. Biomol. Eng. 2, 479-502 (2011).
Bao, et al., Chemically-defined albumin-free differentiation of human pluripotent stem cells to endothelial progenitor cells. Stem Cell Res. 15, 122-129 (2015).
Bochmann, et al., Revealing new mouse epicardial cell markers through transcriptomics. PLoS One 5, e11429 (2010).
Brade, et al., Embryonic heart progenitors and cardiogenesis. Cold Spring Harb. Perspect. Med. 3, a013847 (2013).
Cao, et al., Ascorbic acid enhances the cardiac differentiation of induced pluripotent stem cells through promoting the proliferation of cardiac progenitor cells. Cell Res. 22, 219-36 (2012).
Cheung, et al., Generation of human vascular smooth muscle subtypes provides insight into embryological origin-dependent disease susceptibility. Nature Biotechnology 30, 165-173 (2012).
David, et al., MesP1 drives vertebrate cardiovascular differentiation through Dkk-1-mediated blockade of Wnt-signalling. Nat. Cell Biol. 10, 338-45 (2008).
Dye, et al., In vitro generation of human pluripotent stem cell derived lung organoids. Elife 4, e05098 (2015).
Engels, et al., Insulin-like growth factor promotes cardiac lineage induction in vitro by selective expansion of early mesoderm. Stem Cells 32, 1493-502 (2014).
Garriock, et al., Isolation and culture of mouse proepicardium using serum-free conditions. Methods 66, 365-9 (2014).
Hockemeyer, et al., Genetic engineering of human pluripotent cells using TALE nucleases. Nat. Biotechnol. 29, 731-4 (2011).
Iyer, et al., Robust derivation of epicardium and its differentiated smooth muscle cell progeny from human pluripotent stem cells. Development 142, 1528-1541 (2015).

(Continued)

*Primary Examiner* — Taeyoon Kim
(74) *Attorney, Agent, or Firm* — McDonnell Boehnen Hulbert & Berghoff, LLP

(57) ABSTRACT

Methods for generating high-yield, high-purity epicardial cells are described. Wnt/β-catenin signaling is first activated in human cardiac progenitor cells, by, for example, inhibiting Gsk-3 to induce differentiation into epicardial cells. Methods for long-term in vitro maintenance of human cardiac progenitor cell-derived epicardial cells and method comprising chemically defined, xeno-free, and albumin-free culture conditions are also provided.

5 Claims, 24 Drawing Sheets

Specification includes a Sequence Listing.

(56) References Cited

OTHER PUBLICATIONS

Kattman, et al., Stage-specific optimization of activin/nodal and BMP signaling promotes cardiac differentiation of mouse and human pluripotent stem cell lines. Cell Stem Cell 8, 228-40 (2011).

Kikuchi, et al., Retinoic Acid Production by Endocardium and Epicardium is an Injury Response Essential for Zebrafish Heart Regeneration. Dev. Cell 20, 397-104 (2011).

Kim, et al., HISAT: a fast spliced aligner with low memory requirements. Nat. Methods 12, 357-360 (2015).

Kofidis, et al., Insulin-like growth factor promotes engraftment, differentiation, and functional improvement after transfer of embryonic stem cells for myocardial restoration. Stem Cells 22, 1239-45 (2004).

Lam, et al., Multipotent progenitor cells in regenerative cardiovascular medicine. Pediatr. Cardiol. 30, 690-8 (2009).

Lepilina, et al., A Dynamic Epicardial Injury Response Supports Progenitor Cell Activity during Zebrafish Heart Regeneration. Cell 127, 607-619 (2006).

Lian, et al., A small molecule inhibitor of SRC family kinases promotes simple epithelial differentiation of human pluripotent stem cells. PLoS One 8, e60016 (2013).

Lian, et al., Chemically defined, albumin-free human cardiomyocyte generation. Nat. Methods 12, 595-596 (2015).

Lian, et al., Directed cardiomyocyte differentiation from human pluripotent stem cells by modulating Wnt/β-catenin signaling under fully defined conditions. Nat. Protoc. 8, 162-75 (2013).

Lian, et al., Efficient Differentiation of Human Pluripotent Stem Cells to Endothelial Progenitors via Small-Molecule Activation of WNT Signaling. Stem Cell Reports 3, 804-16 (2014).

Lian, et al., Robust cardiomyocyte differentiation from human pluripotent stem cells via temporal modulation of canonical Wnt signaling. Proc. Natl. Acad. Sci. U. S. A. 109, E1848-E1857 (2012).

Männer, et al., Development and Function of the Epicardium. Advances in Developmental Biology 18, 333-357 (2007).

Martínez-Estrada, et al., Wt1 is required for cardiovascular progenitor cell formation through transcriptional control of Snail and E-cadherin. Nat. Genet. 42, 89-93 (2010).

Minami, et al., A small molecule that promotes cardiac differentiation of human pluripotent stem cells under defined, cytokine- and xeno-free conditions. Cell Rep. 2, 1448-60 (2012).

Moore, et al., YAC complementation shows a requirement for Wt1 in the development of epicardium, adrenal gland and throughout nephrogenesis. Development 126, 1845-57 (1999).

Murry, et al., Differentiation of embryonic stem cells to clinically relevant populations: lessons from embryonic development. Cell 132, 661-80 (2008).

Nakanishi, et al., Directed induction of anterior and posterior primitive streak by Wnt from embryonic stem cells cultured in a chemically defined serum-free medium. FASEB J. 23, 114-22 (2009).

Palpant, et al., Inhibition of β-catenin signaling respecifies anterior-like endothelium into beating human cardiomyocytes. Development 142, 3198-209 (2015).

Pérez-Pomares, et al., Experimental studies on the spatiotemporal expression of WT 1 and RALDH2 in the embryonic avian heart: a model for the regulation of myocardial and valvuloseptal development by epicardially derived cells (EPDCs). Dev. Biol. 247, 307-26 (2002).

Pérez-Pomares, et al., Origin of coronary endothelial cells from epicardial mesothelium in avian embryos. Int. J. Dev. Biol. 46, 1005-13 (2002).

Phillips, et al., Dkk1 and Dkk2 regulate epicardial specification during mouse heart development. Int. J. Cardiol. 150, 186-92 (2011).

Prasain, et al., Differentiation of human pluripotent stem cells to cells similar to cord-blood endothelial colony-forming cells. Nat. Biotechnol. 32, 1151-7 (2014).

Ramsköld, et al., An abundance of ubiquitously expressed genes revealed by tissue transcriptome sequence data. PLoS Comput. Biol. 5, e1000598 (2009).

Riley, P. R. An Epicardial Floor Plan for Building and Rebuilding the Mammalian Heart. Curr. Top. Dev. Biol. 100, 233-251 (2012).

Ruiz-Villalba, et al., Characterization of epicardial-derived cardiac interstitial cells: differentiation and mobilization of heart fibroblast progenitors. PLoS One 8, e53694 (2013).

Sahara, et al., Manipulation of a VEGF-Notch signaling circuit drives formation of functional vascular endothelial progenitors from human pluripotent stem cells. Cell Res. 24, 820-41 (2014).

Samuel, et al., Generation of functionally competent and durable engineered blood vessels from human induced pluripotent stem cells. Proc. Natl. Acad. Sci. U. S. A. 110, 12774 9 (2013).

Schmuck, et al., Cardiac fibroblast-derived 3D extracellular matrix seeded with mesenchymal stem cells as a novel device to transfer cells to the ischemic myocardium. Cardiovasc. Eng. Technol. 5, 119-131 (2014).

Smart, et al., Thymosin beta4 induces adult epicardial progenitor mobilization and neovascularization. Nature 445, 177-82 (2007).

Subramanian, et al., Gene set enrichment analysis: a knowledge-based approach for interpreting genome-wide expression profiles. Proc. Natl. Acad. Sci. U. S. A. 102, 15545-50 (2005).

Tadeu, et al., Transcriptional profiling of ectoderm specification to keratinocyte fate in human embryonic stem cells. PLoS One 10, e0122493 (2015).

Thomson, et al., Embryonic Stem Cell Lines Derived from Human Blastocysts. Science 282, 1145-1147 (1998).

Ueno, et al., Biphasic role for Wnt/beta-catenin signaling in cardiac specification in zebrafish and embryonic stem cells. Proc. Natl. Acad. Sci. U. S. A. 104, 9685-90 (2007).

Van Tuyn, et al., Epicardial cells of human adults can undergo an epithelial-to-mesenchymal transition and obtain characteristics of smooth muscle cells in vitro. Stem Cells 25, 271-278 (2007).

Wang, et al., Derivation of Smooth Muscle Cells with Neural Crest Origin from Human Induced Pluripotent Stem Cells. Cells Tissues Organs 195, 5-14 (2012).

Wang, et al., Epicardial regeneration is guided by cardiac outflow tract and Hedgehog signalling. Nature 522, 226-230 (2015).

Wang, et al., Engineering vascular tissue with functional smooth muscle cells derived from human iPS cells and nanofibrous scaffolds. Biomaterials 35, 8960-8969 (2014).

Winter, et al., Preservation of left ventricular function and attenuation of remodeling after transplantation of human epicardium-derived cells into the infarcted mouse heart. Circulation 116, 917-27 (2007).

Bax et al. "In vitro epithelial-to-mesenchymal transformation in human adult epicardial cells is regulated by TGFb-signaling and WT1," Basic Res Cardiol 106(5):829-47 (Sep. 2011).

Baba et al., "Constitutively active beta-catenin confers multilineage differentiation potential on lymphoid and myeloid progenitors," Immunity 23(6):599-609 (Dec. 2005).

Chen et al., "Chemically defined conditions for human iPSC derivation and culture," Nat. Methods 8(5):424-9 (May 2011).

Ebert et al., "Induced pluripotent stem cells from a spinal muscular atrophy patient," Nature 457(7227):277-80 (Jan. 2009).

Gurney et al., "Wnt pathway inhibition via the targeting of Frizzled receptors results in decreased growth and tumorigenicity of human tumors," Proc. Natl. Acad. Sci. USA, 109(29): 11717-22 (Jul. 2012).

Hagen et al., "Expression and characterization of GSK-3 mutants and their effect on beta-catenin phosphorylation in intact cells," J Biol Chem, 277(26):23330-35 (Jun. 2002).

He et al., "A monoclonal antibody against Wnt-1 induces apoptosis in human cancer cells," Neoplasia 6(1):7-14 (Jan.-Feb. 2004).

Howden et al., "Genetic correction and analysis of induced pluripotent stem cells from a patient with gyrate atrophy," Proc. Natl. Acad. Sci. U. S. A. 108(16):6537-42 (Apr. 2011).

GenBank Accession No. X87838, "H.sapiens mRNA for beta-catenin," Oct. 7, 2008 [retrieved from the internet https://www.ncbi.nlm.nih.gov/nuccore/X87838] [retrieved on Nov. 23, 2020] (3 pages).

(56) References Cited

OTHER PUBLICATIONS

GenBank Accession No. CAA61107.1, "beta-catenin [*Homo sapiens*]," Oct. 7, 2008 [retrieved from the internet https://www.ncbi.nlm.nih.gov/protein/CAA61107.1] [retrieved on Nov. 23, 2020] (3 pages).

Formulation of Advanced D-MEM/F-12 Media, ThermoFisher Scientific, accessed from www.thermofisher.com/us/en/home/technical-resources/media-formulation.227.html (last accessed Mar. 25, 2022) [3 pages].

Formulation of RPMI 1640 Media, ThermoFisher Scientific, accessed from www.thermofisher.com/us/en/home/technical-resources/media-formulation.114.html (last accessed Mar. 25, 2022) [2 pages].

* cited by examiner

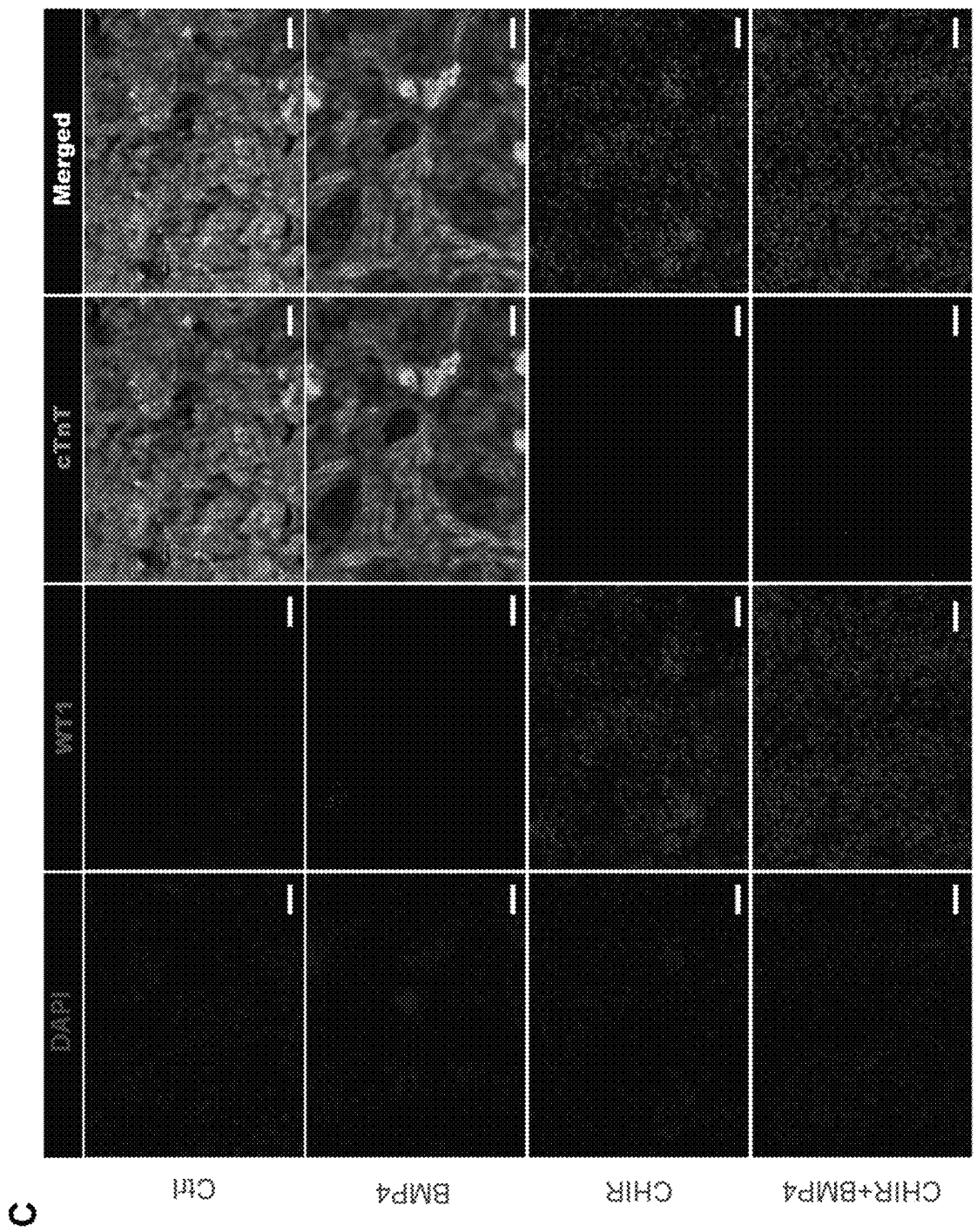
FIGS. 1A-1C, CONTINUED

FIGS. 2A-2E, CONTINUED
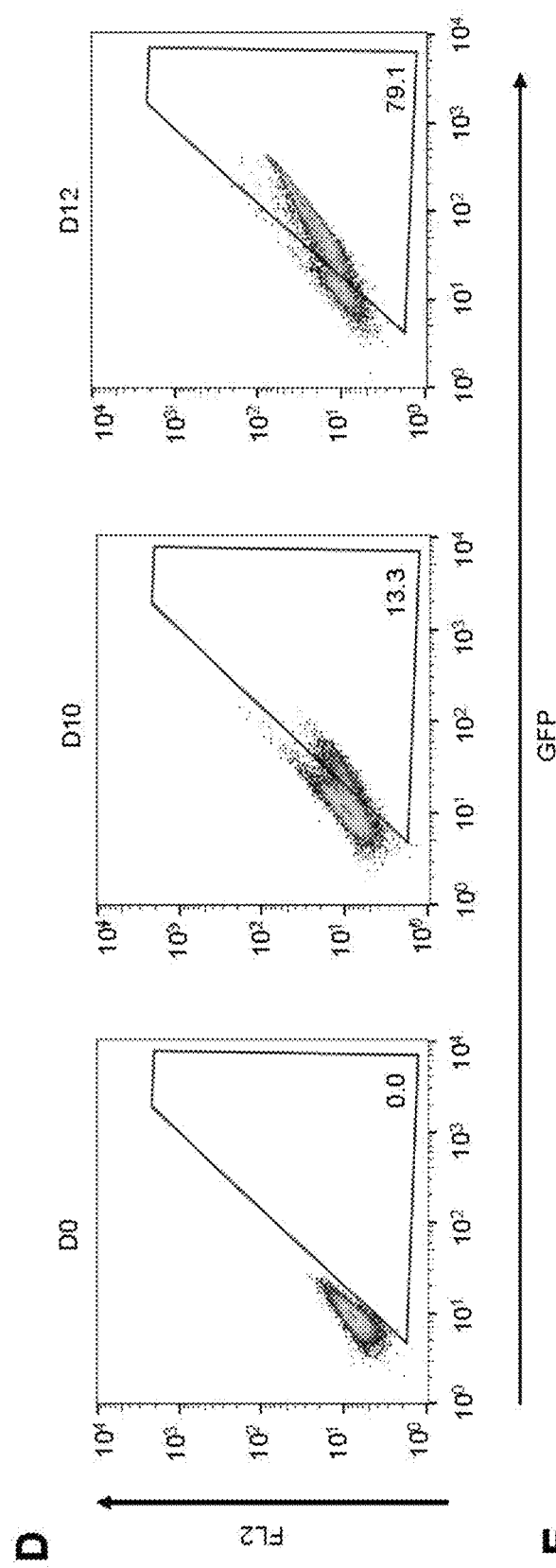
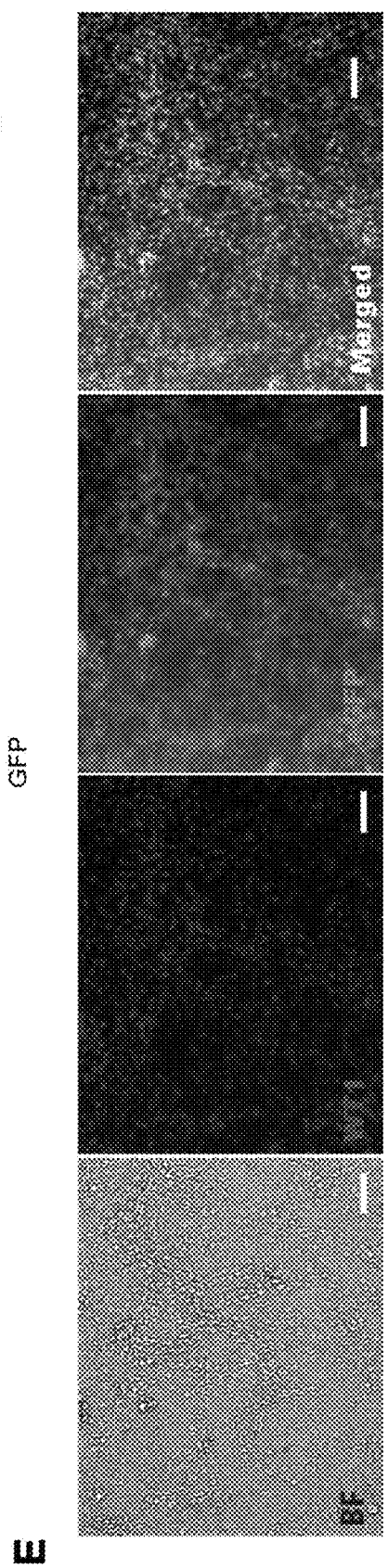

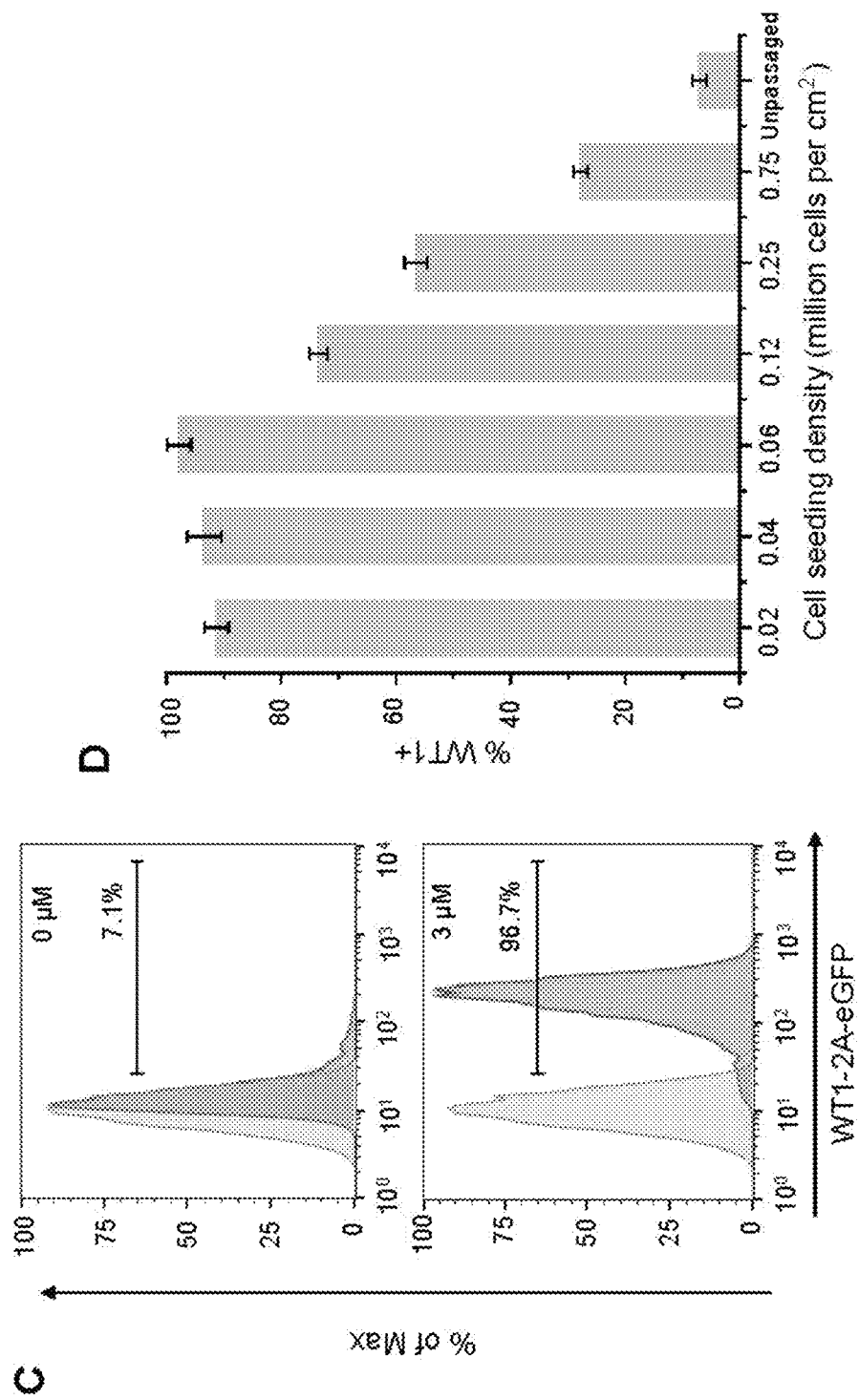
FIGS. 3A-3E, CONTINUED

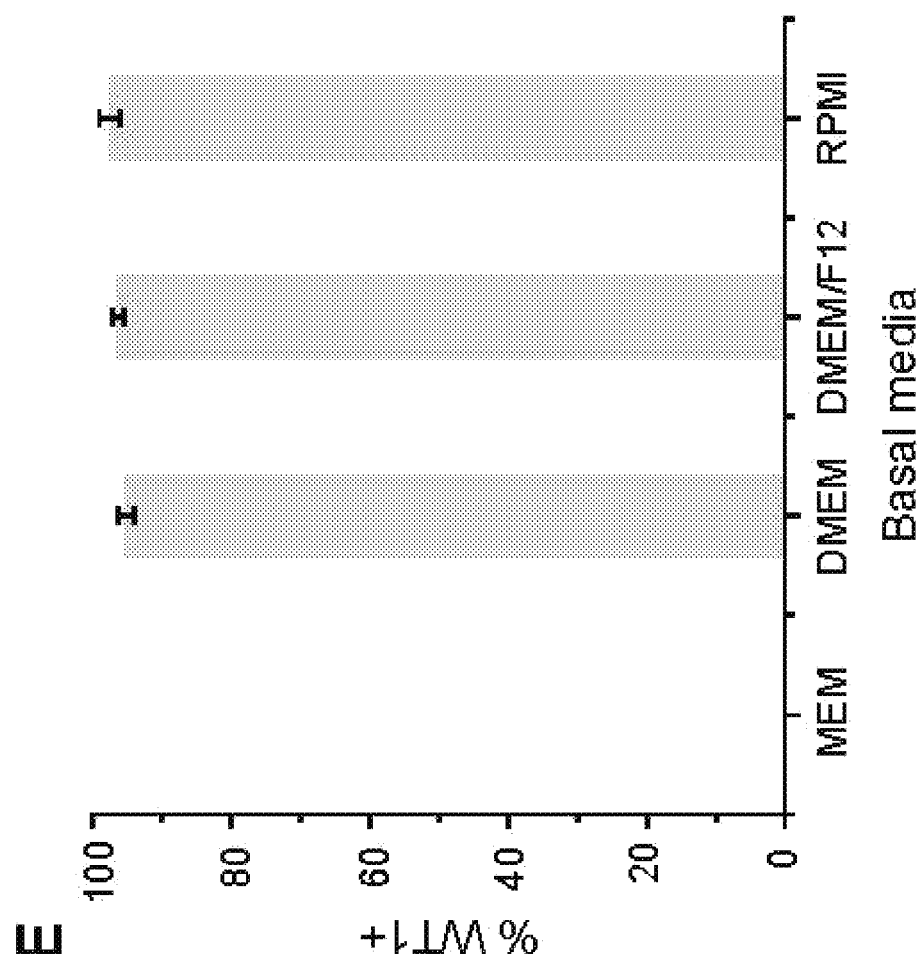
FIGS. 3A-3E, CONTINUED

FIG. 5A-5E
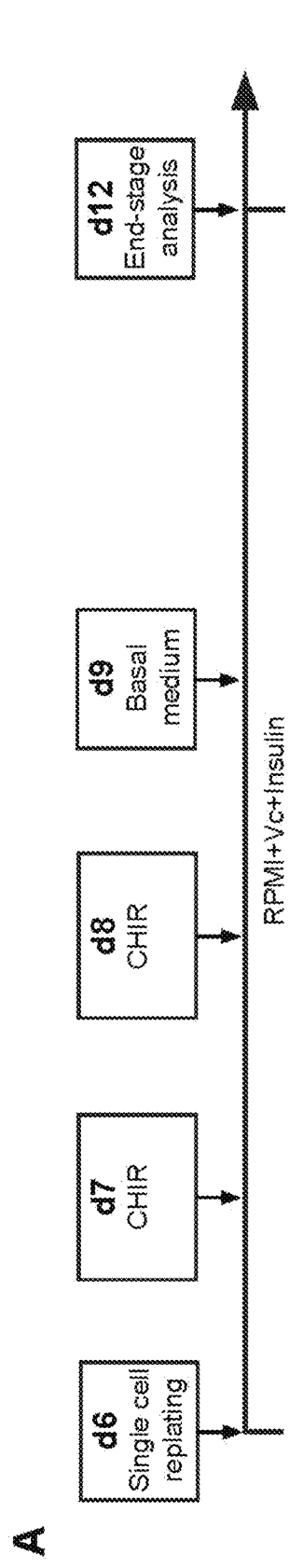
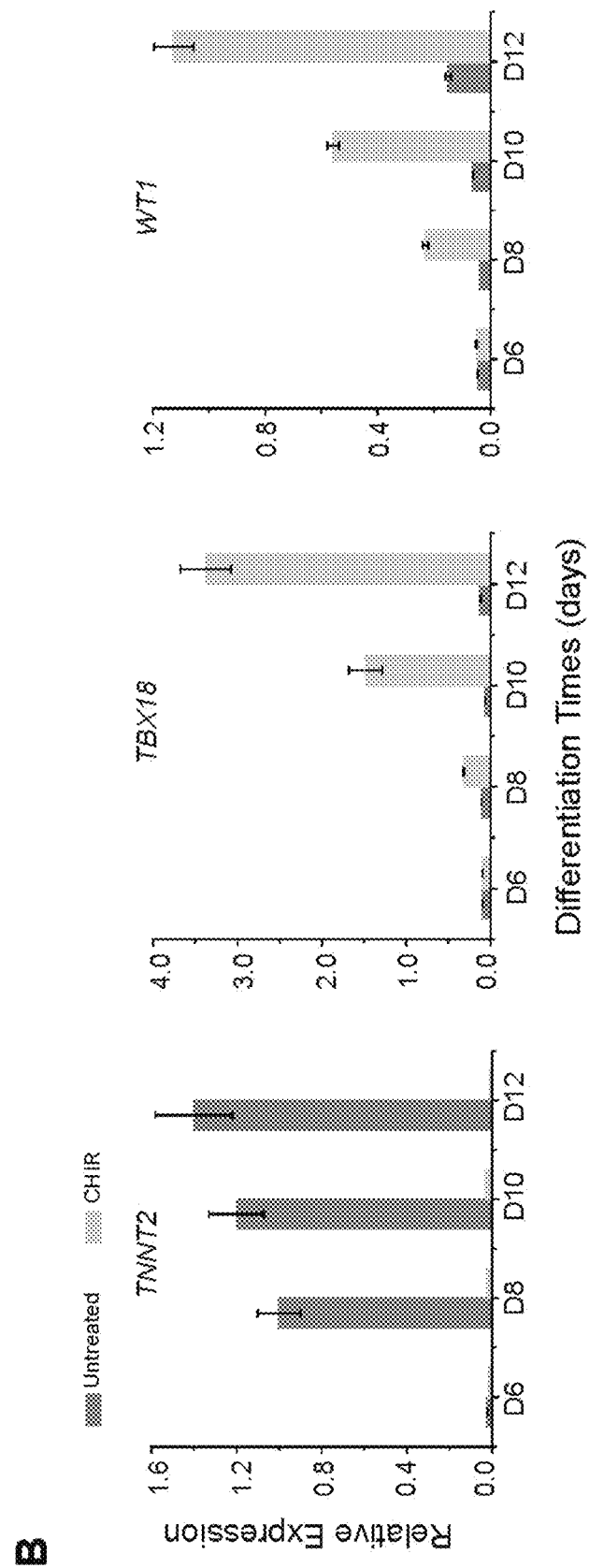

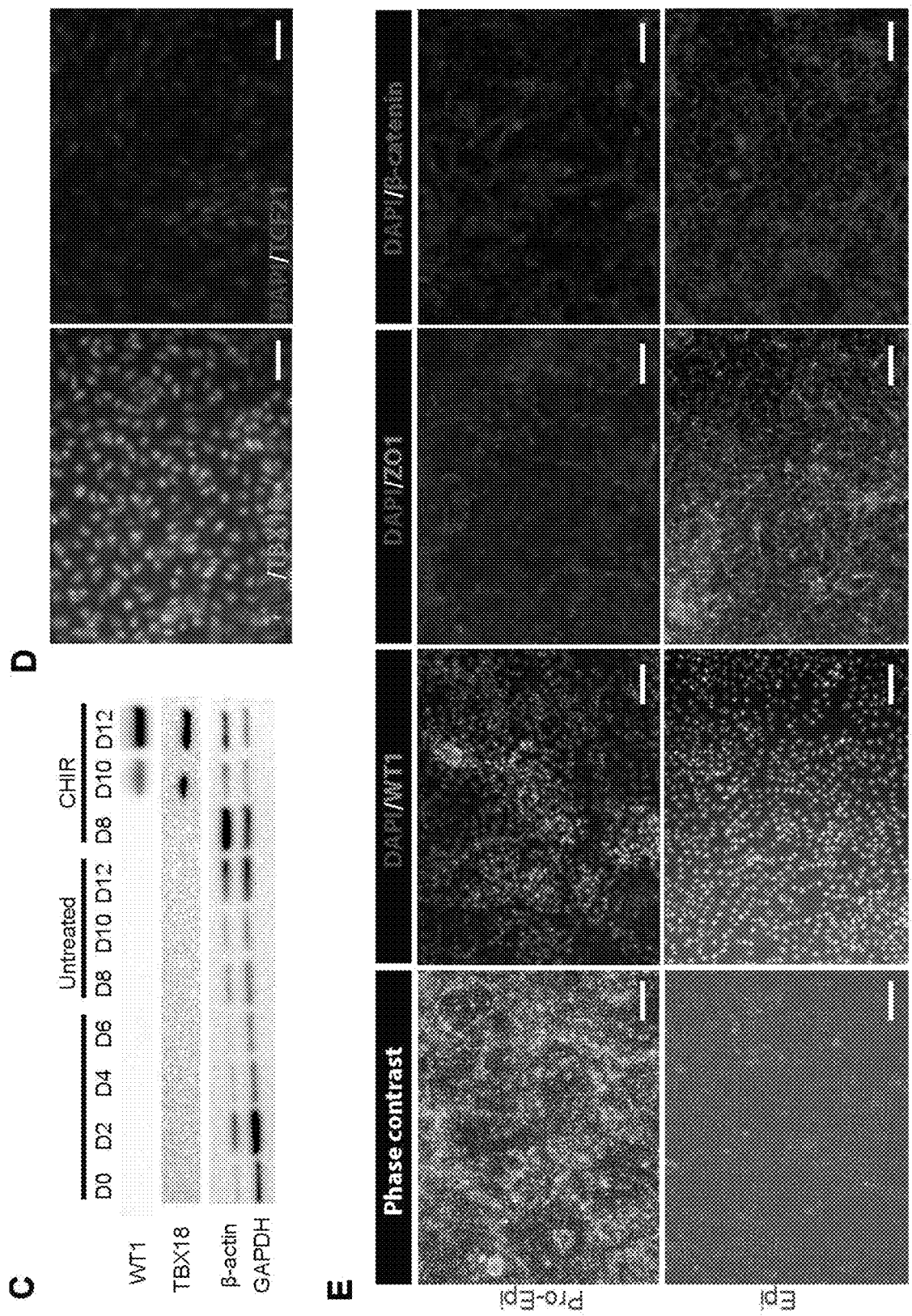
FIG. 5A-5E, CONTINUED

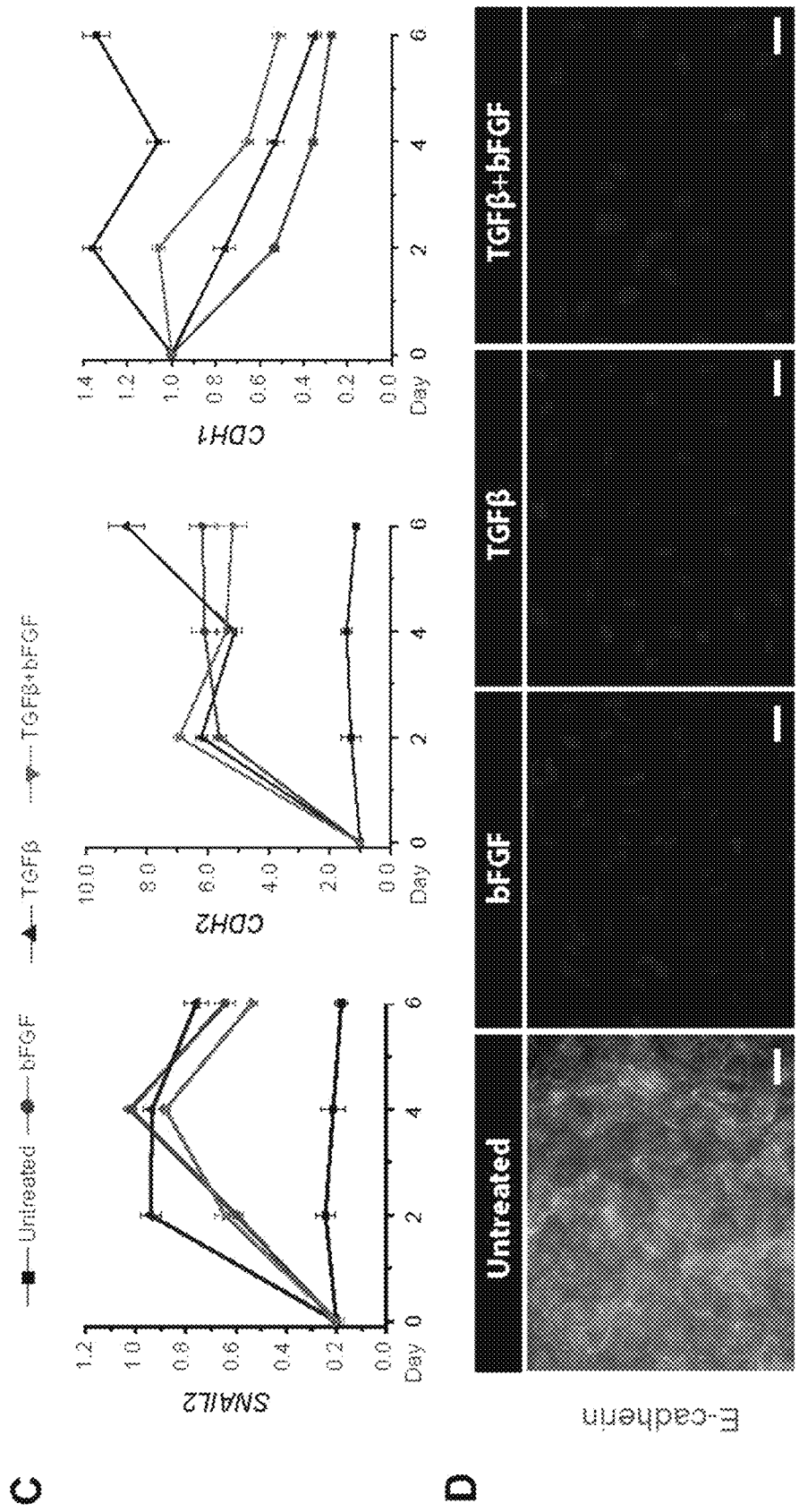
FIGS. 6A-6D, CONTINUED

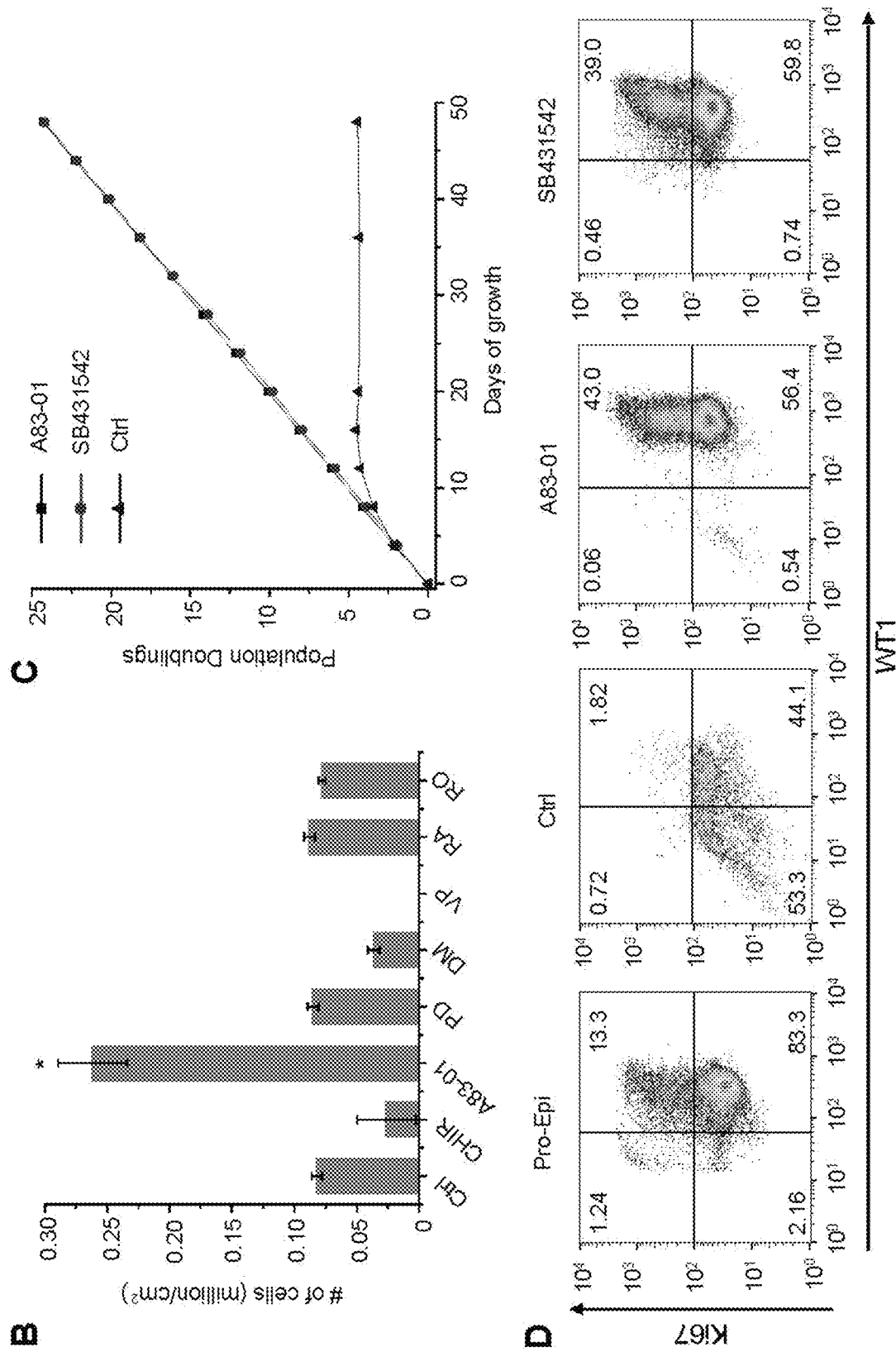
FIGS. 7A-7D, CONTINUED

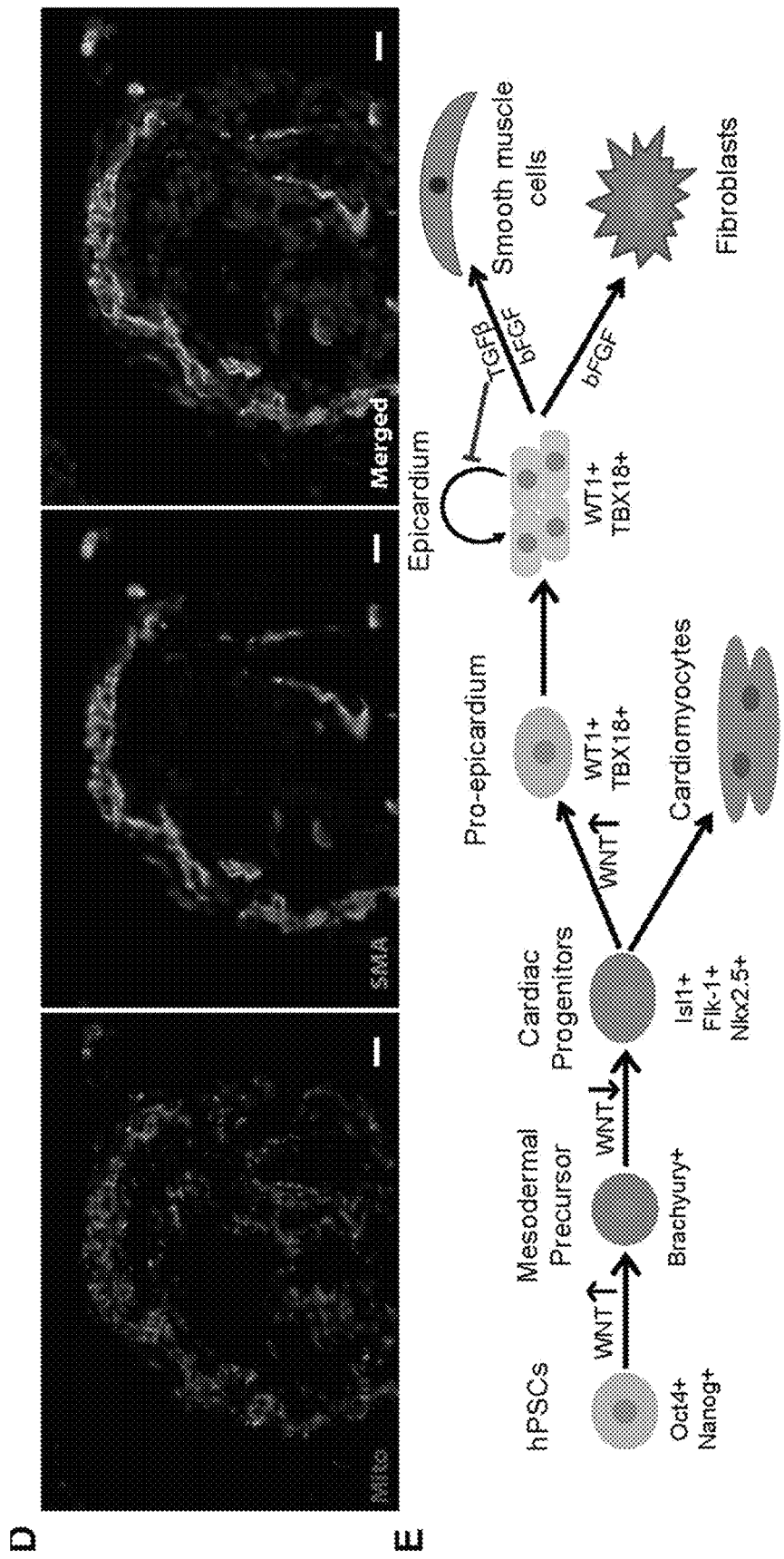
FIGS. 8A-8E, CONTINUED

METHODS FOR EPICARDIAL DIFFERENTIATION OF HUMAN PLURIPOTENT STEM CELLS

CROSS-REFERENCE TO RELATED APPLICATIONS

This application is a divisional application of U.S. patent application Ser. No. 15/091,239, filed Apr. 5, 2016, which claims priority to U.S. Provisional Patent Application No. 62/143,359, filed Apr. 6, 2015, which is incorporated herein by reference as if set forth in its entirety.

STATEMENT REGARDING FEDERALLY SPONSORED RESEARCH OR DEVELOPMENT

This invention was made with government support under EB007534 awarded by the National Institutes of Health. The government has certain rights in the invention.

BACKGROUND

The mammalian heart, the first functional organ in the developing vertebrate embryo, includes three distinct structures—the epicardium, myocardium, and endocardium. The epicardium, the outermost layer of the heart, contributes both multi-lineage descendants and important trophic signals to the myocardium and coronary vessels. The epicardium develops from the proepicardium, a mass of coelomic progenitors located at the venous pole of the embryonic heart. Proepicardium cells attach to and spread over the myocardium to form the primitive epicardial epithelium. During cardiogenesis, epicardial cells undergo epithelial-to-mesenchymal transition (EMT) to give rise to a population of epicardium-derived cells, which in turn invade the heart and progressively differentiate into various cell types, including cells of coronary blood vessels and cardiac interstitial cells.

The epicardium contributes both multi-lineage descendants and paracrine factors during cardiac repair, underscoring their potentials for regenerative medicine (Lepilina et al., *Cell.* 127:607-619 (2006); Kikuchi et al., *Dev. Cell.* 20:397-404 (2011); Zhou et al., *J. Clin. Invest.* 121:1894-1904 (2011); Zhou & Pu, *J. Cell. Mol. Med.* 15:2781-2783 (2012)). Understanding the molecular mechanisms that control the specification of epicardial lineages from naïve progenitor cells is fundamental to elucidating the regulatory mechanisms underlying both human heart development and cardiovascular diseases. Because of their developmental importance and therapeutic potential, epicardial cells and epicardium-derived cells present a tractable resident progenitor source to restore a functional vasculature, to maintain cardiomyocyte survival, and to repair damaged heart tissue. Accordingly, there is a need in the art for efficient and cost-effective protocols for generating functional epicardial cells under chemically defined culture conditions and in the absence of certain growth factors previously thought to be an essential part of directed epicardial differentiation.

BRIEF SUMMARY

The invention relates generally to methods for cardiac induction in human pluripotent stem cells (hPSCs) and, more particularly, to methods for generating from hPSCs populations of functional epicardial cells under chemically-defined, albumin-free conditions and for long-term maintenance of such hPSC-derived epicardial cell populations.

In one aspect, provided herein is a method for generating a population of epicardial cells from human pluripotent stem cells. Generally, the method comprises culturing human cardiac progenitor cells differentiated from human pluripotent stem cells in a chemically defined, albumin-free culture medium that comprises an activator of Wnt/β-catenin signaling, whereby a cell population comprising human epicardial cells is obtained. The human cardiac progenitor cells express one or more of Isl1, Nkx2.5, and Flk-1. In some cases, at least 95% of cells of the cell population are epicardial cells positive for expression of Wilms' tumor suppressor protein (WT1). In some cases, the chemically defined culture medium does not comprise Bone Morphogenetic Protein 4 (BMP4). The activator of Wnt/β-catenin signaling can be a Gsk3 inhibitor. The Gsk3 inhibitor can be a small molecule selected from the group consisting of CHIR99021, CHIR98014, BIO-acetoxime, BIO, LiCl, SB216763, SB415286, AR A014418, 1-Azakenpaullone, and Bis-7-indolylmaleimide. The Gsk3 inhibitor can be CHIR99021 and is present in a concentration of about 0.2 μM to about 9 μM.

The human cardiac progenitor cells can be obtained by a method comprising (i) culturing human pluripotent stem cells in a chemically defined culture medium comprising an activator of Wnt/β-catenin signaling to obtain a first cell population comprising mesodermal cells positive for expression of Brachyury/T; and (ii) culturing the first cell population in a chemically defined culture medium that comprises an inhibitor of Wnt/β-catenin signaling, whereby a cell population comprising human cardiac progenitor cells is obtained. In some cases, the human cardiac progenitor cells express one or more of Isl1, Nkx2.5, and Flk-1. The activator of Wnt/β-catenin signaling can be a Gsk3 inhibitor. The Gsk3 inhibitor can be a small molecule selected from the group consisting of CHIR99021, CHIR98014, BIO-acetoxime, BIO, LiCl, SB216763, SB415286, AR A014418, 1-Azakenpaullone, and Bis-7-indolylmaleimide. The inhibitor of Wnt/β-catenin signaling can be selected from the group consisting of a small molecule that stabilizes axin and stimulates β-catenin degradation, an inhibitor of porcupine, an antibody that blocks activation of a Wnt ligand receptor, an antibody that binds to one or more Wnt ligand family members, and a short hairpin interfering RNA (shRNA) for β-catenin in the first cell population. The small molecule that stimulates β-catenin degradation and stabilizes axin can be XAV939. The porcupine inhibitor can be selected from the group consisting of IWP2 and IWP4, or a combination thereof. The porcupine inhibitor can be present in a concentration of about 1 μM to about 4 μM. In some cases, no cell separation or selection step is used to obtain the cell population comprising epicardial cells.

In another aspect, provided herein is a method for long-term in vitro maintenance of self-renewing human epicardial cells, the method comprising culturing human cardiac progenitor cells differentiated from human pluripotent stem cells in a chemically defined, albumin-free culture medium that comprises an activator of Wnt/β-catenin signaling, whereby a cell population comprising human epicardial cells is obtained; and culturing the cell population comprising human epicardial cells in the presence of an inhibitor of TGFβ signaling, whereby the human epicardial cells are self-renewing for at least 25 population doublings, are not immortalized, and maintain the ability to undergo epithelial-to-mesenchymal transition (EMT).

In a further aspect, provided herein is a kit for differentiating human pluripotent stem cells into epicardial cells. Generally, the kit comprises (i) a culture medium suitable for differentiating human cardiac progenitor cells into epicardial cells; (ii) an agent that activates Wnt signaling in human cardiac progenitor cells; and (iii) instructions describing a method for generating human epicardial cells, the method employing the culture medium and the agent. The kit can further comprise instructions describing methods for long-term in vitro maintenance of the human epicardial cells, where the method employs a culture medium and an agent that supports long-term maintenance of such epicardial cells.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIGS. 5A-5E (FIGS. 5A-5E) present molecular analysis of hPSC-derived epicardial cells obtained under chemically-defined, albumin-free conditions. (A) Schematic of the optimized protocol for differentiation of hPSCs to epicardial cells in RPMI medium. (B-D) H13 hESC-derived cardiac progenitors were differentiated as illustrated in (A). Gene expression was assessed by quantitative RT-PCR (B). Data are represented as mean±SEM of at least three independent replicates. (C) At different time points, WT1 and TBX18 expression was assessed by western blot. (D) At day 12, immunostaining for TBX18 and TCF21 was performed. Scale bars, 50 μm. (E) Representative phase contrast microscopy and fluorescence immunostaining for WT1, ZO1, and β-catenin of day 12 pro-epicardium (Pro-Epi) and day 18 epicardium (Epi). Scale bars, 100 μm.

FIGS. 7A-7D (FIGS. 7A-7D) demonstrate long-term expansion of hPSC-derived epicardial cells. (A-B) H13 hESC-derived day 18 epicardial cells were seeded at a density of 0.05 million cells/cm² and treated with the indicated small molecules for 3 days (concentrations provided in Table 3). At day 4, representative phase contrast microscopy and fluorescence immunostaining for WT1, ZO1 and α-SMA (A), and the total cell numbers were assessed (B). Scale bars, 100 μm. (C-D) H13 hESC-derived epicardial cells were passaged and counted every four days in the absence or presence of the indicated TGFβ inhibitors: 0.5 μM A83-01 or 2 μM SB431542. The population doublings were calculated and shown in (C), and day 48 cultures were subjected to flow analysis of WT1 and Ki67 expression (D).

FIGS. 8A-8E (FIGS. 8A-8E) show that hPSC-derived epicardial cells were similar to primary epicardial cells. (A) Hierarchical clustering analysis of RNA-seq expression data of human pluripotent stem cells (hPSCs), hPSC-derived endoderm (Endo), hPSC-derived ectoderm (Ecto), hPSC-derived mesoderm (Mes), CMs, epicardial cells (Epi) derived from human stem cell lines H9, ES03, and 19-9-11, and primary epicardial cells (donor 9605, 9633, 9634, and 9635). (B) Before surgery, ES03-eGFP cells were differentiated as illustrated in FIG. 5A, cultured for 5 passages in a A83-01-containing medium, and subjected to flow cytometry analysis for WT1 and GFP expression. Histogram distribution of depth of invasion (C) of eGFP-positive cells in 2-, 6-, and 12-day sections are shown. Scale bars, 100 μm. After 12 days, hearts were harvested and representative smooth muscle actin (SMA) and human-specific mitochondria (Mito) dual stain (D) of cross-sections of the heart are shown. Arrows denote the scaffold. Scale bar, 100 μm. (E) Model highlighting the specification of hPSCs to epicardial lineages by stage-specific modulation of canonical WNT signaling and the long-term maintenance of hPSC-derived epicardial cells via inhibition of TGFβ signaling.

Figures 9A, 9B, 9C:
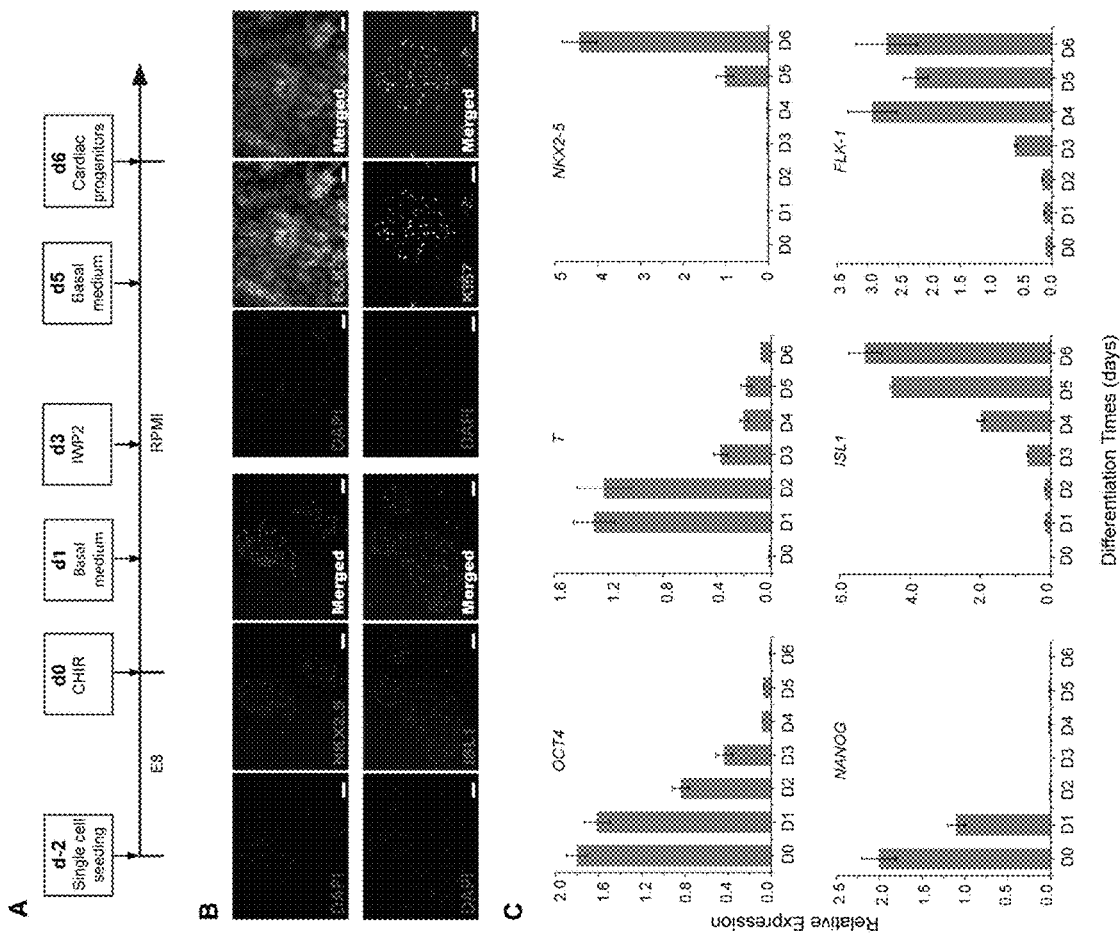

FIGS. 9A-9C (FIGS. 9A-9C) present albumin-free differentiation of NKX2.5+ISL1+FLK-1+ cardiac progenitors from hPSCs by small molecule modulation of Wnt signaling. (A) Schematic of the protocol for defined, albumin-free differentiation of hPSCs to cardiac progenitors in RPMI medium. (B) H13 hESCs were differentiated as illustrated in (A), re-passaged on day 6 and immunostained for indicated markers on day 7. Scale bars, 100 μm. (C) H13 hESCs were differentiated as illustrated in (A) and developmental gene expression was assessed by quantitative RT-PCR at indicated time points. Data are represented as mean±SEM of at least three independent replicates.

Figures 1A, 1B, 1C:
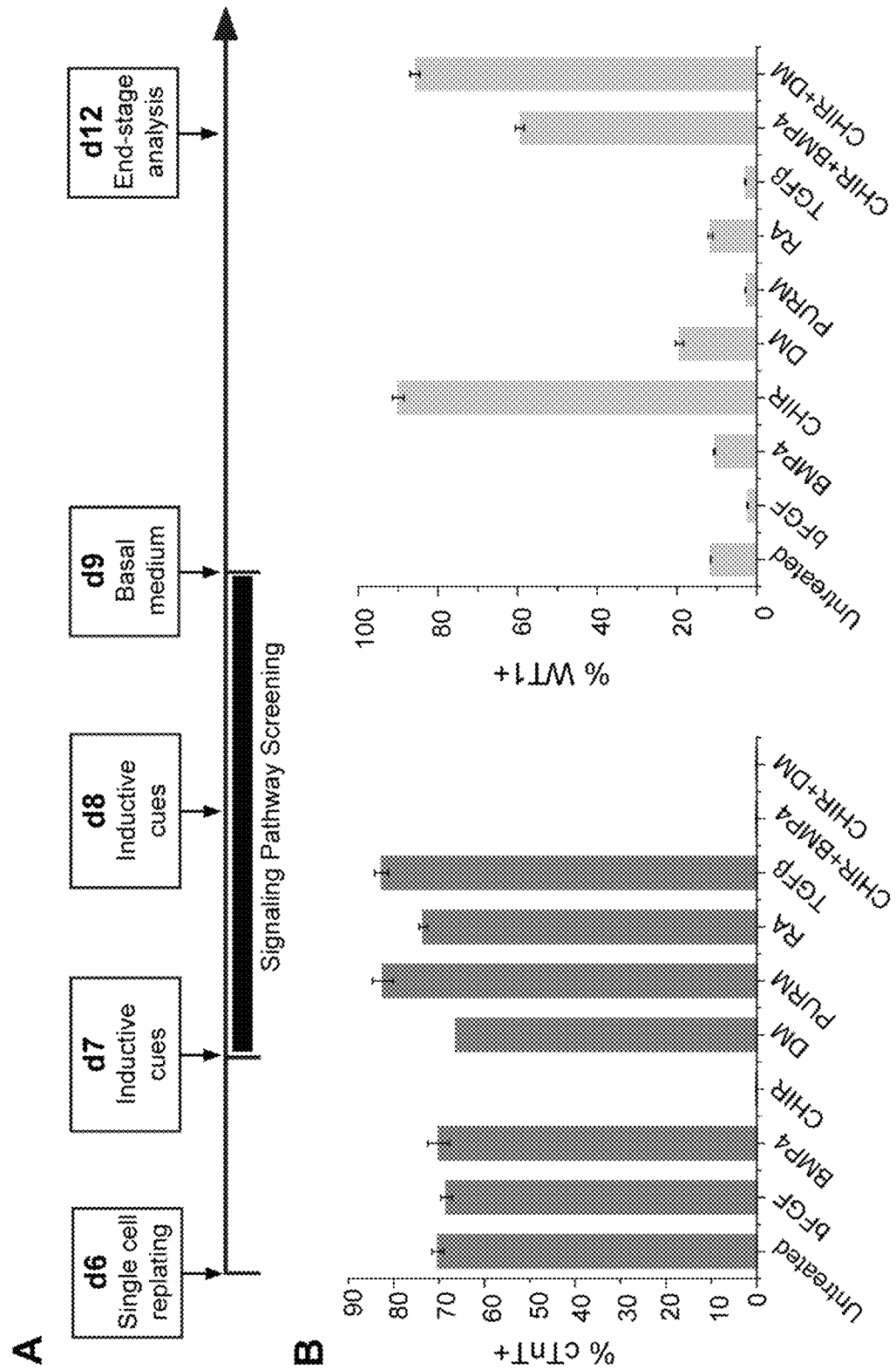
FIGS. 1A-1C (FIGS. 1A-1C) demonstrate that temporal Wnt signaling modulation is sufficient for epicardial linage specification from hPSC-derived cardiac progenitors. A schematic representation of protocols used to differentiate Nkx2.5+Isl1+ cardiac progenitors toward the epicardial lineages is presented in (A). H13 hESC-derived day 12 cultures were subjected to flow cytometry analysis (B) and immunostaining analysis (C) for Wilms' tumor suppressor protein 1 (WT1) and cTnT. Scale bars, 100 μm. Data are represented as mean±SEM of at least three independent replicates.
Figure 10:
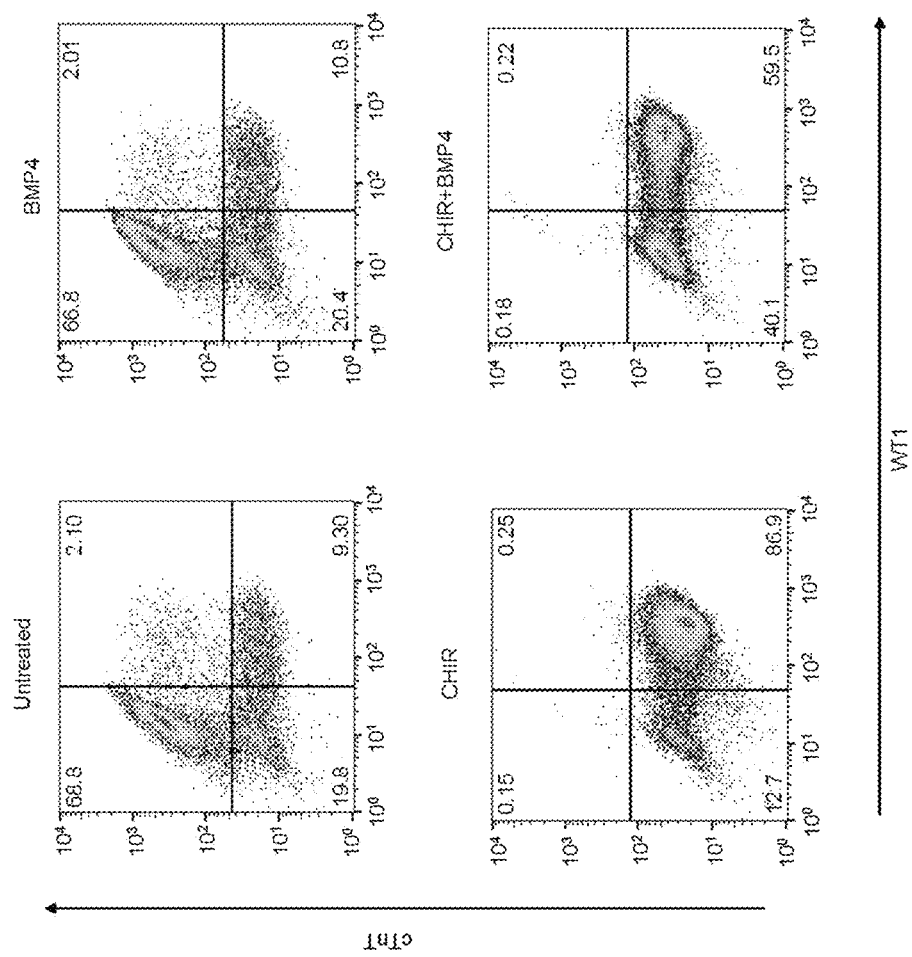

FIG. 10 (FIG. 10) presents flow cytometry analysis of cTnT and WT1 expression in day 12 H13 hESC cultures differentiated as shown in FIG. 1A in the presence or absence of 2 μM CHIR99021 and 10 ng/mL BMP4.

Figures 3A, 3B, 3C, 3D, 3E:
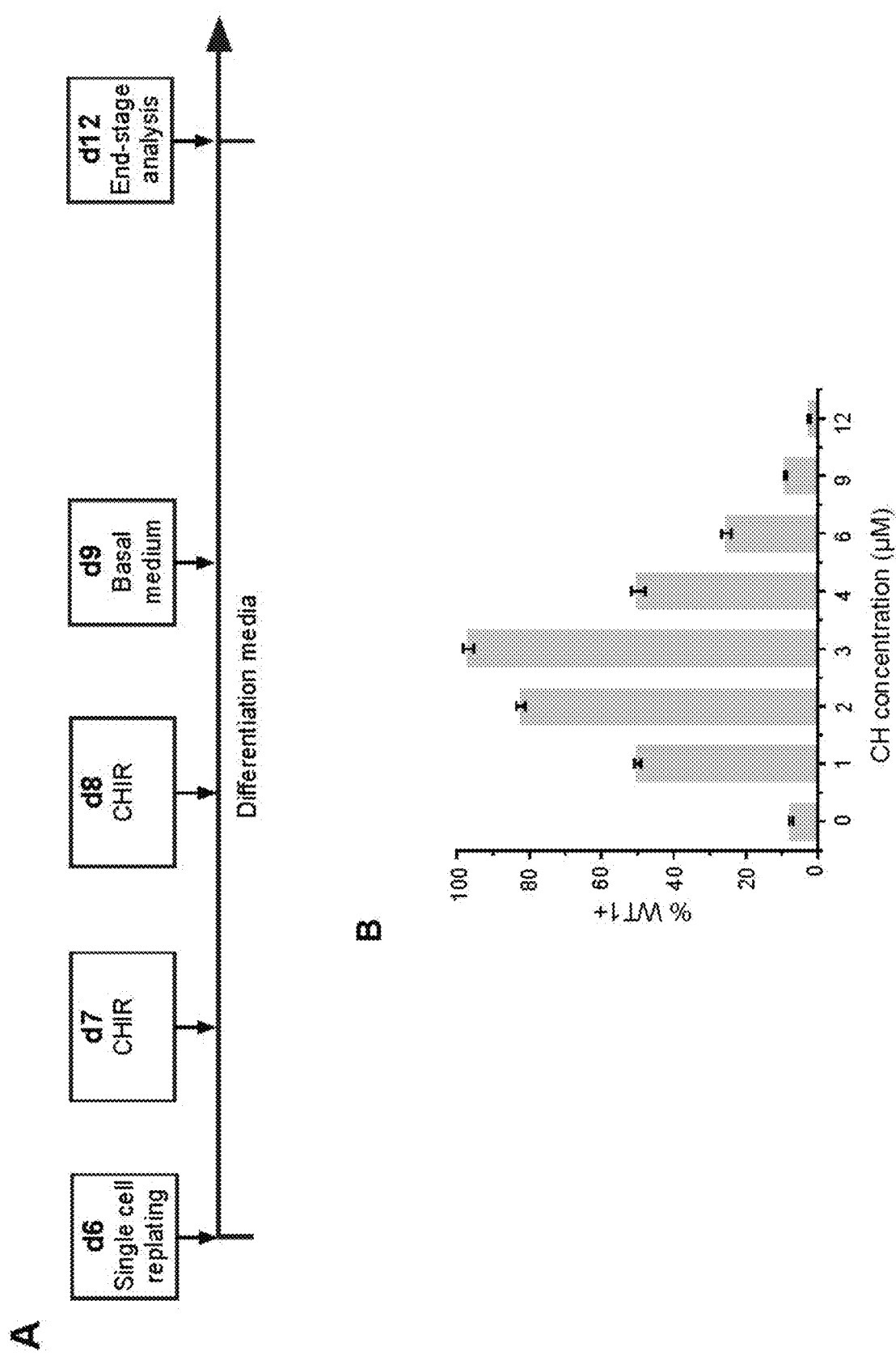
FIGS. 3A-3E (FIGS. 3A-3E) demonstrate use of chemically-defined, albumin-free conditions to generate WT1+ epicardial cells. (A) Schematic of the protocol for chemically-defined differentiation of hPSC-derived cardiac progenitors to WT1+ epicardial cells via GSK3 inhibition. (B) H13 hESC-derived day 6 cardiac progenitor cells were cultured as illustrated in (A) in LaSR basal medium with indicated CHIR99021 (CH) concentrations. At day 12, cells were analyzed for WT1 expression by flow cytometry. (C) Representative flow analysis of WT1-eGFP knockin ES03-derived epicardial cells with indicated CHIR concentration. (D) H13 hESC-derived day 6 cardiac progenitor cells were cultured as illustrated in (A) with the indicated day 6 cell seeding density in LaSR basal medium. At day 12, cells were analyzed for WT1 expression by flow cytometry. (E) H13 hESC-derived day 6 cardiac progenitor cells were seeded at a density of 0.06 million cells/cm$^2$ and cultured as illustrated in (A) with 3 μM CHIR99021 in the indicated basal medium. At day 12, cells were analyzed for WT1 expression by flow cytometry. Data are represented as mean±SEM of at least three independent replicates.
Figure 11:
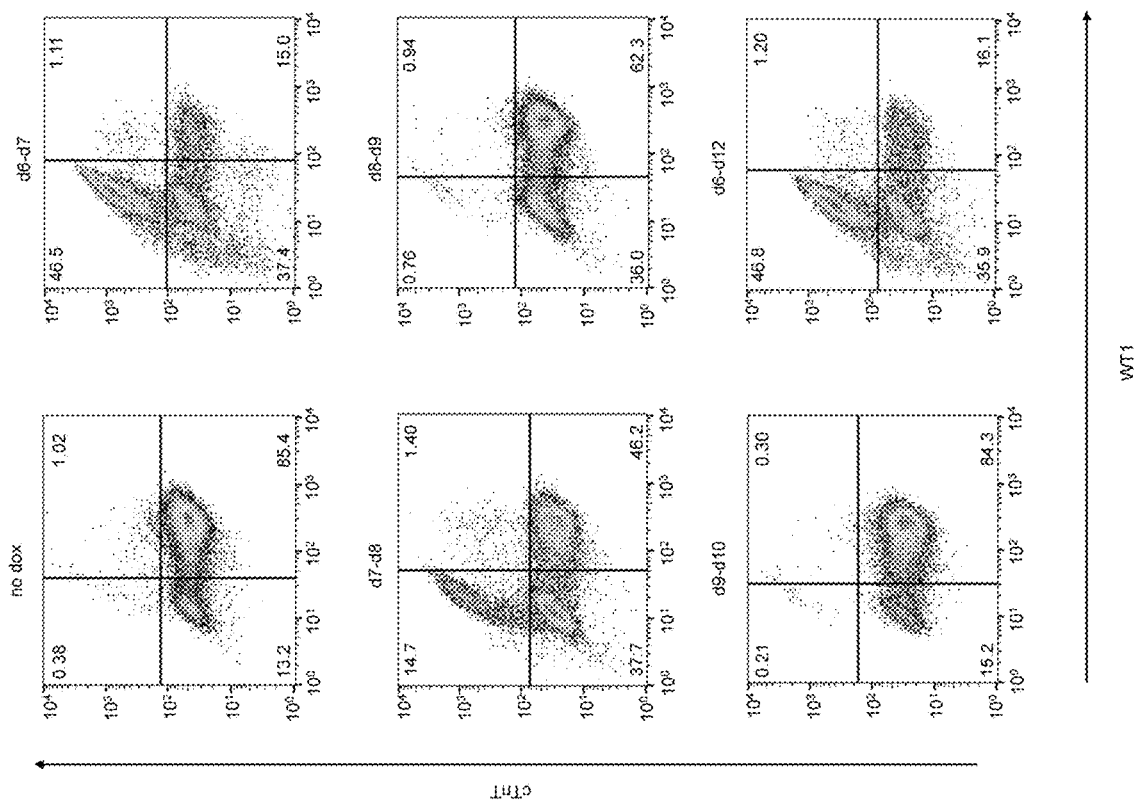

FIG. 11 (FIG. 11) demonstrates 19-9-11 ishcat-1 iPSC-derived day 6 cardiac progenitor cells differentiated as illustrated in FIG. 3A with 2 μg/ml doxycycline addition at the indicated times. Representative flow cytometry analysis of cTnT and WT1 expression with the indicated dox treatments were shown.

Figures 12A, 12B, 12C:
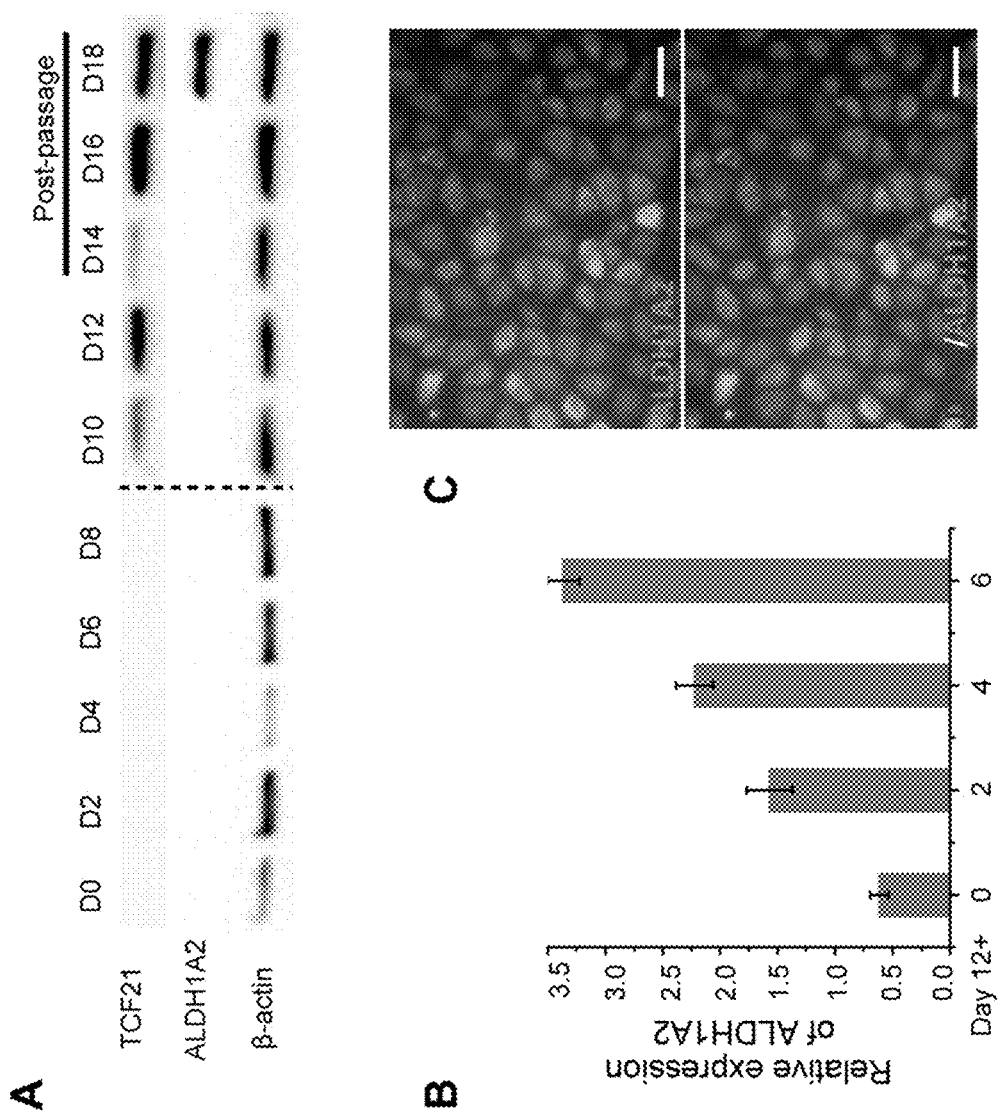

FIGS. 12A-12C (FIGS. 12A-12C) demonstrate epicardial cells maturation following passage at a low density in chemically-defined medium. H13 hESC-derived day 6 cardiac progenitor cells were seeded at a density of 0.06 million cells per cm² as illustrated in FIG. 5A in RPMI/Vc/Ins medium with 3 μM CHIR99021 from day 7 to day 9. At different time points, TCF21 and ALDH1A2 (A) expression was assessed by western blot. After passage at a density of 0.05 million cells per cm², differentiated cultures were subjected to qPCR (B) and immunostaining (C) analysis of ALDH1A2. Scale bars, 50 μm. Data are represented as mean±SEM of at least three independent replicates.

Figures 13A, 13B:
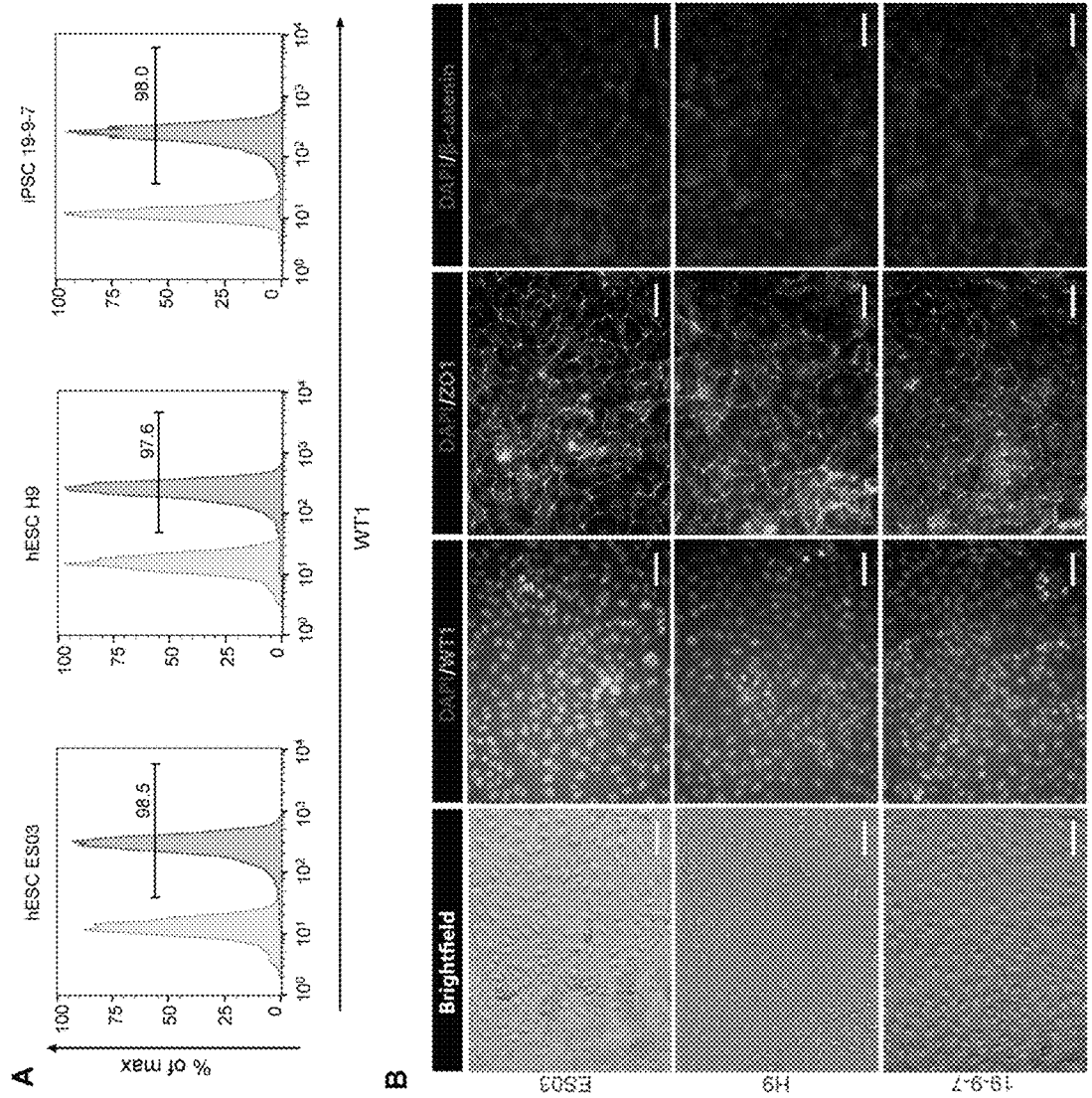

FIGS. 13A-13B (FIGS. 13A-13B) show differentiation of multiple hESC and iPSC lines to epicardial cells. Epicardial cells were generated as described in FIG. 5A from different hPSC lines: hESC H9, hESC ES03, iPSC 19-9-7. Day 12 pro-epicardial cells were subjected to flow cytometry analysis of WT1 expression (A), and representative contrast and immunostaining images of WT1, ZO1 and β-catenin of post-passage day 18 epicardial cells are shown in B. Scale bars, 50 μm.

Figure 14:
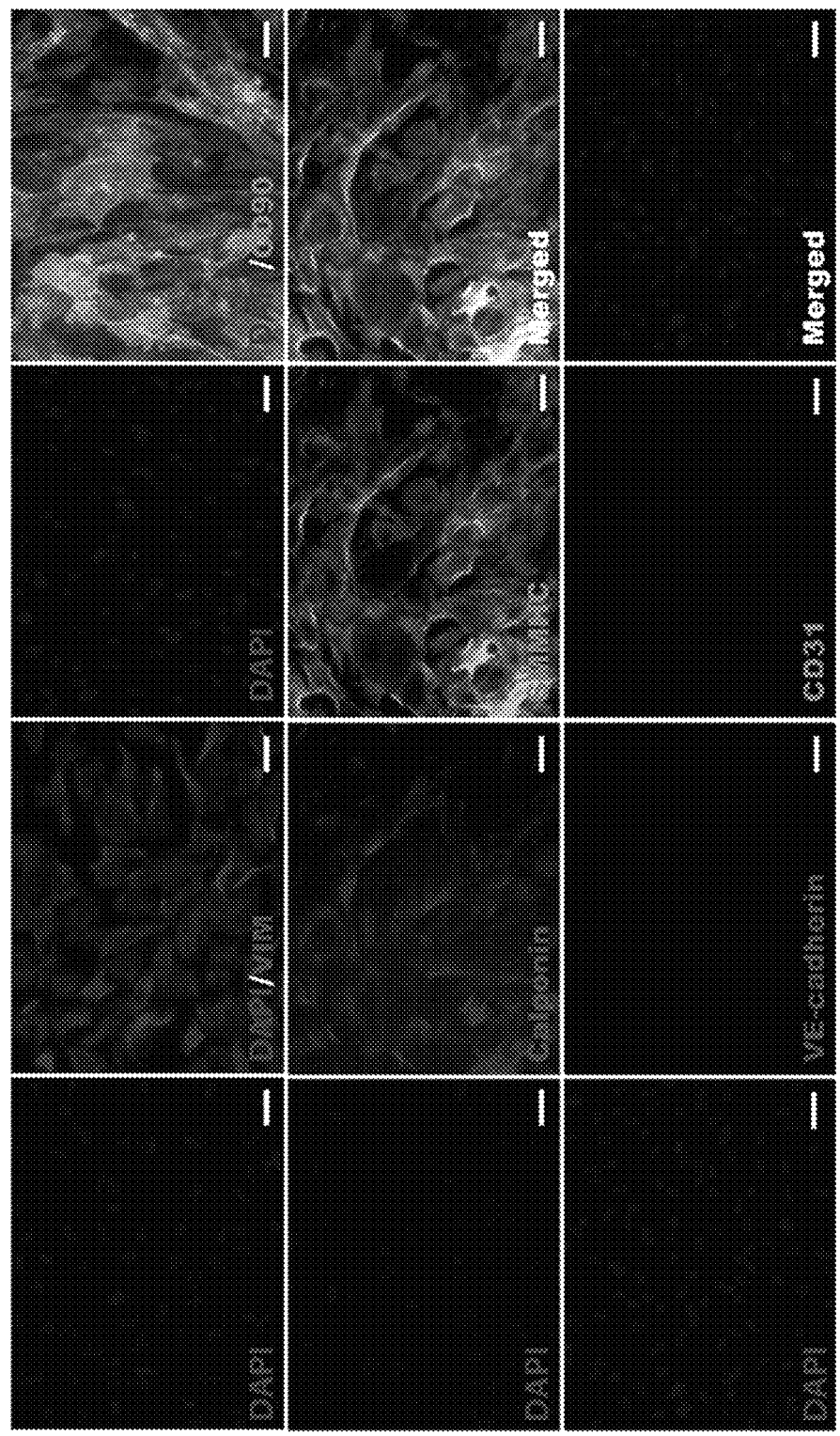

FIG. 14 (FIG. 14) demonstrates that epicardial cells underwent EMT in response to bFGF and TGFβ1 treatment. Immunostaining analysis of indicated fibroblast, smooth muscle and endothelial cell markers in LaSR basal medium with bFGF and bFGF+TGFβ, and EGM-2 medium, respectively. Data are represented as mean±SEM of at least three independent replicates.

FIGS. 15A-15D (FIGS. 15A-15D) present data from long-term maintenance of 19-9-11 iPSC-derived epicardial cells. hPSCs were differentiated to epicardial cells as illustrated in FIG. 5A, passaged and counted every four days in the presence of the indicated TGFβ inhibitors: 0.5 μM A83-01 or 2 μM SB431542. The population doublings were calculated and shown in (A), and day 48 cultures were subjected for flow analysis of ALDH1A2 (B) and Ki67 (C) expression. (D) Representative phase contrast and immunostaining images of WT1, ZO1 and β-catenin in day 48 epicardial cells treated with A83-01 are shown. Scale bars, 50 μm.

FIGS. 16A-16G (FIGS. 16A-16G) demonstrate that hPSC-derived epicardial cells are functionally similar to primary epicardial cells both in vitro and in vivo. (A) Hierarchical clustering of the top 50 significantly enriched pathways in indicated cell types. The color bar indicates the absolute normalized enrichment score (NES) for the enriched pathways. (B) 3D scores plot of first 3 principal components (PCs) from the PCA. The ellipses show the 95% confidence limit and each data point corresponds to different biological samples. Black arrows show the development transition from hPSCs to mesoderm, from which CMs and epicardial cells arise. (C) Venn diagram showing the number of pathways which are enriched in different cell types (relative to hPSCs). Top 150 significantly enriched pathways (p<0.05), ranked by absolute NES for each cell type was used for analysis. (D) The cardiac fibroblast-derived extracellular matrix (CF-ECM) patch seeded with cells was photographed at time of placement and 12 days after transplantation. Black arrows denote the sutures for MI and white arrows denote the CF-ECM scaffold. Scale bars, 1 cm. Representative photomicrographs (E) of eGFP-positive cells in 2-, 6-, and 12-day sections are shown. Scale bars, 100 μm. After 12 days, hearts were harvested and representative hematoxilin and eosin stain (HE stain) (F), vimentin (VIM) and calponin (G) stain of cross-sections of the heart are shown. Arrows denote the scaffold. Scale bar, 100 μm.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The methods and compositions provided herein are based at least in part on the Inventors' discovery that differentiation stage-specific modulation of canonical Wnt signaling is sufficient for efficient epicardial induction from human pluripotent stem cells (hPSCs) under chemically defined, albumin-free conditions. Activation of Wnt signaling induces mesodermal differentiation, while subsequent Wnt inhibition drives cardiac specification. Reactivation of Wnt in cardiac progenitors specifies epicardial cells. These hPSC-derived epicardial cells retain many characteristics of primary epicardial cells, including formation of a polarized epithelial sheet, expression of key epicardial genes Wilms' tumor suppressor protein 1 (WT1), TCF21, TBX18, and ALDH1A2, and the ability to undergo epithelial-to-mesenchymal transition (EMT) to generate fibroblast and vascular smooth muscle lineages. In addition, inhibition of TGFβ pathway signaling via culture in the presence of small molecules permits long-term maintenance of hPSC-derived epicardial cells in vitro. The chemically defined platform described here should be widely useful for generating functional epicardial cells for both research and clinical applications. The epicardial differentiation process provided herein is chemically defined and albumin-free, and generates epicardial cells from human pluripotent stem cells at a greater yield and lower cost than existing methods. In addition, these cells are more suitable for translational applications since they are derived in the absence of xenogeneic components. The methods provided herein have valuable applications such as inexpensive and reproducible generation of human epicardial cells. Generating human epicardial cells in completely chemically-defined, xeno-free conditions can facilitate translation of these cells to regenerative therapies and other clinical applications. As described in further detail below, the Inventors' xenogeneic material-free, albumin-free protocols target key regulatory elements of the Wnt/β-catenin signaling pathway, simplifying the steps and components involved in deriving cardiomyocyte progenitors and epicardial cells from pluripotent stem cells.

Accordingly, in a first aspect, provided herein is a method for generating a population of human epicardial cells, where the method comprises differentiating cardiac progenitor cells (such as human pluripotent stem cell-derived cardiac progenitor cells) under conditions that promote differentiation of the cardiac progenitors into epicardial cells. As used herein, the term "epicardial cells" refers to cells of the epicardial lineage obtained according to a method provided herein. Epicardial cells are characterized and identified by expression of transcription factors including Wilms' tumor suppressor protein (WT1), TCF21, and TBX18. WT1 is a transcription factor expressed in epicardium and epicardium-derived cells (EPDC) as well as in many cells of the early proepicardium (PE).

Preferably, the method comprises (i) generating or obtaining a population of cardiac progenitor cells; (ii) activating Wnt/β-catenin signaling in the cardiac progenitor cells of step (i) for a period of about two days; and (iii) culturing the population of step (ii) for about two days to about ten days to obtain a cell population comprising epicardial cells. Any human cardiac progenitor cell can be used according to the methods provided herein as long as the cardiac progenitor cell is positive for the expression of one or more of the following cardiac lineage markers: Isl1, Flk-1, and Nkx2.5. In some cases, the cardiac progenitor cells for step (ii) are passaged or unpassaged cardiac progenitors cells, where the passaged cells are from culture day 4, day 5, day 6, or day 7. As described herein, exogenous TGFβ superfamily growth factors such as Bone Morphogenetic Protein 4 (BMP4) are not required to generate cells of the epicardial lineage from human pluripotent cells.

As will be appreciated by those of ordinary skill in the art, Wnt/β-catenin signaling can be activated by modulating the function of one or more proteins that participate in the Wnt/β-catenin signaling pathway to increase β-catenin expression levels or activity, TCF and LEF expression levels, or β-catenin/TCF/LEF induced transcriptional activity.

In some embodiments, activation of Wnt/β-catenin signaling is achieved by inhibiting Gsk3 phosphotransferase activity or Gsk3 binding interactions. While not wishing to be bound by theory, it is believed that inhibition of Gsk3 phosphorylation of β-catenin will inhibit tonic degradation of β-catenin and thereby increase the level of β-catenin and activity to drive differentiation of pluripotent stem cells to an endodermal/mesodermal lineage. Gsk3 inhibition can be achieved in a variety of ways including, but not limited to, providing small molecules that inhibit Gsk3 phosphotransferase activity, RNA interference knockdown of Gsk3, and overexpression of dominant negative form of Gsk3. Dominant negative forms of Gsk3 are known in the art as described, e.g., in Hagen et al. (2002), *J Biol Chem*, 277 (26):23330-23335, which describes a Gsk3 comprising a R96A mutation.

In some embodiments, Gsk3 is inhibited by contacting a cell with a small molecule that inhibits Gsk3 phosphotransferase activity or Gsk3 binding interactions. Suitable small molecule Gsk3 inhibitors include, but are not limited to, CHIR99021, CHIR98014, BIO-acetoxime, BIO, LiCl, SB 216763, SB 415286, AR A014418, 1-Azakenpaullone, Bis-7-indolylmaleimide, and any combinations thereof. In some embodiments, any of CHIR99021, CHIR98014, and BIO-acetoxime are used to inhibit Gsk3 in pluripotent stem cells in the differentiation methods described herein. In one embodiment, the small molecule Gsk3 inhibitor to be used is CHIR99021 at a concentration ranging from about 3 μM to about 9 μM, e.g., about 3 μM, 4 μM, 5 μM, 6 μM, 7 μM, 8 μM, 9 μM or another concentration of CHIR99021 from about 3 μM to about 9 μM. In another embodiment, the small molecule Gsk3 inhibitor to be used is CHIR98014 at a concentration ranging from about 0.1 μM to about 1 μM, e.g., about 0.1 μM, 0.2 μM, 0.3 μM, 0.4 μM, 0.5 μM, 0.6 μM, 0.7 μM, 0.8 μM, 0.9 μM or another concentration of CHIR98014 from about 0.1 μM to about 1 μM. In another embodiment, the small molecule Gsk3 inhibitor to be used is BIO-acetoxime at a concentration ranging from about 0.1 μM to about 1 μM, e.g., about 0.1 μM, 0.2 μM, 0.3 μM, 0.4 μM, 0.5 μM, 0.6 μM, 0.7 μM, 0.8 μM, 0.9 μM or another concentration of BIO-acetoxime from about 0.1 μM to about 1 μM.

In other embodiments, Gsk3 activity is inhibited by RNA interference knockdown of Gsk3. For example, Gsk3 expression levels can be knocked-down using commercially available siRNAs against Gsk3, e.g., SignalSilence® GSK-3α/β siRNA (catalog #6301 from Cell Signaling Technology®, Danvers, Mass.), or a retroviral vector with an inducible expression cassette for Gsk3, e.g., a commercially available Tet-inducible retroviral RNA interference (RNAi) system from Clontech (Mountain View, Calif.) Catalog No.

630926, or a cumate-inducible system from Systems Biosciences, Inc. (Mountain View, Calif.), e.g., the SparQ® system, catalog no. QM200PA-2.

In other embodiments, the Wnt/β-catenin signaling pathway is activated by overexpressing β-catenin itself, e.g., human β-catenin (exemplary nucleotide and amino acid sequences are found at GenBank Accession Nos: X87838 and CAA61107.1, respectively). In one embodiment, β-catenin overexpression is achieved using an inducible expression system, e.g., any of the just-mentioned inducible expression systems. Alternatively, a constitutively active, stabilized isoform of β-catenin is used, which contains point mutations S33A, S37A, T41A, and S45A as described, e.g., in Baba et al. (2005), *Immunity* 23(6):599-609.

In yet other embodiments, Wnt/β-catenin signaling pathway activation in pluripotent stem cells is achieved by contacting the cells with an agent that disrupts the interaction of β-catenin with Axin, a member of the β-catenin destruction complex. Disruption of the Axin/β-catenin interaction allows β-catenin to escape degradation by the destruction complex thereby increasing the net level of β-catenin to drive β-catenin signaling. For example, the Axin/β-catenin interaction can be disrupted in pluripotent cells by contacting the cells with the compound 5-(Furan-2-yl)-N-(3-(1H-imidazol-1-yl)propyl)-1,2-oxazole-3-carboxamide ("SKL2001"), which is commercially available, e.g., as catalog no. 681667 from EMD4 Biosciences. An effective concentration of SKL2001 to activate Wnt/β-catenin signaling ranges from about 10 μM to about 100 μM, about 20 μM, 30 μM, 40 μM, 50 μM, 60 μM, 70 μM, 80 μM, 90 μM or another concentration of SKL2001 from about 10 μM to about 100 μM.

In some embodiments, activation (or re-activation) of Wnt/β-catenin pathway is initiated 36 hours following the inhibition step e.g., at least about 36 hours to about 72 hours after the beginning of the inhibition step.

The methods provided herein produce isolated populations of pluripotent stem cell-derived epicardial cells, where the isolated population is a substantially pure population of epicardial cells. As used herein, "isolating" and "isolated" refer to separating, selecting, or enriching for a cell type of interest or subpopulation of cells from surrounding, neighboring, or contaminating cells or from cells of another type. As used herein, the term "substantially pure" refers to a population of cells that is at least about 75% (e.g., at least about 75%, 85%, 90%, 95%, 98%, 99% or more) pure, with respect to epicardial cells making up a total cell population. In other words, the term "substantially pure" refers to a population of epicardial cells of the present invention that contains fewer than about 20%, fewer than about 10%, or fewer than about 5% of non-epicardial cells (e.g., cardiomyocytes) when directing differentiation to obtain cells of the epicardial lineage. The term "substantially pure" also refers to a population of epicardial cells of the present invention that contains fewer than about 20%, about 10%, or about 5% of non-epicardial cells in an isolated population prior to any enrichment, expansion step, or differentiation step. Typically, a population comprising epicardial cells obtained by the disclosed methods comprises a very high proportion of epicardial cells. In some embodiments, the cell population comprises about 50% to about 99% epicardial cells, e.g., about 52%, 55%, 67%, 70%, 72%, 75%, 80%, 85%, 90%, 95%, 98%, or another percent of epicardial cells from about 50% to about 99% epicardial cells.

Epicardial cells can be identified by the presence of one or more epicardial markers. Useful gene expression or protein markers for identifying epicardial cells include, but are not limited to, Wilms' tumor suppressor protein (WT1), TCF21, Tbx18, and combinations thereof. Preferably, the method yields a cell population, at least 95% (e.g., at least 95%, 96%, 97%, 98%, 99% or more) of which are epicardial cells positive for expression of Wilms' tumor suppressor protein (WT1). Molecular markers of the epicardium can be detected at the mRNA expression level or protein level by standard methods in the art. In some embodiments, no cell separation step or method is used to obtain a second cell population comprising at least 70% WT1$^+$ cells or at least 85% WT1$^+$ cells. In other embodiments, the proportion of epicardial cells in a population of cells obtained in the described methods is enriched using a cell separation, cell sorting, or enrichment method, e.g., fluorescence activated cell sorting (FACS), enzyme-linked immunosorbent assay (ELISA), magnetic beads, magnetic activated cell sorting (MACS), laser-targeted ablation of non-epicardial cells, and combinations thereof. Preferably, FACS is used to identify and separate cells based on cell-surface antigen expression. In some embodiments, certain epicardial functional criteria are also assessed. Such functional epicardial cell criteria include, without limitation, formation of a polarized epithelial sheet and the ability to undergo epithelial-to-mesenchymal transition (EMT) (in vitro or in vivo) to generate fibroblast and vascular smooth muscle lineages.

As described above, any human cardiac progenitor cell can be used according to the methods provided herein as long as the cardiac progenitor cell is positive for the expression of one or more of the following cardiac lineage markers: Isl1, Flk-1, and Nkx2.5. In exemplary embodiments, human cardiac progenitor cells are obtained by directing differentiation of human pluripotent stem cells into the mesodermal and cardiac lineages. In such cases, the method comprises the steps of: (a) activating Wnt/β-catenin signaling in human pluripotent stem cells by culturing the human pluripotent stem cells to obtain a first cell population; and (b) inhibiting Wnt/β-catenin signaling in the first cell population by culturing the first cell population in the presence of an agent that inhibits canonical Wnt/β-catenin pathway signaling to obtain a second cell population comprising human cardiac progenitor cells. Preferably, each culturing step is performed under chemically defined, xeno-free, and albumin-free conditions. For purposes of this disclosure, "xeno-free" means having no xenogeneic products of non-human animal origin, such as cells, tissues and/or body fluids, or any tissue or blood components, such as serum, which contain variable and undefined factors. Xeno-free medium and culture substrates are made up of known or "defined" components, which reduces the risk of viral contamination, prion transmission, and the batch-to-batch variability that is present using an undefined medium. Accordingly, for human cells, a xeno-free culture medium is defined as a culture medium essentially free of animal components, wherein the animal is not a human.

In exemplary embodiments, human pluripotent stem cell-derived cardiac progenitor cells are singularized and replated at a low cell density in a basal culture medium. Optionally, such single cell replating is followed by period of outgrowth before proceeding to activation of Wnt/β-catenin pathway signaling according to a method of generating epicardial cells as provided herein.

As will be appreciated by those of ordinary skill in the art, Wnt/β-catenin signaling can be inhibiting by modulating the function of one or more proteins that participate in the Wnt/β-catenin signaling pathway to decrease β-catenin levels or activity, decrease TCF and LEF expression levels, or decrease β-catenin/TCF-LEF-induced transcriptional activity. For example, inhibition of Wnt/β-catenin pathway signaling includes inhibition of TCF/LEF-β-catenin mediated gene transcription. Wnt/β-catenin pathway signaling can be inhibited in various ways including but not limited to providing small molecule inhibitors, RNA interference, or blocking antibodies against functional canonical Wnt ligands or Wnt pathway receptors (e.g., Frizzled and LRP5/6); providing small molecules that promote degradation of β-catenin and/or TCF/LEF; gene interference knockdown of β-catenin and/or TCF/LEF; overexpression of a dominant negative form of β-catenin lacking the sequence for binding to TCF/LEF; overexpressing Axin2 (which increases β-catenin degradation); providing a small molecule inhibitor of a TCF/LEF and β-catenin interaction; and providing a small molecule inhibitor of a TCF/LEF-β-catenin and DNA promoter sequence interaction.

In some cases, Wnt/β-catenin pathway signaling is inhibited by contacting a cell with one or more small molecule inhibitors of a Wnt ligand (e.g., a small molecule that inhibits secretion of the Wnt ligand) by inhibiting interactions between a Wnt ligand and its receptor. For example, the small molecule that inhibits Wnt/β catenin signaling can be a small molecule that prevents palmitoylation of Wnt proteins by porcupine (i.e., a porcupine inhibitor). In some embodiments, the small molecule that prevents palmitoylation of Wnt proteins by porcupine includes N-(6-Methyl-2-benzothiazolyl)-2-[(3,4,6,7-tetrahydro-4-oxo-3-phenylthieno[3,2-d]pyrimidin-2-yl)thio]-acetamide ("IWP2"), 2-(3,4,6,7-tetrahydro-3-(2-methoxyphenyl)-4-oxothieno[3,2-d]pyrimidin-2-ylthio)-N-(6-methylbenzo[d]thiazol-2-yl) acetamide ("IWP4"), 4-(2-Methyl-4-pyridinyl)-N-[4-(3-pyridinyl)phenyl]benzeneacetamide ("Wnt-C59"), or a combination thereof. In some such embodiments, the porcupine inhibitor is present in a concentration of from 0.2 μM to 5 μM. Other Wnt signaling inhibitors are available commercially, e.g., as Sigma catalog no. I0161; Benzoic acid, 2-phenoxy-, 2-[(5-methyl-2-furanyl)methylene]hydrazide ("PNU-74654"), e.g., Sigma catalog no. P0052.

In exemplary embodiments, a human pluripotent stem cell-derived mesodermal cell obtained according to step (a) as set forth above (e.g., cells characterized by the expression of mesodermal molecular marker Brachyury/T) is cultured in the presence of an agent that inhibits Wnt/β-catenin pathway signaling for about 8 hours to about 48 hours, e.g., about 8 hours, 12 hours, 16 hours, 20 hours, 24 hours, 28 hours, 32 hours, 36 hours, 40 hours, 44 hours, 48 hours, or another period of Wnt/β-catenin pathway signaling inhibition from about 8 hours to about 48 hours to obtain a population of cells. In one embodiment, the human pluripotent stem cell-derived cells characterized by the expression of mesodermal molecular markers are subjected to Wnt/β-catenin pathway signaling inhibition for about 24 hours.

In other cases, a human pluripotent stem cell-derived mesodermal cell obtained according to step (a) as set forth above (e.g., cells characterized by the expression of mesodermal molecular markers Brachyury/T) is cultured in the presence of one or more small molecule compounds that promote degradation of β-catenin. In some cases, such small molecule compounds are compounds that, directly or indirectly, stabilize Axin, which is a member of the β-catenin destruction complex, and thereby enhance degradation of β-catenin. Examples of Axin-stabilizing compounds include but are not limited to 3,5,7,8-Tetrahydro-2-[4-(trifluoromethyl)phenyl]-4H-thiopyrano[4,3-d]pyrimidin-4-one ("XAV939"), e.g., Sigma catalog no. X3004; 4-(1,3,3a,4,7,7a-Hexahydro-1,3-dioxo-4,7-methano-2H-isoindol-2-yl)-N-8-quinolinyl-Benzamide ("IWR-1") available commercially, e.g., as Sigma catalog no. I0161. In some cases, such small molecule compounds are compounds that, directly or indirectly, activate casein kinase 1α (CK1), which is a member of the β-catenin destruction complex, and thereby enhance degradation of β-catenin. Examples of CK1-stabilizing compounds include but are not limited to 6-(Dimethylamino)-2-[2-(2,5-dimethyl-1-phenyl-1H-pyrrol-3-yl)ethenyl]-1-methyl-4,4'-methylenebis[3-hydroxy-2-naphthalenecarboxylate] (2:1)-quinolinium ("Pyrvinium pamoate salt hydrate"), e.g., Sigma catalog no. P0027.

Typically, inhibition of Wnt/β-catenin signaling during step (ii) is maintained for at least about 1 day to about 6 days, e.g., about 1 day, 2 days, 2.5 days, 3 days, 3.5 days, 4 days, 5 days, or another period of Wnt/β-catenin signaling inhibition from at least about 1.5 days to about 6 days. In some embodiments, where a small molecule is used to inhibit Wnt/β-catenin signaling, such cells are contacted with a small molecule inhibitor of Wnt/β-catenin signaling for about 2 days, and then culture of this cell population continues in the substantial absence of the small molecule inhibitor. In other embodiments, where inducible RNA interference is used (e.g., with an inducing agent such as doxycycline to drive expression of tet-on expression cassette) to knockdown expression of β-catenin, induction and maintenance of β-catenin shRNA expression occurs for about 3.5 days, after which induction of β-catenin shRNA expression is terminated, and then culture of the first cell population continues in the substantial absence of the shRNA inducing agent.

A suitable working concentration range for small molecule Wnt/β-catenin signaling inhibitors is from about 0.1 μM to about 100 μM, e.g., about 2 μM, 5 μM, 7 μM, 10 μM, 12 μM, 15 μM, 18 μM, or another working concentration of one or more of the foregoing small molecule inhibitors ranging from about 0.1 μM to about 100 μM. For example, IWP2 or IWP4 or Wnt-C59 can be used at a working concentration of from about 1 to 4 μM. In another embodiment, IWP2 or IWP4 or Wnt-C59 is used at a working concentration of about 2.5 μM. In other embodiments, one or more of the above-mentioned small molecule inhibitors is used at the corresponding target $IC_{50}$.

In other embodiments, inhibition of Wnt/β-catenin pathway signaling is achieved using RNA interference to decrease the expression of one or more targets in the Wnt/β-catenin pathway. For example, in some cases, RNA interference is against β-catenin itself. In one embodiment, where one or more short hairpin interfering RNAs (shRNAs) knock down β-catenin expression, at least one of the following shRNA sequences is used: 5'-CCGGAGGTGC-TATCTGTCTGCTCTACTCGAGTAGAGCAGACAGA-TAGCACCTTTTTT-3' (SEQ ID NO:1) or 5'-CCGGG-CTTGGAATGAGACTGCTGATCTCGAGATCAGCA-GTCTCATTCCAAGCTTTTT-3' (SEQ ID NO:2). Such shRNAs may be transfected as synthetic shRNAs into the first cell population by a number of standard methods known in the art. Alternatively, shRNA sequences may be expressed from an expression vector, e.g., from a plasmid expression vector, a recombinant retrovirus, or a recombinant lentivirus.

In some cases, an inducible expression cassette is used to express an interfering RNA, e.g., an shRNA against β-catenin, as exemplified herein. The use of an inducible expression cassette allows temporal control of β-catenin knockdown. Such temporal control is well suited to the timing of Wnt/β-catenin signaling inhibition used in the differentiation methods described herein.

In an alternative method, Wnt/β-catenin signaling is inhibited using at least one antibody that blocks activation of a Wnt ligand receptor or binds to one or more Wnt ligand family members. Such antibodies are known in the art, as described in, e.g., an anti-Wnt-1 antibody described in He et al. (2004), *Neoplasia* 6(1):7-14. In other embodiments, the blocking antibody is targeted against a Wnt ligand receptor and blocks the interaction of Wnt ligands with the receptor, as described, e.g., in Gurney et al. (2012), *Proc. Natl. Acad. Sci. USA*, 109(29): 11717-22.

As used herein, "pluripotent stem cells" appropriate for use according to a method of the invention are cells having the capacity to differentiate into cells of all three germ layers. Pluripotent stem cells (PSCs) suitable for the differentiation methods disclosed herein include, but are not limited to, human embryonic stem cells (hESCs), human induced pluripotent stem cells (hiPSCs), non-human primate embryonic stem cells (nhpESCs), non-human primate induced pluripotent stem cells (nhpiPSCs). As used herein, "embryonic stem cells" or "ESCs" mean a pluripotent cell or population of pluripotent cells derived from an inner cell mass of a blastocyst. See Thomson et al., *Science* 282:1145-1147 (1998). These cells express Oct-4, SSEA-3, SSEA-4, TRA-1-60, and TRA-1-81, and appear as compact colonies having a high nucleus to cytoplasm ratio and prominent nucleolus. ESCs are commercially available from sources such as WiCell Research Institute (Madison, Wis.).

As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007). Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60, or Tra-1-81, but not SSEA-1). Induced pluripotent stem cells, however, are not immediately derived from embryos. As used herein, "not immediately derived from embryos" means that the starting cell type for producing iPS cells is a non-embryonic, non-pluripotent cell, such as a multipotent cell or terminally differentiated cell, such as somatic cells obtained from a post-natal individual.

Human iPS cells can be used according to a method described herein to obtain epicardial cells having the genetic complement of a particular human subject. For example, it may be advantageous to obtain epicardial cells that exhibit one or more specific phenotypes associated with or resulting from a particular disease or disorder of the particular mammalian subject. In such cases, iPS cells are obtained by reprogramming a somatic cell of a particular human subject according to methods known in the art. See, for example, Yu et al., *Science* 324(5928):797-801 (2009); Chen et al., *Nat. Methods* 8(5):424-9 (2011); Ebert et al., *Nature* 457(7227): 277-80 (2009); Howden et al., *Proc. Natl. Acad. Sci. U.S.A* 108(16):6537-42 (2011). Induced pluripotent stem cell-derived epicardial cells allow modeling of drug responses in epicardial cells obtained from an individual having, for example, a particular disease. Even the safest drugs may cause adverse reactions in certain individuals with a specific genetic background or environmental history. Accordingly, human subject specific iPS cell-derived epicardial cells are useful to identify genetic factors and epigenetic influences that contribute to variable drug responses.

Subject-specific somatic cells for reprogramming into iPS cells can be obtained or isolated from a target tissue of interest by biopsy or other tissue sampling methods. In some cases, subject-specific cells are manipulated in vitro prior to use. For example, subject-specific cells can be expanded, differentiated, genetically modified, contacted to polypeptides, nucleic acids, or other factors, cryo-preserved, or otherwise modified.

Chemically defined culture medium and substrate conditions for culturing pluripotent stem cells, as used in the methods described herein, are well known in the art. Preferably, a serum-free, chemically defined, albumin-free culture medium is used. As used herein, the terms "chemically-defined culture conditions," "fully defined, growth factor free culture conditions," and "fully-defined conditions" indicate that the identity and quantity of each medium ingredient is known and the identity and quantity of supportive surface is known. As used herein, "serum-free" means that a medium does not contain serum or serum replacement, or that it contains essentially no serum or serum replacement. For example, an essentially serum-free medium can contain less than about 1%, 0.9%, 0.8%, 0.7%, 0.6%, 0.5%, 0.4%, 0.3%, 0.2% or 0.1% serum. As used herein, the term "albumin-free conditions" indicates that the culture medium used contains no added albumin in any form, including without limitation Bovine Serum Albumin (BSA) or any form of recombinant albumin.

In some embodiments, pluripotent stem cells to be differentiated according to the methods disclosed herein are cultured in the presence of a serum-free, albumin-free, chemically-defined culture medium such as LaSR basal medium (a serum-free culture medium containing Advanced DMEM/F12, 2.5 mM GlutaMAX, and supplemented with 60 μg/mL ascorbic acid), mTESR-1® medium (StemCell Technologies, Inc., Vancouver, CA), or Essential 8® medium (Life Technologies, Inc.) on a Matrigel™ substrate (BD Biosciences, NJ) or Synthemax surfaces (Corning) according to the manufacturer's protocol. A number of known basal culture media are suitable for use throughout the differentiation methods described herein. Such basal cell culture media include, but are not limited to, RPMI, DMEM/F12 (1:3), DMEM/F12 (1:1), DMEM/F12 (3:1), F12, DMEM, and MEM. In exemplary embodiments, these basal cell culture media are supplemented with 50 to 200 μg/ml L-Ascorbic acid 2-phosphate sesquimagnesium salt hydrate (e.g., Sigma, catalog no. A8960). For each differentiation step described herein, cells are cultured in a medium that is substantially free of exogenous Bone Morphogenetic Proteins (BMPs) such as BMP4.

In exemplary embodiments, human pluripotent stem cells (e.g., human ESCs or iPS cells) are cultured in the absence of a feeder layer (e.g., a fibroblast layer) and in the presence of a chemically defined, xenogen-free ("xeno-free") substrate. For example, human pluripotent cells can be cultured in the presence of a substrate comprising vitronectin, a vitronectin fragment or variant, a vitronectin peptide, a self-coating substrate such as Synthemax® (Corning), or combinations thereof. In exemplary embodiments, the chemically-defined, xeno-free substrate is a plate coated in vitronectin peptides or polypeptides (e.g., recombinant human vitronectin).

In a further aspect, provided herein are compositions and methods for expanding a self-renewing population of human epicardial cells for an extensive period of time. This is because the invention provides compositions and methods of generating human epicardial cells which can be extensively expanded in vitro yet retain the ability to undergo an epithelial-to-mesenchymal transition (EMT) and differentiate into epicardium-derived cell types. The term "extensively expanded" as used herein refers to cell populations which have undergone at least about 25 or more cell population doublings and wherein the cells are non-senescent and are not immortalized. When cultured in the presence of an expansion medium comprising an inhibitor of TGFβ, epicardial cells obtained according to the methods provided herein are capable of undergoing at least 25 cell divisions (e.g., at least 25, 30, 35, or more cell divisions). Inhibitors of TGFB signaling that can be used include, without limitation, A83-01 or SB431542. As described in the Examples that follow, culture in the presence of an expansion medium comprising of A83-01 or SB431542 yielded hPSC-derived epicardial cells capable of at least 25 population doublings, generating more than 10 million cells from a single hPSC-derived epicardial cell clone. In some cases, a cell culture comprises a chemically defined, albumin-free expansion medium comprising an inhibitor of TGFβ signaling, and human self-renewing epicardial cells that proliferate in culture and maintain the ability to undergo EMT, where the epicardial cells are not immortalized. Therefore, provided herein is an expandable source of functional epicardial cells.

Articles of Manufacture

In another aspect, provided herein is a kit for generating human epicardial cells. In exemplary embodiments, the kit comprises (i) a culture medium suitable for differentiating human cardiac progenitor cells into epicardial cells; (ii) an agent that activates Wnt signaling in human cardiac progenitor cells; and (iii) instructions describing a method for generating human epicardial cells, the method employing the culture medium and the agent. In some cases, a kit provided herein further comprises or alternatively comprises instructions describing methods for long-term in vitro maintenance of human epicardial cells obtained according to a kit provided herein, where the method employs a culture medium suitable for maintaining human epicardial cells and an agent that supports long-term maintenance of such epicardial cells.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, preferred methods and materials are described herein.

In describing the embodiments and claiming the invention, the following terminology will be used in accordance with the definitions set out below.

As used herein, "about" means within 5% of a stated concentration range or within 5% of a stated time frame.

As used herein, "a medium consisting essentially of" means a medium that contains the specified ingredients and those that do not materially affect its basic characteristics.

The terms "defined culture medium," "defined medium," and the like, as used herein, indicate that the identity and quantity of each medium ingredient is known. The term "defined," when used in relation to a culture medium or a culture condition, refers to a culture medium or a culture condition in which the nature and amounts of approximately all the components are known.

As used herein, "effective amount" means an amount of an agent sufficient to evoke a specified cellular effect according to the present invention.

Cells are "substantially free" of exogenous genetic elements or vector elements, as used herein, when they have less that 10% of the element(s), and are "essentially free" of exogenous genetic elements or vector elements when they have less than 1% of the element(s). However, even more desirable are cell populations wherein less than 0.5% or less than 0.1% of the total cell population comprise exogenous genetic elements or vector elements. A culture, composition, or culture medium is "essentially free" of certain reagents, such as signaling inhibitors, animal components or feeder cells, when the culture, composition, and medium, respectively, have a level of these reagents lower than a detectable level using conventional detection methods known to a person of ordinary skill in the art or these agents have not been extrinsically added to the culture, composition, or medium.

The invention will be more fully understood upon consideration of the following non-limiting Examples. It is specifically contemplated that the methods disclosed are suited for pluripotent stem cells generally. All publications, patents, and patent applications disclosed herein are hereby incorporated by reference as if set forth in their entirety.

EXAMPLES

Example 1: Epicardial Lineage-Specific Differentiation of Human Pluripotent Stem Cells In this Example, we demonstrate that Wnt signaling and inhibition of TGFβ signaling is sufficient for epicardial induction and self-renewal, respectively, from hPSCs under chemically-defined, animal component-free conditions. The hPSC-derived epicardial cells were similar to primary epicardial cells both in vitro and in vivo. These findings improve our understanding of self-renewal mechanisms of the epicardium and have implications for stimulating epicardial regeneration via cellular or small molecule therapies. These hPSC-derived epicardial cells retain many characteristics of primary epicardial cells, including formation of a polarized epithelial sheet, expression of key epicardial genes such as Wilms' tumor suppressor protein (WT1), TBX18, and ALDH1A2, and the ability to undergo epithelial-to-mesenchymal transition (EMT) both in vitro and in vivo to generate fibroblast and vascular smooth muscle lineages. The chemically-defined platform described here rapidly generates epicardial cells from human pluripotent stem cells (hPSCs) and enables the assessment of the temporal roles of different signaling pathways during epicardium formation and proliferation.

Methods

Construction of Donor Plasmid and sgRNA: Human codon-optimized *Streptococcus pyogenes* wild-type Cas9 (pCas9-2A-eGFP #) was obtained from Addgene (plasmid #44719) and chimeric guide RNA expression cassette was cloned into this Cas9-2A-eGFP plasmid with two BbsI restriction sites for rapid sgRNA cloning. Two sgRNAs targeting at or near WT1 stop codon (1: AACTCCAGCTGGCGCTTTGA<u>GGG</u> (SEQ ID NO:3) and 2: GGACACTGAACGGTCCCCGA<u>GGG</u> (SEQ ID NO:4)) were used. To generate the WT1-2A-eGFP donor plasmid, DNA fragments of about 2 kb in length were PCR amplified from the genomic DNA before and after the stop codon of WT1 and were cloned into the OCT4-2A-eGFP donor plasmid[29] (Addgene #31938), replacing the OCT4 homologous arms.

Maintenance of hPSCs and TAT-Cre Treatment of WT1 Knock-in hPSCs: Transgene and vector-free human pluripotent stem cells (hPSCs) were maintained on Matrigel™ (Corning) or SyntheMax® (BD Biosciences)-coated plates in mTeSR1 or E8 medium (STEMCELL Technologies) according to previously published methods[18,30]. To remove PGK-Puro cassette from the WT1-2A-eGFP cells, targeted homozygous clones were treated with 2 μM TAT Cre Recombinase (Excellgen, EG-1001) for 6 hours in E8 medium. After two days, cells were singularized with Accutase and seeded into Matrigel™-coated 96-well plate at a density of 100 to 150 cells per well. After two weeks, cells were subjected for PCR genotyping.

Electroporation: Pre-treated hESCs with 10 μM ROCK inhibitor (Y27632) for 3 to 4 hours prior to electroporation. Cells were digested by Accutase (Innovative Cell Technologies) at 37° C. for 8 minutes and 2.5-3 million single cells were electroporated with 3 μg gRNA1, 3 μg gRNA2 and 6 μg WT1-2A-eGFP donor plasmids in 200 μL cold PBS-/- using the Gene Pulser Xcell System (Bio-Rad) at 320 V, 200 μF and 1000 'Ω(Time constant should be around 15 ms) in a 0.4 cm cuvette. Two electroporation were performed and approximately 5-6 million cells were subsequently plated onto Matrigel™-coated 10-cm dish in 10 mL mTeSR1 with 10 μM Y27632. 24 hours later, and every day afterwards, the medium was changed with fresh mTeSR1. Three days after electroporation, 1 μg/ml puromycin was added into the mTeSR1 for selection for about two weeks. Single cell clones were then picked into Matrigel™-coated 96-well plate and subjected for PCR genotyping after 4 to 7 days.

Cardiac Progenitor Induction Via Modulation of Canonical Wnt Signaling: When hPSCs maintained on a SyntheMax-coated surface achieved confluence, cells were singularized with Accutase (Innovative Cell Technologies) at 37° C. for 5 minutes and then seeded onto a SyntheMax-coated cell culture dish at 250,000 cells/cm$^2$ in mTeSR1 or E8 supplemented with 5 μM ROCK inhibitor Y-27632 (Selleckchem) (day −3) for 24 hours. Cells were then cultured in mTeSR1 or E8, changed daily. At day 0, cells were treated with 6 μM CHIR99021 (Selleckchem) for 24 hours in RPMI medium, followed by a change with RPMI medium at day 1. 2.5-5 μM IWP2 (Tocris) was added at day 3 and removed during the medium change at day 5.

Epicardial Cell Generation Via Activation of Canonical Wnt Signaling: At day 6, cardiac progenitor cells were singularized with Accutase at 37° C. for 5 minutes and then seeded onto a gelatin-coated cell culture dish at 20,000-80,000 cells/cm$^2$ in LaSR basal medium (advanced DMEM/F12 with 100 μg/mL ascorbic acid) or RPMI/Vc/Ins medium (100 μg/mL ascorbic acid and 1 μg/mL human recombinant or bovine insulin (Sigma)) with 5 μM ROCK inhibitor Y-27632 for 24 hours. At day 7, cells were treated with 1-9 μM CHIR99021 for 2 days in LaSR basal medium or RPMI/insulin/Vc medium. After 2 days, CHIR99021-containing medium was aspirated and cells were cultured in LaSR basal medium or RPMI/insulin/Vc medium without CHIR99021 for 3-5 additional days.

Long-Term Maintenance of hPSC-Derived Epicardial Cells: To expand the epicardial cells, confluent cells on day 3 or 4 of differentiation were split 1:3 at a density of 0.04 to 0.08 million cells/cm$^2$ using Versene (Life Technologies) or Accutase and routinely passaged onto gelatin-coated plates in LaSR basal medium or RPMI/Vc/Ins medium and 0.5 μM A83-01 (Stemgent) or 2 μM SB431542 (Stemgent) with medium changed daily until the cells reached confluence. Overnight treatment of 5 μM Y27632 and 1% human recombinant albumin (Sigma-Aldrich) on single cells during passage was used to improve cell attachment and survival, but they were not required once cells attached.

Single Cell Passage and EMT Induction: Confluent WT1+ cells were dissociated into single cells with Accutase at 37° C. for 5 minutes and then seeded onto a gelatin-coated cell culture dish at 10,000 cells/cm$^2$ in LaSR basal medium supplemented with 5 μM ROCK inhibitor Y-27632 for 24 hr. After 24 hours, medium was changed to LaSR basal medium and cells were treated with TGFβ1 or bFGF (R&D Systems) as indicated. Medium was changed every 3 days until analysis.

CF-ECM Scaffold to Transfer Epicardial Cells In Vivo to the Infarcted Heart: Immunodeficient mice were purchased from Harlan Laboratories and all procedures were carried out in accordance with protocols approved by the Institutional Animal Care and Use Committee. Myocardial infarction was induced 48 hours before the transplantation according to a previously described protocol[31]. CF-ECM scaffolds were seeded with 1 million ES03 eGFP hPSC-derived epicardial cells and incubated for 3 hours prior to transfer to the epicardial surface of the MI area. After transplantation, the chest was closed. After 2, 6, 12 days, the mouse hearts were harvested and excised for histology as previously described[31].

Immunostaining Analysis: Cells were fixed with 4% paraformaldehyde for 15 minutes at room temperature and then stained with primary and secondary antibodies (Table 1) in PBS plus 0.4% Triton X-100 and 5% non-fat dry milk (Bio-Rad). Nuclei were stained with Gold Anti-fade Reagent with DAPI (Invitrogen). An epifluorescence microscope (Leica DM IRB) with a QImaging® Retiga 4000R camera was used for imaging analysis.

Flow Cytometry Analysis: Cells were dissociated into single cells with Accutase for 10 minutes and then fixed with 1% paraformaldehyde for 20 minutes at room temperature and stained with primary and secondary antibodies (Table 1) in PBS plus 0.1% Triton X-100 and 0.5% BSA. Data were collected on a FACSCaliber flow cytometer (Beckton Dickinson) and analyzed using FlowJo. FACS gating was based on the corresponding isotype antibody control.

Genomic DNA Extraction and Genomic PCR: QuickExtract™ DNA Extraction Solution (Epicentre Cat. #QE09050) was used to rapidly extract genomic DNA from hESCs according to manufacture instructions. Genomic PCR was carried out using GoTaq Green Master Mix (Promega Cat. #M7123). PCR primer sequences are provided in the Table 2.

RT-PCR and Quantitative RT-PCR: Total RNA was prepared with the RNeasy mini kit (QIAGEN) and treated with DNase (QIAGEN). 1 μg RNA was reverse transcribed into cDNA via Oligo (dT) with Superscript III Reverse Transcriptase (Invitrogen). Real-time quantitative PCR was done in triplicate with iQSYBR Green SuperMix (Bio-Rad). GAPDH was used as an endogenous housekeeping control. PCR primer sequences are provided in the Table 2.

RNA Sequencing and Data Analysis: Total RNA of hPSC-derived epicardial was prepared with the Direct-zol™ RNA MiniPrep Plus kit (Zymo Research) according to the manufacture instructions. Human primary epicardial RNAs from 4 different donors were provided by our collaborator (Astra-Zeneca, Sweden). Samples were performed in Illumina HiSeq2500 by Biotechnology Center at University of Wisconsin-Madison. The resulting sequence reads were mapped to the human genome (hg19) using HISAT[32], and the RefSeq transcript levels (RPKMs) were quantified using the python script rpmkforgenes.py[33]. Hierarchical clustering of whole transcripts were then plotted using GENE-E. Fastq files of hPSCs[34-36], hPSC-derived ectoderm[35], endoderm[34], mesoderm[36] and CMs[37] were downloaded from Gene Expression Omnibus (GEO) (available at ncbi.nlm.nih.gov/geo/ on the World Wide Web) or ArrayExpress (available at ebi.ac.uk/arrayexpress on the World Wide Web). Principal component analysis (PCA) was performed using PLS Toolbox 8.1 (Eigenvector Technologies). The whole transcripts were preprocessed using auto-scaling method (subtracting the mean from the variables and dividing by the standard deviation) to study the variance. Pathway enrichment analysis was performed using Gene set enrichment analysis (GSEA) software[38]. The gene expression data for each cell type was compared with hPSCs and the significantly enriched pathways (p<0.05) were considered for further analysis. MATLAB 2013a (Mathworks Inc.) and Microsoft Excel (2013) were used to identify the unique and common pathways in different cell types. The absolute value of normalized enrichment score (NES) of the top 50 significantly enriched pathways for each cell type (ranked by the absolute NES) were further used for hierarchical clustering using GENE-E. To further investigate the similarity and differences in the number of enriched pathways in the three cell types: donor derived epicardial cells, hPSC derived epicardial cells and cardiomyocytes, top 150 significantly enriched pathways for each cell type were selected.

Western Blot Analysis: Cells were lysed in M-PER Mammalian Protein Extraction Reagent (Pierce) in the presence of Halt Protease and Phosphatase Inhibitor Cocktail (Pierce). Proteins were then separated by 10% Tris-Glycine SDS/PAGE (Invitrogen) under denaturing conditions and transferred to a nitrocellulose membrane. After blocking with 5% non-fat milk in TBST, the membrane was incubated with primary antibody (Table 1) overnight at 4° C. The membrane was then washed, incubated with an anti-mouse/rabbit peroxidase-conjugated secondary antibody for 1 hours at room temperature or overnight at 4° C., and developed by SuperSignal chemiluminescence (Pierce).

Statistical Analysis: Data are presented as mean±standard error of the mean (SEM). Statistical significance was determined by Student's t-test (two-tail) between two groups. P<0.05 was considered statistically significant.

Results

Chemically Defined Albumin-Free Conditions to Generate ISL1+NKX2.5+FLK-1+Cardiac Progenitors We previously demonstrated that temporal modulation of canonical Wnt signaling in RPMI basal medium (GiWi protocol) is sufficient to generate functional cardiomyocytes from hPSCs[39]. We found that ISL1+NKX2.5+FLK-1+ second heart field cardiac progenitor cells are generated as intermediates during the GiWi protocol (see FIG. 9A). When re-passaged on gelatin-coated plates in LaSR basal medium[19] on day 6, these hPSC-derived cardiac progenitors expressed progenitor markers including ISL1, NKX2.5 and FLK-1, as well as a proliferative marker KI67 (FIG. 9B). Molecular analysis of cardiac progenitor differentiation from hPSCs revealed dynamic changes in gene expression, with down-regulation of the pluripotency markers OCT4 and NANOG, and induction of the primitive streak like gene T[19,40] in the first 24 hr after CHIR99021 addition (FIG. 9C). Expression of cardiac progenitor markers ISL1, NKX2.5 and FLK-1 was first detected between days 3 and 5, and was significantly up-regulated at day 6 (FIG. 9C).

Wnt/β-Catenin Signaling Regulates Specification of Epicardial Lineages

Pro-epicardium arises from ISL1+NKX2.5+ second heart field progenitors in vivo[1,41]. To identify signaling mechanisms regulating cardiac progenitor specification to epicardial cells, we treated day 6 ISL1+NKX2.5+ progenitors with different small molecule and protein modulators of developmental signaling pathways for 48 hours (from day 7 to day 9) (FIG. 1A, Table 3). hPSC-derived cardiac progenitors formed more than 85% WT1+ putative epicardial cells following CHIR99021 treatment (FIGS. 1B-C), demonstrating that Wnt signaling induction between days 7 and 9 is sufficient to generate epicardial cells in the absence of other exogenous signaling. In the absence of CHIR, robust beating sheets of cTnT+ cardiomyocytes were observed (FIGS. 1B-C), suggesting that the activation status of canonical Wnt signaling at day 7 toggles epicardial vs. cardiomyocyte differentiation. Interestingly, untreated and BMP4-, dorsomorphin (DM)- and retinoic acid (RA)-treated cells also yielded about 10% WT1+ cells that were distinct from cTnT+ cells; only 2% cTnT+WT1+ cells were generated (FIGS. 1B-C and FIG. 10). In the presence of CHIR, BMP4 treatment did not generate cardiomyocytes, but instead yielded an unknown population at the expense of WT1+ cells. Inhibition of BMP4 signaling via DM resulted in a similar purity of WT1+ cells as CHIR treatment (FIG. 1B and FIG. 10), suggesting that BMP4 signaling is dispensable at this stage of epicardial development.

Figures 2A, 2B, 2C, 2D, 2E:
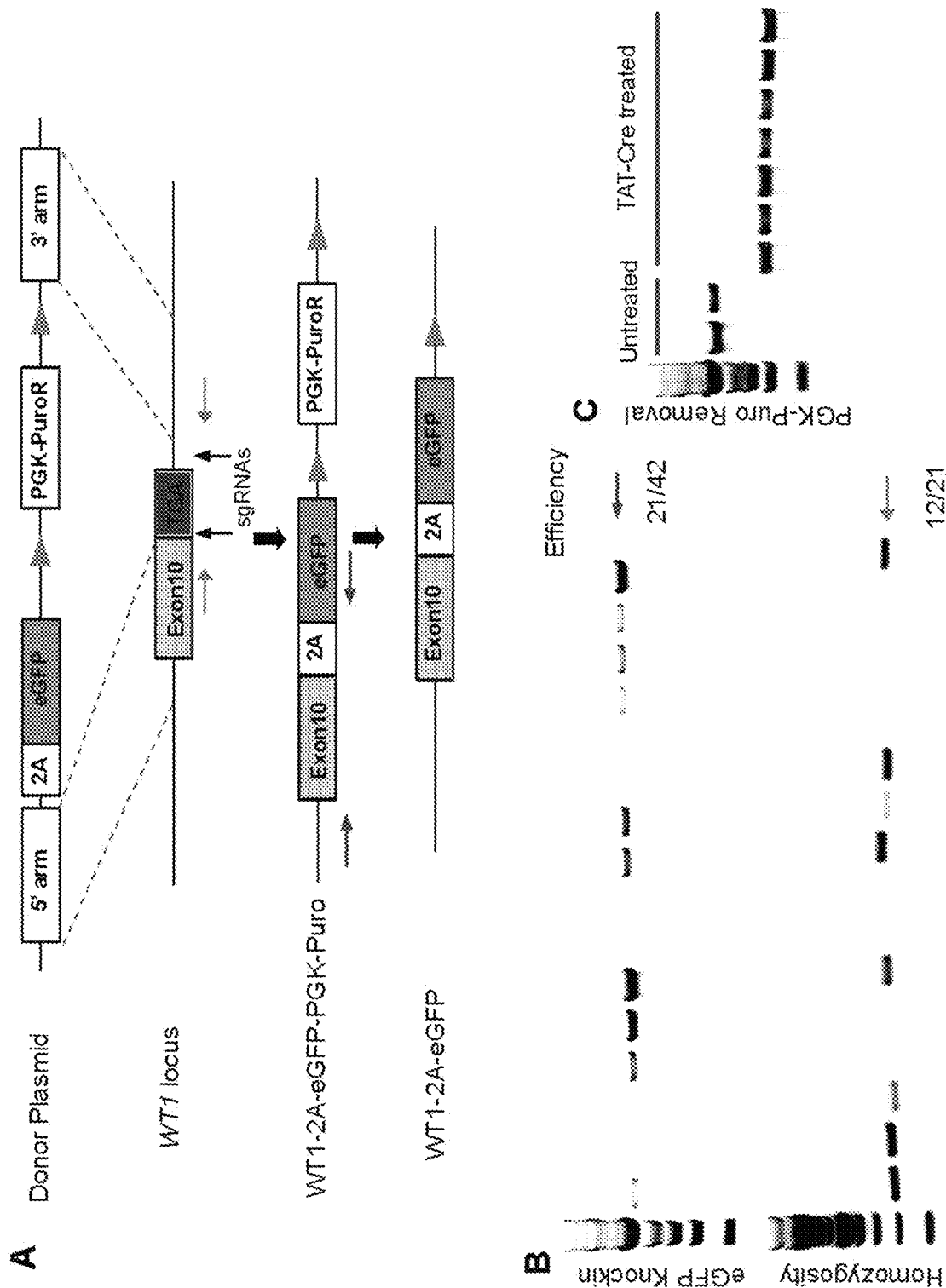
FIGS. 2A-2E (FIGS. 2A-2E) illustrate generation of WT1-2A-eGFP knock-in hPSC lines using Cas9 nuclease. (A) Schematic diagram of the targeting strategy at the stop codon of the WT1 locus. Vertical arrows indicate sgRNA1 and sgRNA2 targeting sites. Red and blue horizontal arrows indicate PCR genotyping primers for assaying WT1 locus targeting and homozygosity, respectively. (B) PCR genotyping of hESC clones after puromycin selection and the expected PCR product for correctly targeted WT1 locus is ~3 kbp (red arrows) with an efficiency of 21/44. Correctly targeted clones underwent a further homozygosity assay. Clones with the PCR products of about 200 bp are heterozygous (blue arrow), and those clones without PCR products are homozygous. (C) PCR genotyping of hESC clones after TAT-Cre mediated excision of the PGK-Puro cassette. Clones with the PCR products of about 1 kbp are PGK-Puro free, and those with ~3 kbp contain PGK-Puro. (D) Live cell flow analysis of GFP+ cells at day 0, day 10 and day 12 during CHIR treatment of WT1-2A-eGFP knock-in ES03. (E) Phase contrast images and corresponding eGFP fluorescent images of WT1-2A-eGFP hPSC-derived epicardial cells after excision of the PGK-Puro cassette. Scale bars, 100 μm.

Homozygous WT1-2A-eGFP Knock-in Reporter hPSCs Via CRISRP/Cas9 Recapitulate the Epicardial Cell Differentiation Process WT1 is required for the development of epicardium[42] and the formation of cardiovascular progenitor cells[43]. In order to better monitor the epicardial cell differentiation process and purify hPSC-derived epicardial cells in vitro, we engineered the ES03 human embryonic stem cell line via CRISPR/Cas9-catalyzed homology-directed repair (HDR) and generated a homozygous WT1-2A-eGFP knock-in reporter cell line (FIG. 2A). Two 2-kilobase homologous arm sequences located right before and after WT1 stop codon were inserted into the Oct4-2A-eGFP donor plasmid[44] and replaced the Oct4 homologous arms. We then introduced the 2A-eGFP sequence into the targeting sites by transfecting hESCs with the WT1-2A-eGFP donor plasmid and the Cas9/sgRNA plasmids. After puromycin selection, PCR genotyping and sequencing showed that ~50% (21/44) of the clones were targeted in one (heterozygous) and ~25% (12/44) both alleles (FIG. 2B). The homozygous clones were then subjected to TAT-Cre recombinase treatment and the PGK-Puro cassette was excised from WT1-2A-eGFP (FIG. 2C). WT1-2A-eGFP-targeted hPSCs after Cre-mediated excision of the PGK-Puro cassette were subjected for CHIR treatment with eGFP detected at day 10 and boosted at day 12 (FIG. 2D). Dual immunostaining of WT1 and GFP antibody resulted in expression of eGFP in WT1+ cells (FIG. 2E), demonstrating the success in generating WT1 reporter cell line for potential cell tracking or purification.

Chemically Defined Albumin Free Conditions to Generate WT1+ Epicardial Cells

We next optimized the concentration of CHIR and initial seeding density of cardiac progenitors at day 6 in LaSR basal medium, and found that 3 µM CHIR with an initial density of 0.06 million cells per $cm^2$ yielded more than 95% WT1+ cells (FIGS. 3A-D), while 0 µM CHIR resulted in less than 10% WT1-eGFP. However, LaSR basal medium, which contains bovine serum albumin, adds xenogenic components to the medium which would not be suitable for the generation of epicardial cells that meet clinical requirements. In order to develop a xeno-free protocol, we systematically screened 4 commercially available basal media supplemented with 1 μg/mL human recombinant insulin and 100 μg/mL ascorbic acid (Vc) as these two factors were shown to improve the culture of cardiac cell lineages[45-47]. DMEM, DMEM/F12 and RPMI generated more than 95% WT1+ putative epicardial cells from hPSC-derived cardiac progenitors (FIG. 3E). To simplify the differentiation pipeline, we employed RPMI as the basal medium, referring to epicardial cell generation from hPSCs as the "GiWiGi" (GSK3 inhibitor-WNT inhibitor-GSK3 inhibitor) protocol.

Epicardial Cell Differentiation from Cardiac Progenitors is β-Catenin Dependent

Figures 4A, 4B, 4C:
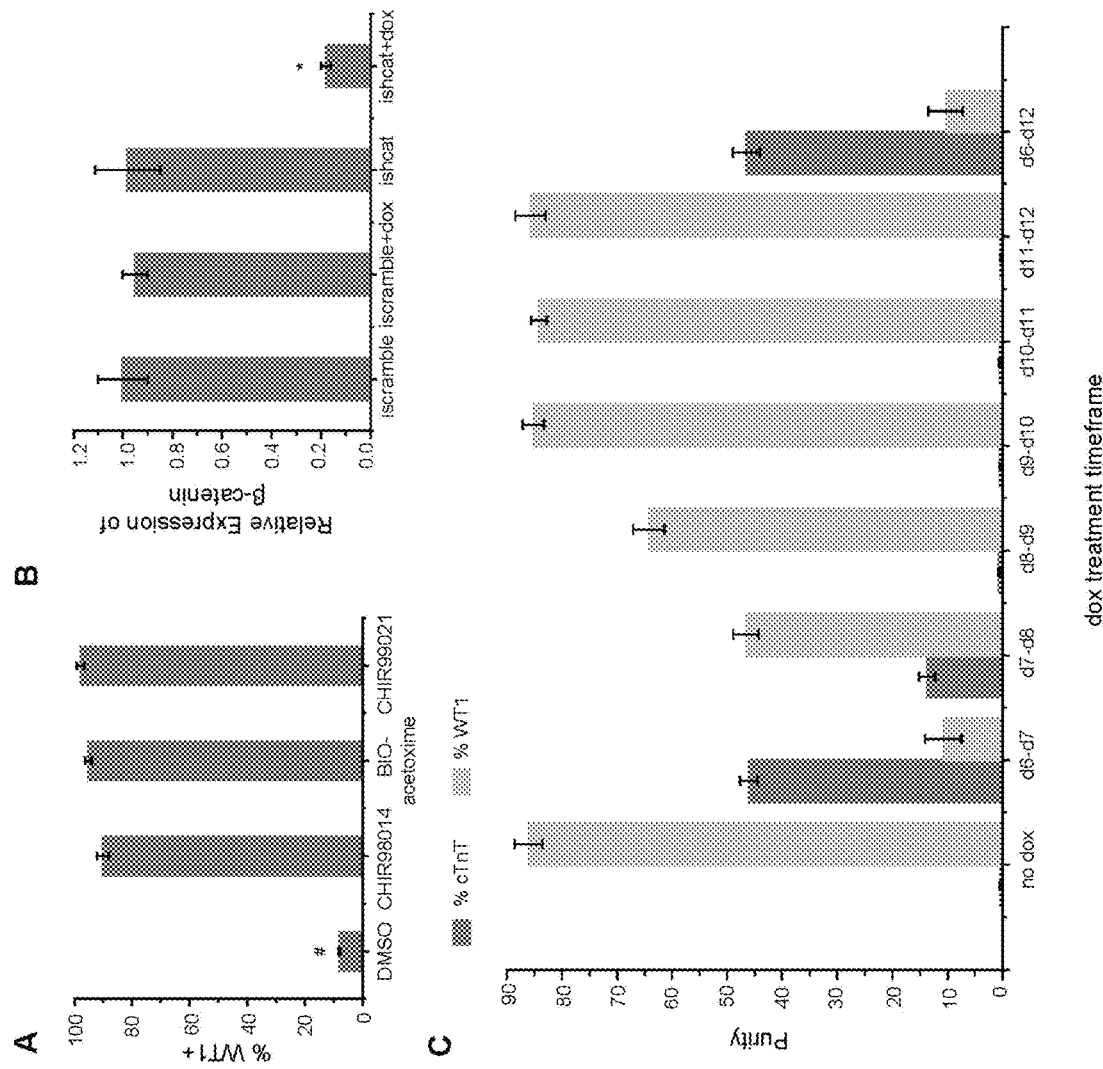
FIGS. 4A-4C (FIGS. 4A-4C) demonstrate β-catenin-dependent epicardial cell differentiation from hPSC-derived cardiac progenitors. (A) Day 6 H13 hESC-derived cardiac progenitor cells were seeded at a density of 0.06 million cells/cm$^2$, differentiated in LaSR basal medium with DMSO, 0.3 μM CHIR98014, 0.3 μM BIO-acetoxime or 3 μM CHIR99021 from day 7 to day 9, and subjected to flow cytometry analysis of WT1 expression at day 12. #p<0.005, DMSO versus CHIR98014, BIO-acetoxime, and CHIR99021; t test. (B) 19-9-11 iscramble and 19-9-11 ishcat-1 iPSCs were cultured in E8 medium with or without 2 μg/ml doxycycline (dox). After 3 days, mRNA was collected and CTNNB1 expression evaluated by qPCR. *p<0.005, ishcat-1 with dox versus ishcat-1 without dox or iscramble (w/o dox); t test. (C) 19-9-11 ishcat-1 iPSC-derived day 6 cardiac progenitor cells were differentiated as illustrated in FIG. 3A with 2 μg/ml doxycycline addition at the indicated times. At day 12, cells were analyzed for WT1+ and cTnT+ expression by flow cytometry. Data are represented as mean±SEM of at least three independent replicates.

Selectivity is a concern when using chemical inhibitors of signaling pathways. Therefore, we tested other GSK3 inhibitors including BIO-acetoxime and CHIR98014 in the GiWiGi protocol, and found that 0.3 μM CHIR98014 and BIO-acetoxime also induced WT1+ cell differentiation to a similar extent as 3 μM CHIR99021 (FIG. 4A). Although three small molecules, each with a distinct chemical structure, were used to decrease the likelihood of shared off-target effects, GSK3 inhibition itself may affect other signaling pathways. In order to evaluate the role of β-catenin in GSK3 inhibitor-induced epicardial differentiation, we generated an iPSC cell line (19-9-11 ischcat-1) expressing β-catenin shRNA under the control of a tet-regulated inducible promoter. Upon doxycycline (dox) treatment, the shRNA efficiently down-regulated β-catenin expression (FIG. 4B). Our previous work[15] showed that the induction of NKX2.5+ISL1+ cardiac progenitors from hPSCs is β-catenin dependent, therefore in this study we focused on the examination of the stage-specific roles of β-catenin during differentiation of epicardial cells from cardiac progenitors stimulated by GSK3 inhibition. We found that β-catenin knockdown at day 6 yielded significantly fewer WT1+ cells, instead generating robust beating sheets of cTnT+ cardiomyocytes at the expense of WT1+ cells (FIG. 4C and FIG. 11). This finding is consistent with reports that Wnt/β-catenin inhibition is necessary for cardiomyocyte formation from cardiac progenitors both in vitro and in vivo[15,25,48,49], and further supports the notion that Wnt/β-catenin signaling regulates epicardial vs. cardiomyocyte specification. The effects of β-catenin knockdown on decreasing WT1+ cell generation gradually diminished after day 6, with no inhibition after day 9 (FIG. 4C and FIG. 11).

Molecular Characterization of hPSC-Derived WT1+ Epicardial Cells

Pro-epicardial cells are marked by the expression of TBX18, WT1 and TCF21[30,50,51]. Molecular analysis of epicardial cell differentiation from hPSCs-derived cardiac progenitors (FIG. 5A and FIG. 12A) revealed dynamic changes in gene expression, with up-regulation of WT1 and TBX18, and undetectable TNNT2 (FIG. 5B). This was consistent with the WT1-eGFP signals (FIG. 2D), and was also confirmed by western blot analysis of WT1, TBX18 and TCF21 expression (FIG. 5C). Immunofluorescent analysis revealed expression of pro-epicardial markers WT1, TBX18, and TCF21 (FIGS. 5D-E). After passage at a low density, these cells adopted cobblestone-like appearance typical of cultured primary epicardium[28,52] (FIG. 5E). In addition, the cells displayed intense β-catenin and ZO1 localization at sites of cell-to-cell contact. Taken together, these data confirm the epithelial nature of these cells. These post-passaged cells also expressed aldehyde dehydrogenase enzyme retinaldehyde dehydrogenase 2 (ALDH1A2) (FIGS. 12-A-C), suggesting the ability to produce retinoic acids. Therefore, we refer to the day 12, pre-passaged WT1+ cells as pro-epicardial cells (Pro-Epi) and the post-passaged WT1+ cells as epicardial cells (Epi). The GiWiGi protocol was also effective in other hPSC lines, including human embryonic stem cell lines (hESC) H9 and ES03, and the 19-9-7 induced pluripotent stem cell (iPSC) line, generating more than 95% WT1+ cells (FIG. 13A). Post-passaged epicardial cells retained the expression of WT1 and displayed strong β-catenin and ZO1 staining along the cell borders (FIG. 13B).

Long-Term Expansion of hPSC-Derived WT1+ Epicardial Cells

Figures 6A, 6B, 6C, 6D:
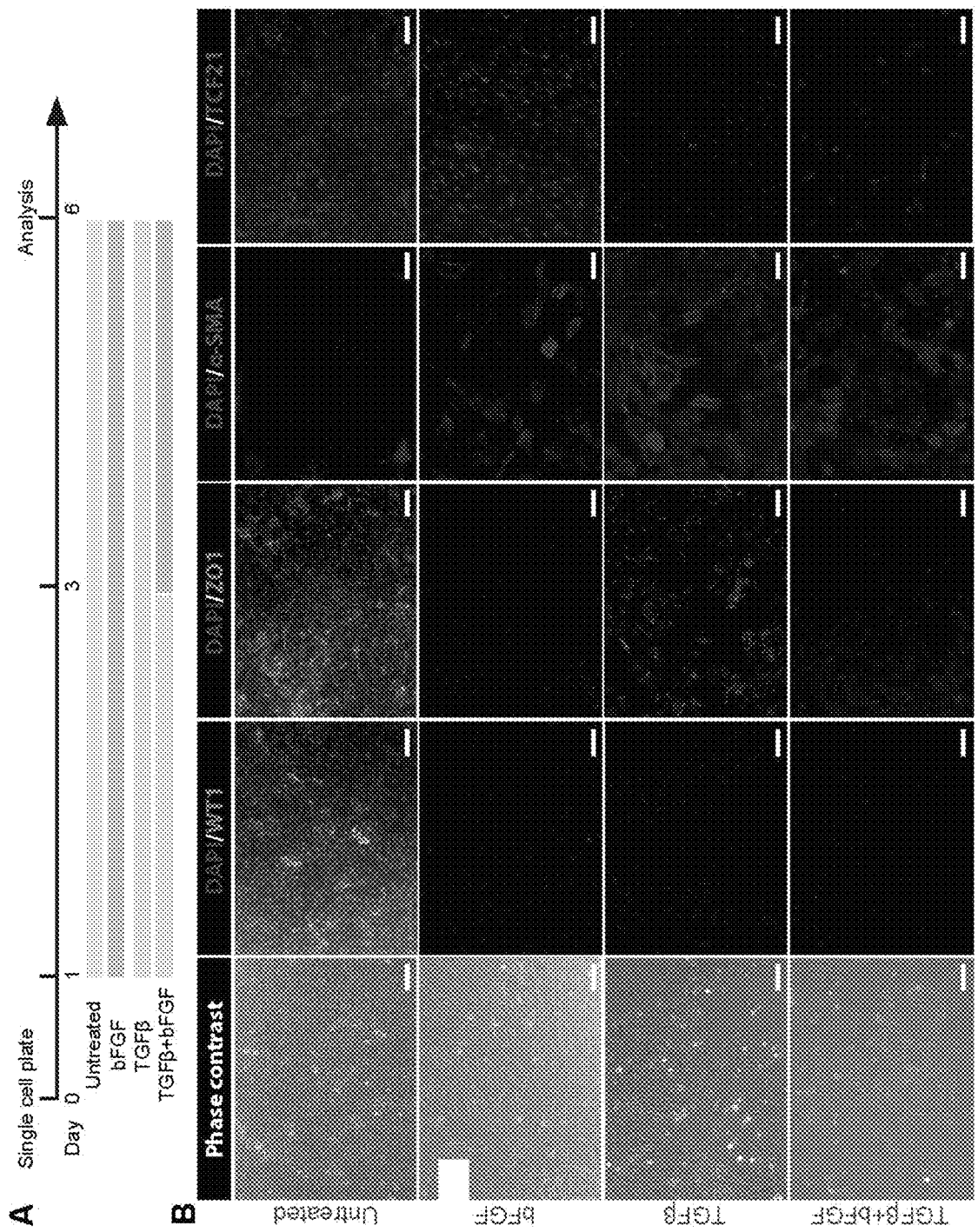
FIGS. 6A-6D (FIGS. 6A-6D) demonstrate that hPSC-derived epicardial cells undergo EMT in response to bFGF and TGFβ1 treatment, yielding epicardium-derived cells that display characteristics of fibroblasts and vascular smooth muscle cells. (A) Schematic of the protocols used for the EMT induction of H13 hESC-derived epicardial cells with 10 ng/mL bFGF and 5 ng/mL TGFβ1. (B) At day 18, phase contrast images displaying cell morphology and fluorescence images showing the presence of WT1, ZO1, α-SMA and TCF21 proteins in Epi-derived cultures. Scale bars, 100 μm. (C) qPCR analysis of EMT related genes SNAIL2, CDH2 and CDH1 and (D) immunostaining analysis of E-cadherin expression after the indicated bFGF and TGFβ1 treatments. Scale bars, 50 μm.

Primary mouse epicardial cells have been cultured for more than 3 years[50], but epicardial cells isolated from the adult human heart rapidly undergo EMT in culture[28]. Similar to primary human epicardial cells, hPSC-derived WT1+ epicardial cells only retained their morphology for approximately 2 weeks in culture. While in the short term, hPSC-derived WT1+ epicardial cells retained the epicardial cobblestone-like morphology, bFGF and TGFβ-treated cells adopted a fibroid spindle or fusiform-shaped appearance typical of cultured fibroblasts and smooth muscle cells, respectively (FIGS. 6A-B). The expression of calponin and smooth muscle myosin heavy chain (SMMHC) in TGFβ+ bFGF-induced cultures further support their smooth muscle cell identity, and vimentin (VIM) and CD90 expression support their fibroblast identity (FIG. 14). We also cultured WT1+TBX18+ epicardial cells in endothelial cell medium, but did not detect expression of endothelial markers CD31 and VE-cadherin (FIG. 14). The expression of WT1 and ZO1 significantly decreased in both bFGF and TGFβ-treated samples, indicating the transition from epithelial towards mesenchymal-like cells (FIG. 6B). In addition, CDH1 (E-cadherin) expression decreased whereas CDH2 (N-cadherin) and SNAIL2 expression increased in all the treated samples compared to the untreated controls, suggesting bFGF and TGFβ induced EMT in hPSC-derived epicardial cells (FIGS. 6C-D).

Figures 7A, 7B, 7C, 7D:
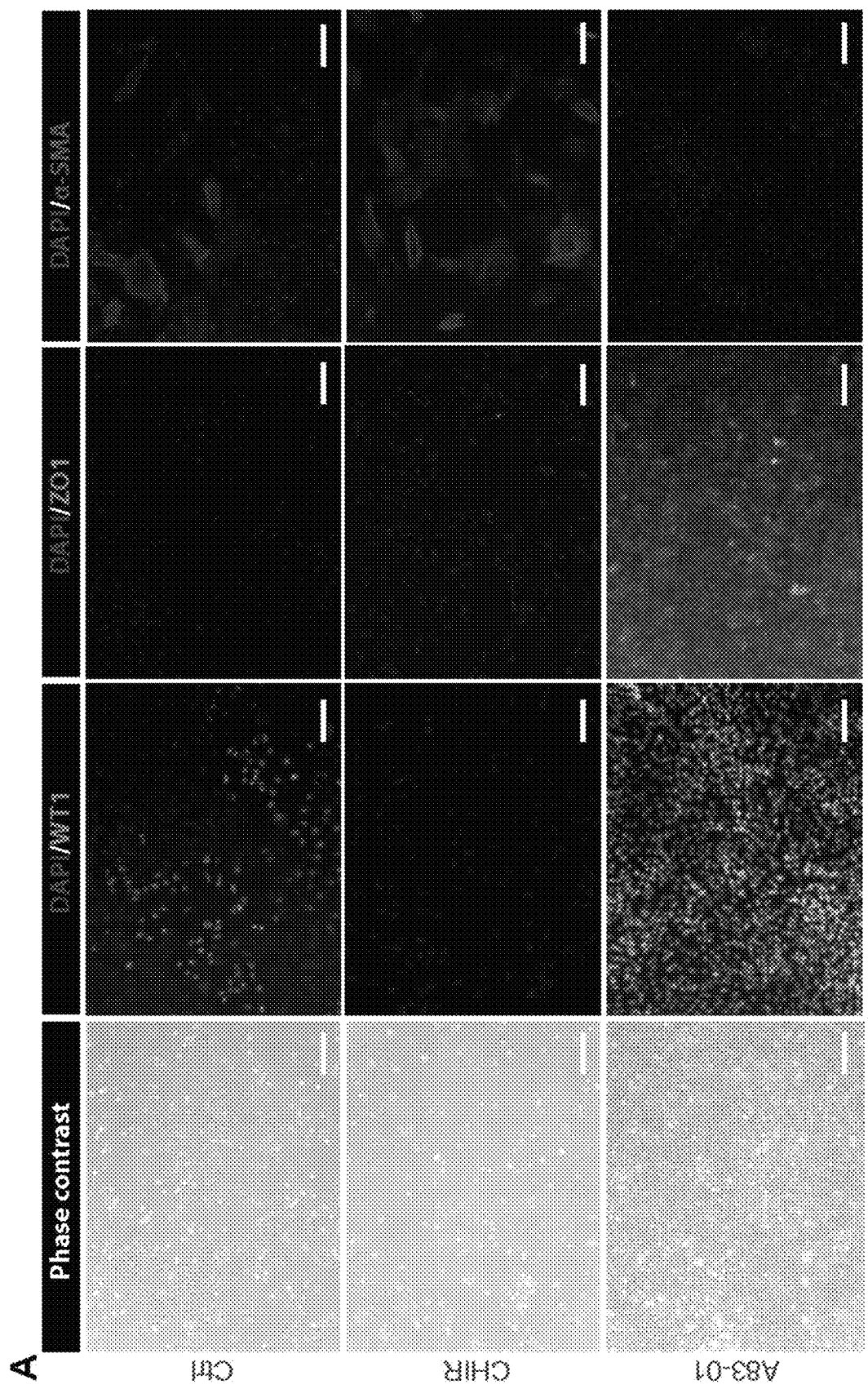
Figures 8A, 8B, 8C, 8D, 8E:
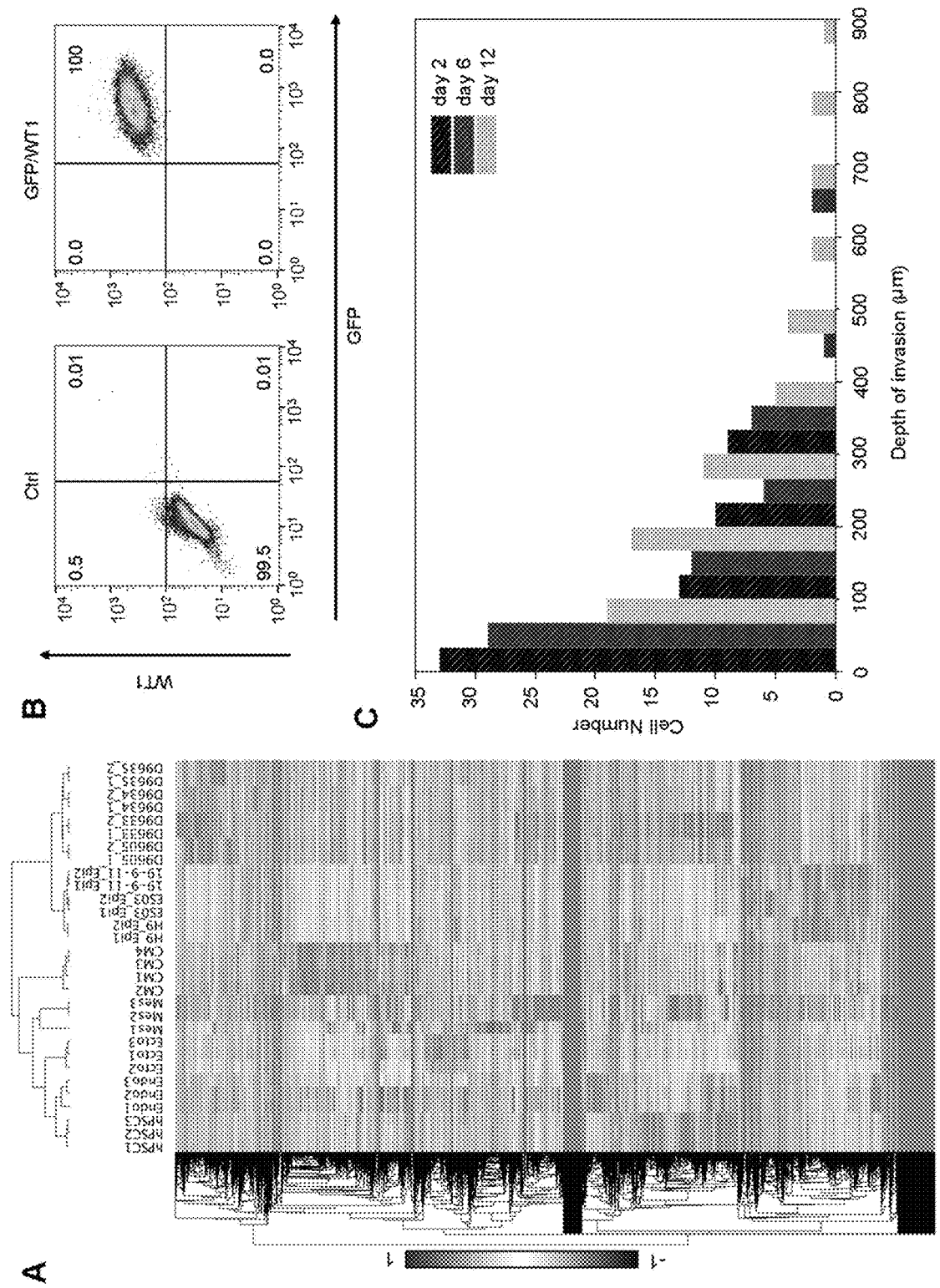
Figures 15A, 15B, 15C, 15D:
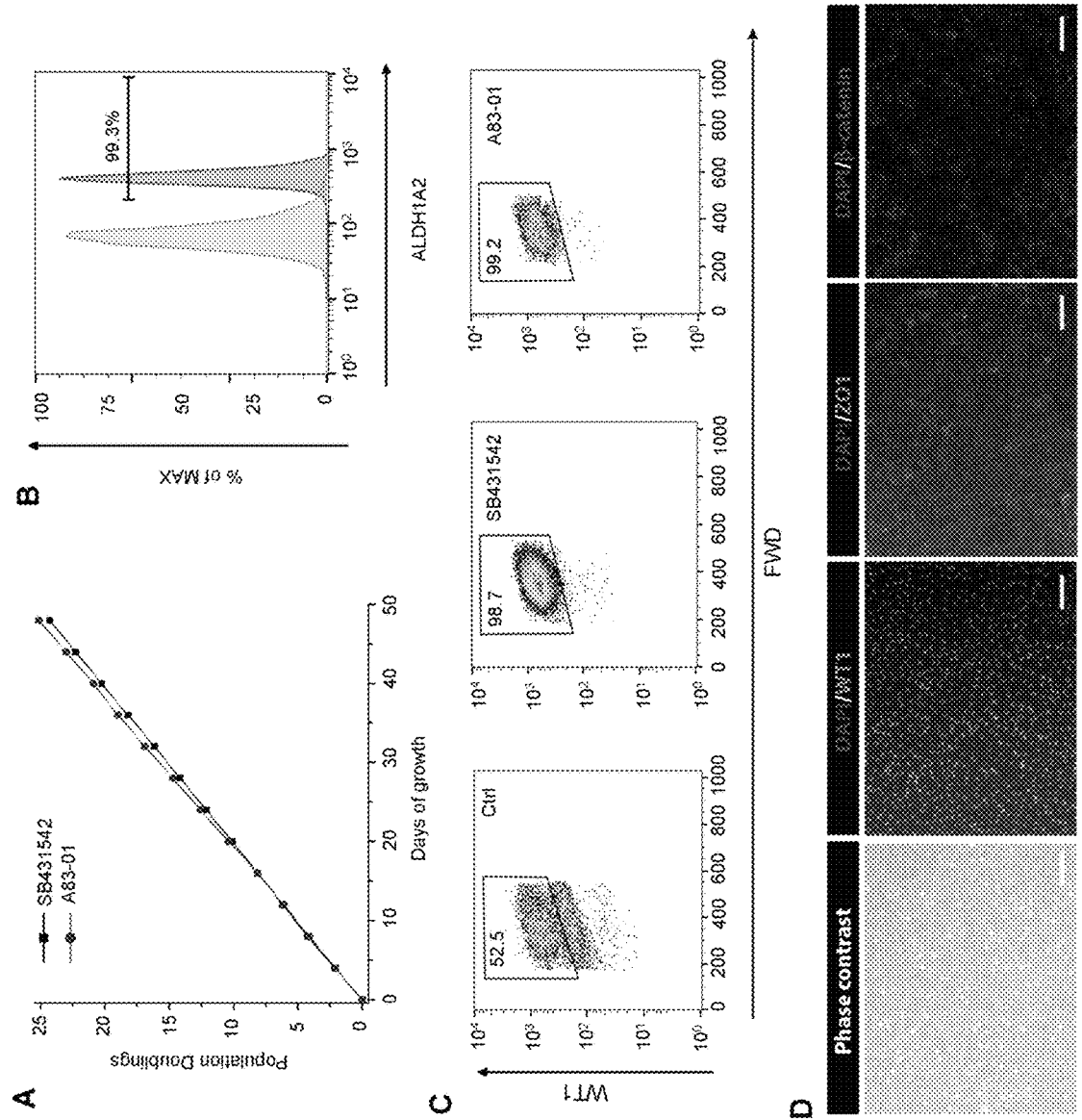
Figures 16A, 16B, 16C, 16D, 16E, 16F, 16G:
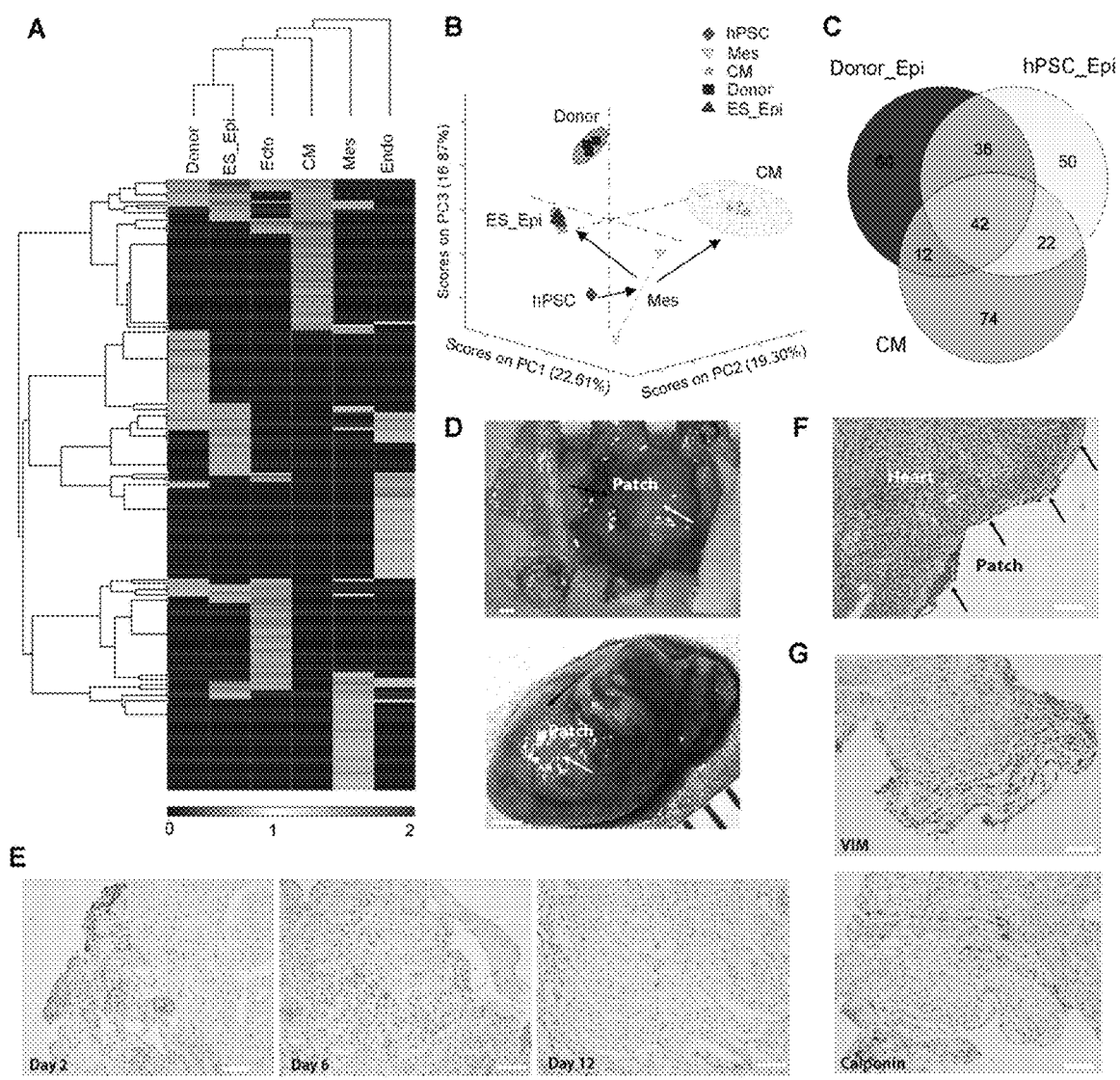

During long term in vitro culture hPSC-derived WT1+ epicardial cells spontaneously underwent EMT and lost WT1 expression after several passages, even without exogenous TGFβ or bFGF treatment (FIG. 7A). To identify signaling mechanisms regulating hPSC-derived epicardial cell self-renewal, we applied small molecules (Table 3) that affect pathways that regulate cell proliferation to study their effects on WT1+ cell self-renewal. A83-01, an inhibitor of TGFβ signaling, enabled expansion of hPSC-derived epicardial cells that retained polarized epithelial morphology and WT1 expression (FIGS. 7A-B). Upon A83-01 or SB431542 addition, hPSC-derived epicardial cells were capable of at least 25 population doublings, generating more than 10 million cells from a single hPSC-derived epicardial cell clone (FIG. 7C). After 48 days of expansion, the TGFβ inhibitor-treated cells expressed significantly higher levels of WT1 and Ki67, a proliferative marker, than the untreated cells (FIG. 7D). Epicardial cells generated from additional hPSC-lines were also expandable after A83-01 treatment (FIG. 15A), presenting a cobblestone morphology and expressing high levels of ALDH1A2, WT1, ZO1 and β-catenin (FIGS. 15B-D). These findings improve our understanding of self-renewal mechanisms of the epicardium and have implications for generating large quantities of hPSC-derived epicardial cells for research or cell-based therapy applications.

hPSC-Derived Epicardial Cells were Similar to Primary Epicardial Cells Both In Vitro and In Vivo To further confirm the identity of hPSC-derived epicardial cells, RNA from 3 different hPSC-derived epicardial cell differentiations and primary epicardial cells of 4 different donors were subjected to RNA-seq analysis. FIG. 8A presents hierarchical clustering analysis of RNA-seq expression data of hPSCs[34-36], hPSC-derived endoderm (Endo)[34], hPSC-derived ectoderm (Ecto)[35], hPSC-derived mesoderm (Mes) (GSM1112833, 915324, 915325), CMs[37], epicardial cells (Epi) derived from human stem cell lines H9, ES03, and 19-9-11, and primary epicardial cells. The hierarchical clustering analysis showed that hPSC-derived epicardial cells were most closely related to primary epicardial cells and were distinct from all other cell populations together as a group. Next we explored the relationship between different cell types relevant for development including hPSC, mesoderm, cardiomyocytes, and epicardial cells, using principal component analysis (PCA) on the gene expression data. The 3D scores plot for the first 3 principal components shows a trend of hPSCs clustering relatively closer to mesoderm cells, from which epicardial cells and CMs divergently formed (FIG. 16A). Importantly, hPSC-derived epicardial cells showed highest similarity with donor epicardial cells. We also performed gene set enrichment analysis (GSEA) to identify significantly enriched pathways (p<0.05) in each cell type in relative to hPSCs. Hierarchical clustering of the absolute value of normalized enrichment score (NES) of these pathways confirmed the similarity between epicardial cells from hPSCs and those from donors (FIG. 16B). As both epicardial cells and CMs are derived from mesoderm, we further compare the differences and similarities in the enriched pathways among these cell types. We observed that while 42 pathways were commonly enriched in all cell types, hPSC-derived epicardial cells shared 36 pathways with donor epicardial cells, and 22 with cardiomyocytes (FIG. 16C) (Tables 4-6). Microarray data analysis has shown the enrichment of cell adhesion and extracellular matrix organization genes in mouse primary epicardial cells[53]. Similarly, our hPSC-derived or donor epicardial cells also showed enrichment in extracellular matrix related pathways and keratinocyte (epithelial) differentiation, while CMs were enriched in heart development and heart contraction related pathways as expected. Importantly, donor epicardial cells were highly enriched in endoplasmic reticulum related pathways compared to hPSC-derived epicardial cells, likely indicating the maturation status of epicardial cells.

Epicardial cells can undergo EMT and give rise to cardiac fibroblasts and smooth muscle cells after transplantation into chicken embryos[26] or infarcted mouse hearts[28]. To examine the ability of hPSC-derived epicardial cells to invade the myocardium and undergo EMT in vivo, cardiac fibroblast-derived extracellular matrix (CF-ECM) patches seeded with eGFP-labeled hPSC-derived epicardial cells (FIG. 8B) were transferred to the heart surface (FIG. 16D) of a mouse myocardial infarction (MI) model. eGFP+ cells were detected predominantly within the CF-ECM scaffold and in the epicardium beneath the scaffold before day 6, and scattered within the mid-myocardium after 12 days (FIG. 8D and FIG. 16E), suggesting epicardial cells invaded the myocardium. Even after 12 days, the scaffold remained adherent (FIG. 16F). In addition, the hPSC-derived cells underwent EMT and differentiated into SMA+calponin+ smooth muscle-like cells (FIG. 8D and FIG. 16G) and VIM+ fibroblast-like cells in vivo. These findings demonstrate that hPSC-derived epicardial cells can invade the myocardium and form EPDCs after infarction, underscoring their potential for cell-based therapeutic heart regeneration.

DISCUSSION

Here, we report for the first time the generation of a WT1-2A-eGFP knockin stem cell line, and demonstrates efficient and robust generation of epicardial cells from multiple hPSC lines solely via stage-specific manipulation of Wnt/β-catenin signaling under chemically-defined, albumin-free, animal component-free conditions. These hPSC-derived epicardial cells retain many characteristics of primary epicardial cells, including formation of an epithelial sheet, expression of key epicardial proteins WT1, TBX18, and ALDH1A2, and the ability to generate fibroblast and vascular smooth muscle lineages both in vitro and in vivo. In addition, their identity was further confirmed by RNA-seq expression data and gene set enrichment analysis (GSEA) at a global level. Using inducible knockdown hPSC lines, we showed that β-catenin is essential for epicardial cell induction from hPSC-derived cardiac progenitors during the GiWiGi protocol. Given the essential roles of β-catenin during cardiac progenitor induction from hPSCs[15], we conclude that β-catenin is required at multiple stages of hPSC differentiation to epicardial cells via small molecule modulation of canonical Wnt signaling.

This study also demonstrates long-term self-renewal of hPSC-derived epicardial cells via TGFβ-inhibition in a chemically-defined medium. For cell-based therapeutic applications, it is highly desirable to generate homogeneous committed progenitors that can expand in culture and differentiate into various tissue-specific cells of interest, avoiding the contamination of unwanted cell lineages, especially tumorigenic hPSCs[54]. We showed that inhibition of TGFβ signaling is sufficient for the self-renewal of hPSC-derived epicardial cells, in contrast to primary mouse epicardial cells which can self-renew in the absence of a TGFβ inhibitor[50]. Recent work has demonstrated that epicardial cell lineages improved the performance of the scarred myocardium by preservation of cardiac function and attenuation of ventricular remodeling after transplantation into a MI model[55]. More recently, Wang et al. identified a requirement for the epicardium of the zebrafish heart for muscle regeneration, and showed that ventricular epicardium was stimulated to regenerate upon Sonic hedgehog (Shh) treatment[56]. Our results suggest that TGFβ inhibitors may impact heart regeneration following injection into the epicardium in vivo, similar to strategy used to test the effect of TGFβ inhibitors on scar formation after glaucoma surgery in rabbits[57].

In summary, our findings support a model (FIG. 8E) of human epicardial development in which small molecule-mediated exogenous modulation of Wnt/β-catenin signaling is sufficient for the specification of epicardial cells from hPSCs. This finding is consistent with the report that DKK1 and DKK2 double null mice increase epicardial specification and display a hypercellular epicardium[27]. This completely defined, xeno-free epicardial differentiation platform can be employed to efficiently derive self-renewing epicardial cell lineages from hPSCs, which can thereby provide insights into mechanisms of heart development, maturation, and response to cardiac injury. Moreover, we show that hPSC-derived epicardial cells can invade the myocardium in an infarcted mouse model, suggesting potential applications in cell-based heart regeneration. Our results also point to TGFβ signaling as a regulator of epicardial cell self-renewal and differentiation, indicating the potential of TGFβ signaling modulators in heart regeneration.

TABLE 1

Antibodies

| Antibody | Source/Isotype/clone/cat. no. | Concentration |
|---|---|---|
| Smooth muscle actin | Lab Vision/Mouse IgG2a/1A4/ms-133-p | 1:100 (IS) |
| Cardiac troponin T | Lab Vision/Mouse IgG1/13-11/ms-295-p1 | 1:200 (FC & IS) |
| ISL1 | DSHB/Mouse IgG2b/39.4D5-s | 1:20 (IS) |
| NKX2.5 | Santa Cruz/Rabbit IgG/sc-14033/H-114 | 1:100 (IS) |
| Flk-1 | Santa Cruz/Mouse IgG1/sc-6251/A-3 | 1:200 (IS) |
| Ki67 | BD Biosciences/Mouse IgG1/550609 | 1:100 (IS) |
| WT1 | Abcam/Rabbit IgG/ab89901 | 1:250 (FC & IS) |
| TCF21 | Sigma-Aldrich/Rabbit IgG/HPA013189 | 1:200 (IS) |
| TBX18 | Sigma-Aldrich/Rabbit IgG/HPA029014 | 1:200 (IS) |
| ALDH1A2 | Sigma-Aldrich/Rabbit IgG/HPA010022 | 1:50 (IS) |
| ZO1 | Invitrogen/Rabbit IgG/402200 | 1:200 (IS) |
| β-catenin | Cell Signaling/Mouse IgG1/2698/L87A12 | 1:200 (IS) |
| Vimentin (no cross reaction with mouse) | Sigma-Aldrich/Mouse IgG1/V6630/V9 | 1:200 (IS) |
| VE-cadherin | Santa Cruz/Mouse IgG1/F-8/sc9989 | 1:100 (IS) |
| CD31 | ThermoFisher/Rabbit IgG/RB-10333-P | 1:100 (IS) |
| CD90 | BD Pharmingen/Mouse IgG1/559869 | 1:200 (IS) |
| E-cadherin | BD Biosciences/Mouse IgG2a/560061 | 1:200 (IS) |
| SMMHC | Abcam/Rabbit IgG/ab82541 | 1:800 (IS) |
| Calponin (no cross reaction with mouse) | Abcam/Mouse IgG1/ab700/CALP | 1:200 (IS) |
| GFP | DSHB/Mouse IgG1/12E6 | 1:20 (IS) |
| Mitochondria (human specific) | Millipore/Mouse IgG1/113-1/MAB1273 | 1:100 (IS) |
| β-actin | Cell Signaling/Rabbit mAb(HRP Conjugate)/5152S/13E5 | 1:5,000(WB) |
| Secondary Antibody | Alexa 488 Chicken anti-Gt IgG/A-21467 | 1:1,000 |
| Secondary Antibody | Alexa 488 Chicken anti-Rb IgG/A-21441 | 1:1,000 |
| Secondary Antibody | Alexa 488 Goat anti-Ms IgG1/A-21121 | 1:1,000 |
| Secondary Antibody | Alexa 488 Goat anti-Rb IgG/A-11008 | 1:1,000 |
| Secondary Antibody | Alexa 594 Goat anti-Ms IgG2b/A-21145 | 1:1,000 |
| Secondary Antibody | Alexa 594 Goat anti-Rb IgG/A-11012 | 1:1,000 |
| Secondary Antibody | Alexa 647 Goat anti-Ms IgG2b/A-21242 | 1:1,000 |
| Secondary Antibody | Alexa 647 Goat anti-Rb IgG/A-21244 | 1:1,000 |

TABLE 2

Oligonucleotide Primers

| Genes | Sequences (5' - 3') | Size (bp)/ Tm (° C.) |
|---|---|---|
| OCT4 | F: CAGTGCCCGAAACCCACAC (SEQ ID NO: 5) <br> R: GGAGACCCAGCAGCCTCAAA (SEQ ID NO: 6) | 161/58 |
| NANOG | F: CGAAGAATAGCAATGGTGTGACG (SEQ ID NO: 7) <br> R: TTCCAAAGCAGCCTCCAAGTC (SEQ ID NO: 8) | 328/58 |
| T | F: AAGAAGGAAATGCAGCCTCA (SEQ ID NO: 9) <br> R: TACTGCAGGTGTGAGCAAGG (SEQ ID NO: 10) | 101/58 |
| ISL1 | F: CACAAGCGTCTCGGGATT (SEQ ID NO: 11) <br> R: AGTGGCAAGTCTTCCGACA (SEQ ID NO: 12) | 202/58 |
| FLK-1 | F: GTGACCAACATGGAGTCGTG (SEQ ID NO: 13) <br> R: TGCTTCACAGAAGACCATGC (SEQ ID NO: 14) | 218/60 |
| NKX2.5 | F: GCGATTATGCAGCGTGCAATGAGT (SEQ ID NO: 15) <br> R: AACATAAATACGGGTGGGTGCGTG (SEQ ID NO: 16) | 220/58 |
| TNNT2 | F: TTCACCAAAGATCTGCTCCTCGCT (SEQ ID NO: 17) <br> R: TTATTACTGGTGTGGAGTGGGTGTGG (SEQ ID NO: 18) | 165/58 |
| TBX18 | F: CCCAGGACTCCCTCCTATGT (SEQ ID NO: 19) <br> R: TAGGAACCCTGATGGGTCTG (SEQ ID NO: 20) | 200/59 |
| WT1 | F: CAGCTTGAATGCATGACCTG (SEQ ID NO: 21) <br> R: GATGCCGACCGTACAAGAGT (SEQ ID NO: 22) | 200/60 |
| TCF21 | F: ACCCTCTTCCTCGCTTTCTC (SEQ ID NO: 23) <br> R: TGCTCTCGTTGGAAGTCACA (SEQ ID NO: 24) | 180/59 |
| ALDH1A2 | F: CTCCTCTGTCACACCCCATT (SEQ ID NO: 25) <br> R: TTGACAGCTGGAAAGATGGA (SEQ ID NO: 26) | 198/59 |
| SNAI2 | F: ACAGAGCATTTGCAGACAGG (SEQ ID NO: 27) <br> R: GTGCTACACAGCAGCCAGAT (SEQ ID NO: 28) | 147/59 |

TABLE 2-continued

Oligonucleotide Primers

| Genes | Sequences (5' - 3') | Size (bp)/ Tm (° C.) |
|---|---|---|
| CDH1 | F: TTCTGCTGCTCTTGCTGTTT (SEQ ID NO: 29)<br>R: TGGCTCAAGTCAAAGTCCTG (SEQ ID NO: 30) | 142/59 |
| CDH2 | F: CTCCAATCAACTTGCCAGAA (SEQ ID NO: 31)<br>R: ATACCAGTTGGAGGCTGGTC (SEQ ID NO: 32) | 136/58 |
| CTNNB1 | F: GAATGAGACTGCTGATCTTGGAC (SEQ ID NO: 33)<br>R: CTGATTGCTGTCACCTGGAG (SEQ ID NO: 34) | 250/58 |
| GAPDH | F: GTGGACCTGACCTGCCGTCT (SEQ ID NO: 35)<br>R: GGAGGAGTGGGTGTCGCTGT (SEQ ID NO: 36) | 152/58 |
| WT1 KI (Red) | F: GGTCTTGGTTTCTGCTGGAC (SEQ ID NO: 37)<br>R: AAGTCGTGCTGCTTCATGTG (SEQ ID NO: 38) | 2777/60 |
| WT1 KI (Blue) | F: TGAAAAGCCCTTCAGCTGTC (SEQ ID NO: 39)<br>R: TGAGGAGGAGTGGAGAGTCAG (SEQ ID NO: 40) | 204 or 2847/60 |

TABLE 3

Signaling Modulators

| Modulator | Targeted pathway | Concentration |
|---|---|---|
| bFGF | FGF | 10 ng/mL |
| BMP4 | BMP | 10 ng/mL |
| Dorsomorphin (DM) | BMP | 4 µM |
| IWP2 | Wnt | 5 µM |
| CHIR99021 (CHIR) | Wnt | 1~9 µM |
| CHIR98014 | Wnt | 0.3 µM |
| BIO-acetoxime | Wnt | 0.3 µM |
| Purmorphamine (PURM) | Hedgehog | 2 µM |
| Retinoic acid (RA) | RA | 2 µM |
| PD0325901 (PD) | MEK | 0.5 µM |
| Verteporfin (VP) | Hippo pathway | 1 µM |
| RO4929097 (RO) | Notch | 2 µM |
| TGFβ1 | TGFβ | 5 ng/mL |
| A83-01 | TGFβ | 0.5 µM |
| SB431542 | TGFβ | 2 µM |

TABLE 4

Top 15 Gene Annotations enriched in donor epicardial cells compared to hPSCs

| GO Description | NES | p-value |
|---|---|---|
| Positive regulation of I-kappaB kinase NF kappaB cascade | 2.068 | 0 |
| Regulation of I-kappaB NF kappaB cascade | 1.983 | 0 |
| Endoplasmic reticulum part | 1.900 | 0 |
| Endoplasmic reticulum membrane | 1.810 | 0 |
| I-kappaB kinase NF kappaB cascade | 1.804 | 0 |
| Intrinsic to organelle membrane | 1.803 | 0 |
| Positive regulation of signal transduction | 1.800 | 0 |
| ER to golgi vesicle mediated transport | 1.787 | 0.009 |
| Extracellular matrix part | 1.782 | 0 |
| Keratinocyte differentiation | 1.768 | 0.020 |
| Hematopoietin interferon class D200 domain cytokine receptor binding | 1.765 | 0 |
| Integral to endoplasmic reticulum membrane | 1.765 | 0.016 |
| ER golgi intermediate compartment | 1.763 | 0.005 |
| Integral to organelle membrane | 1.759 | 0 |

* NES: normalized enrichment score. P-value of 0 means <0.0001.

TABLE 5

Top 15 Gene Annotations enriched in hPSC-derived epicardial cells compared to hPSCs

| GO Description | Number of genes | p-value |
|---|---|---|
| Sulfuric ester hydrolase activity | 1.776 | 0.004 |
| Extracellular matrix | 1.760 | 0 |
| Proteinaceous extracellular matrix | 1.751 | 0 |
| Extracellular matrix part | 1.727 | 0.002 |
| Muscle development | 1.709 | 0 |
| Negative regulation of cell cycle | 1.695 | 0.002 |
| Collagen | 1.668 | 0.0052 |
| Cell cycle arrest GO 0007050 | 1.662 | 0.0032 |
| Muscle cell differentiation | 1.649 | 0.011 |
| Skeletal development | 1.637 | 0 |
| Skeletal muscle development | 1.604 | 0.008 |
| Keratinocyte differentiation | 1.600 | 0.009 |
| Myoblast differentiation | 1.594 | 0.010 |
| Striated muscle development | 1.576 | 0.010 |

* NES: normalized enrichment score. P-value of 0 means <0.0001.

TABLE 6

Top 15 Gene Annotations enriched in hPSC-derived cardiomyocytes (CMs) compared to hPSCs

| GO Description | NES | p-value |
|---|---|---|
| Regulation of heart contraction | 2.070 | 0.000 |
| Structural constituent of muscle | 1.971 | 0.000 |
| Muscle development | 1.890 | 0.000 |
| Mitochondrial membrane part | 1.842 | 0.000 |
| Myosin complex | 1.832 | 0.000 |
| Growth factor activity | 1.819 | 0.002 |
| Mitochondrial membrane | 1.817 | 0.000 |
| Energy derivation by oxidation of organic compounds | 1.803 | 0.000 |
| Heart development | 1.781 | 0.000 |
| Mitochondrial inner membrane | 1.774 | 0.000 |
| Mitochondrial respiratory chain | 1.758 | 0.000 |
| Mitochondrial envelope | 1.739 | 0.000 |
| Contractile fiber part | 1.696 | 0.002 |
| Generation of precursor metabolites and energy | 1.665 | 0.000 |

* NES: normalized enrichment score. P-value of 0 means <0.0001.

REFERENCES

All publications, including but not limited to patents and patent applications, cited below are herein incorporated by reference as though set forth in their entirety in the present application.

1. Brade, T., Pane, L. S., Moretti, A., Chien, K. R. & Laugwitz, K.-L. Embryonic heart progenitors and cardiogenesis. *Cold Spring Harb. Perspect. Med.* 3, a013847 (2013).
2. Männer, J. & Ruiz-Lozano, P. Development and Function of the Epicardium. *Advances in Developmental Biology* 18, 333-357 (2007).

3. Riley, P. R. An Epicardial Floor Plan for Building and Rebuilding the Mammalian Heart. *Curr. Top. Dev. Biol.* 100, 233-251 (2012).
4. Pérez-Pomares, J.-M. et al. Origin of coronary endothelial cells from epicardial mesothelium in avian embryos. *Int. J. Dev. Biol.* 46, 1005-13 (2002).
5. Smart, N. et al. Thymosin beta4 induces adult epicardial progenitor mobilization and neovascularization. *Nature* 445, 177-82 (2007).
6. Zhou, B. et al. Adult mouse epicardium modulates myocardial injury by secreting paracrine factors. *J. Clin. Invest.* 121, 1894-1904 (2011).
7. Zhou, B. & Pu, W. T. Epicardial epithelial to mesenchymal transition in injured heart. *J. Cell. Mol. Med.* 15, 2781-2783 (2012).
8. Kikuchi, K. et al. Retinoic Acid Production by Endocardium and Epicardium Is an Injury Response Essential for Zebrafish Heart Regeneration. *Dev. Cell* 20, 397-404 (2011).
9. Lepilina, A. et al. A Dynamic Epicardial Injury Response Supports Progenitor Cell Activity during Zebrafish Heart Regeneration. *Cell* 127, 607-619 (2006).
10. Zhou, B. et al. Epicardial progenitors contribute to the cardiomyocyte lineage in the developing heart. *Nature* 454, 109-13 (2008).
11. Thomson, J. A. Embryonic Stem Cell Lines Derived from Human Blastocysts. *Science* 282, 1145-1147 (1998).
12. Murry, C. E. & Keller, G. Differentiation of embryonic stem cells to clinically relevant populations: lessons from embryonic development. *Cell* 132, 661-80 (2008).
13. Ashton, R. S., Keung, A. J., Peltier, J. & Schaffer, D. V. Progress and prospects for stem cell engineering. *Annu. Rev. Chem. Biomol. Eng.* 2, 479-502 (2011).
14. Kattman, S. J. et al. Stage-specific optimization of activin/nodal and BMP signaling promotes cardiac differentiation of mouse and human pluripotent stem cell lines. *Cell Stem Cell* 8, 228-40 (2011).
15. Lian, X. J. et al. Robust cardiomyocyte differentiation from human pluripotent stem cells via temporal modulation of canonical Wnt signaling. *Proc. Natl. Acad. Sci. U.S.A* 109, E1848-E1857 (2012).
16. Lian, X. et al. Directed cardiomyocyte differentiation from human pluripotent stem cells by modulating Wnt/β-catenin signaling under fully defined conditions. *Nat. Protoc.* 8, 162-75 (2013).
17. Minami, I. et al. A small molecule that promotes cardiac differentiation of human pluripotent stem cells under defined, cytokine- and xeno-free conditions. *Cell Rep.* 2, 1448-60 (2012).
18. Bao, X. et al. Chemically-defined albumin-free differentiation of human pluripotent stem cells to endothelial progenitor cells. *Stem Cell Res.* 15, 122-129 (2015).
19. Lian, X. et al. Efficient Differentiation of Human Pluripotent Stem Cells to Endothelial Progenitors via Small-Molecule Activation of WNT Signaling. *Stem Cell Reports* 3, 804-16 (2014).
20. Sahara, M. et al. Manipulation of a VEGF-Notch signaling circuit drives formation of functional vascular endothelial progenitors from human pluripotent stem cells. *Cell Res.* 24, 820-41 (2014).
21. Samuel, R. et al. Generation of functionally competent and durable engineered blood vessels from human induced pluripotent stem cells. *Proc. Natl. Acad. Sci. U.S.A* 110, 12774-9 (2013).
22. Wang, A. et al. Derivation of Smooth Muscle Cells with Neural Crest Origin from Human Induced Pluripotent Stem Cells. *Cells Tissues Organs* 195, 5-14 (2012).
23. Wang, Y. et al. Engineering vascular tissue with functional smooth muscle cells derived from human iPS cells and nanofibrous scaffolds. *Biomaterials* 35, 8960-8969 (2014).
24. Cheung, C., Bernardo, A. S., Trotter, M. W. B., Pedersen, R. A. & Sinha, S. Generation of human vascular smooth muscle subtypes provides insight into embryological origin-dependent disease susceptibility. *Nature Biotechnology* 30, 165-173 (2012).
25. Witty, A. D. et al. Generation of the epicardial lineage from human pluripotent stem cells. *Nat. Biotechnol.* 32, 1026-1035 (2014).
26. Iyer, D. et al. Robust derivation of epicardium and its differentiated smooth muscle cell progeny from human pluripotent stem cells. *Development* 142, 1528-1541 (2015).
27. Phillips, M. D., Mukhopadhyay, M., Poscablo, C. & Westphal, H. Dkk1 and Dkk2 regulate epicardial specification during mouse heart development. *Int. J. Cardiol.* 150, 186-92 (2011).
28. van Tuyn, J. et al. Epicardial cells of human adults can undergo an epithelial-to-mesenchymal transition and obtain characteristics of smooth muscle cells in vitro. *Stem Cells* 25, 271-278 (2007).
29. Hockemeyer, D. et al. Genetic engineering of human pluripotent cells using TALE nucleases. *Nat. Biotechnol.* 29, 731-4 (2011).
30. Lian, X. et al. A small molecule inhibitor of SRC family kinases promotes simple epithelial differentiation of human pluripotent stem cells. *PLoS One* 8, e60016 (2013).
31. Schmuck, E. G. et al. Cardiac fibroblast-derived 3D extracellular matrix seeded with mesenchymal stem cells as a novel device to transfer cells to the ischemic myocardium. *Cardiovasc. Eng. Technol.* 5, 119-131 (2014).
32. Kim, D., Langmead, B. & Salzberg, S. L. HISAT: a fast spliced aligner with low memory requirements. *Nat. Methods* 12, 357-360 (2015).
33. Ramsköld, D., Wang, E. T., Burge, C. B. & Sandberg, R. An abundance of ubiquitously expressed genes revealed by tissue transcriptome sequence data. *PLoS Comput. Biol.* 5, e1000598 (2009).
34. Dye, B. R. et al. In vitro generation of human pluripotent stem cell derived lung organoids. *Elife* 4, e05098 (2015).
35. Tadeu, A. M. B. et al. Transcriptional profiling of ectoderm specification to keratinocyte fate in human embryonic stem cells. *PLoS One* 10, e0122493 (2015).
36. Prasain, N. et al. Differentiation of human pluripotent stem cells to cells similar to cord-blood endothelial colony-forming cells. *Nat. Biotechnol.* 32, 1151-7 (2014).
37. Palpant, N. J. et al. Inhibition of β-catenin signaling respecifies anterior-like endothelium into beating human cardiomyocytes. *Development* 142, 3198-209 (2015).
38. Subramanian, A. et al. Gene set enrichment analysis: a knowledge-based approach for interpreting genome-wide expression profiles. *Proc. Natl. Acad. Sci. U.S.A* 102, 15545-50 (2005).
39. Lian, X. et al. Chemically defined, albumin-free human cardiomyocyte generation. *Nat. Methods* 12, 595-596 (2015).
40. Nakanishi, M. et al. Directed induction of anterior and posterior primitive streak by Wnt from embryonic stem cells cultured in a chemically defined serum-free medium. *FASEB J.* 23, 114-22 (2009).
41. Zhou, B., von Gise, A., Ma, Q., Rivera-Feliciano, J. & Pu, W. T. Nkx2-5- and Isl1-expressing cardiac progenitors contribute to proepicardium. *Biochem. Biophys. Res. Commun.* 375, 450-3 (2008).
42. Moore, A. W., McInnes, L., Kreidberg, J., Hastie, N. D. & Schedl, A. YAC complementation shows a requirement for Wt1 in the development of epicardium, adrenal gland and throughout nephrogenesis. *Development* 126, 1845-57 (1999).
43. Martínez-Estrada, O. M. et al. Wt1 is required for cardiovascular progenitor cell formation through transcriptional control of Snail and E-cadherin. *Nat. Genet.* 42, 89-93 (2010).
44. Hockemeyer, D. et al. Genetic engineering of human pluripotent cells using TALE nucleases. *Nat. Biotechnol.* 29, 731-4 (2011).
45. Kofidis, T. et al. Insulin-like growth factor promotes engraftment, differentiation, and functional improvement after transfer of embryonic stem cells for myocardial restoration. *Stem Cells* 22, 1239-45 (2004).
46. Engels, M. C. et al. Insulin-like growth factor promotes cardiac lineage induction in vitro by selective expansion of early mesoderm. *Stem Cells* 32, 1493-502 (2014).
47. Cao, N. et al. Ascorbic acid enhances the cardiac differentiation of induced pluripotent stem cells through promoting the proliferation of cardiac progenitor cells. *Cell Res.* 22, 219-36 (2012).
48. Ueno, S. et al. Biphasic role for Wnt/beta-catenin signaling in cardiac specification in zebrafish and embryonic stem cells. *Proc. Natl. Acad. Sci. U.S.A* 104, 9685-90 (2007).
49. David, R. et al. MesP1 drives vertebrate cardiovascular differentiation through Dkk-1-mediated blockade of Wnt-signalling. *Nat. Cell Biol.* 10, 338-45 (2008).
50. Ruiz-Villalba, A., Ziogas, A., Ehrbar, M. & Pérez-Pomares, J. M. Characterization of epicardial-derived cardiac interstitial cells: differentiation and mobilization of heart fibroblast progenitors. *PLoS One* 8, e53694 (2013).
51. Pérez-Pomares, J. M. et al. Experimental studies on the spatiotemporal expression of WT1 and RALDH2 in the embryonic avian heart: a model for the regulation of myocardial and valvuloseptal development by epicardially derived cells (EPDCs). *Dev. Biol.* 247, 307-26 (2002).
52. Garriock, R. J., Mikawa, T. & Yamaguchi, T. P. Isolation and culture of mouse proepicardium using serum-free conditions. *Methods* 66, 365-9 (2014).
53. Bochmann, L. et al. Revealing new mouse epicardial cell markers through transcriptomics. *PLoS One* 5, e11429 (2010).
54. Lam, J. T., Moretti, A. & Laugwitz, K.-L. Multipotent progenitor cells in regenerative cardiovascular medicine. *Pediatr. Cardiol.* 30, 690-8 (2009).
55. Winter, E. M. et al. Preservation of left ventricular function and attenuation of remodeling after transplantation of human epicardium-derived cells into the infarcted mouse heart. *Circulation* 116, 917-27 (2007).
56. Wang, J., Cao, J., Dickson, A. L. & Poss, K. D. Epicardial regeneration is guided by cardiac outflow tract and Hedgehog signalling. *Nature* 522, 226-230 (2015).
57. Xiao, Y., Liu, K., Shen, J., Xu, G. & Ye, W. SB-431542 inhibition of scar formation after filtration surgery and its potential mechanism. *Invest. Ophthalmol. Vis. Sci.* 50, 1698-706 (2009).

The present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

We claim:

1. A cell culture comprising a chemically defined, albumin-free culture medium comprising an inhibitor of TGFβ signaling and that does not comprise Bone Morphogenetic Protein 4 (BMP4), and a cell population comprising human self-renewing epicardial cells capable of proliferating in vitro for at least 25 cell divisions without differentiation, are not immortalized, and maintain the ability to undergo epithelial-to-mesenchymal transition (EMT), wherein the epicardial cells are derived from a human pluripotent stem cell line in vitro.

2. The cell culture of claim 1, wherein at least 95% of cells of the cell population are epicardial cells positive for expression of Wilms' tumor suppressor protein (WT1).

3. The cell culture of claim 1, wherein the inhibitor of TGFβ signaling is A83-01 or SB431542.

4. The cell culture of claim 1, wherein the chemically defined, albumin-free culture is substantially free of any xenogenic component with regard to the human epicardial cells.

5. The cell culture of claim 1, wherein the human pluripotent stem cell line is a human embryonic stem cell line or a human induced pluripotent stem cell line.

* * * * *

SEQUENCE LISTING

```
<160> NUMBER OF SEQ ID NOS: 40

<210> SEQ ID NO 1
<211> LENGTH: 57
<212> TYPE: DNA
<213> ORGANISM: Artificial Sequence
<220> FEATURE:
<223> OTHER INFORMATION: synthetic

<400> SEQUENCE: 1
ccggaggtgc tatctgtctg ctctactcga gtagagcaga cagatagcac ctttttt        57

<210> SEQ ID NO 2
<211> LENGTH: 57
<212> TYPE: DNA
<213> ORGANISM: Artificial Sequence
<220> FEATURE:
<223> OTHER INFORMATION: synthetic

<400> SEQUENCE: 2
ccgggcttgg aatgagactg ctgatctcga gatcagcagt ctcattccaa gctttttt        57

<210> SEQ ID NO 3
<211> LENGTH: 23
<212> TYPE: DNA
<213> ORGANISM: Artificial Sequence
<220> FEATURE:
<223> OTHER INFORMATION: synthetic

<400> SEQUENCE: 3
```

-continued

```
aactccagct ggcgctttga ggg                                              23

<210> SEQ ID NO 4
<211> LENGTH: 23
<212> TYPE: DNA
<213> ORGANISM: Artificial Sequence
<220> FEATURE:
<223> OTHER INFORMATION: synthetic

<400> SEQUENCE: 4
ggacactgaa cggtccccga ggg                                              23

<210> SEQ ID NO 5
<211> LENGTH: 19
<212> TYPE: DNA
<213> ORGANISM: Artificial Sequence
<220> FEATURE:
<223> OTHER INFORMATION: synthetic

<400> SEQUENCE: 5
cagtgcccga aacccacac                                                   19

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
ggagacccag cagcctcaaa                                                  20

<210> SEQ ID NO 7
<211> LENGTH: 23
<212> TYPE: DNA
<213> ORGANISM: Artificial Sequence
<220> FEATURE:
<223> OTHER INFORMATION: synthetic

<400> SEQUENCE: 7
cgaagaatag caatggtgtg acg                                              23

<210> SEQ ID NO 8
<211> LENGTH: 21
<212> TYPE: DNA
<213> ORGANISM: Artificial Sequence
<220> FEATURE:
<223> OTHER INFORMATION: synthetic

<400> SEQUENCE: 8
ttccaaagca gcctccaagt c                                                21

<210> SEQ ID NO 9
<211> LENGTH: 20
<212> TYPE: DNA
<213> ORGANISM: Artificial Sequence
<220> FEATURE:
<223> OTHER INFORMATION: synthetic

<400> SEQUENCE: 9
aagaaggaaa tgcagcctca                                                  20

<210> SEQ ID NO 10
<211> LENGTH: 20
<212> TYPE: DNA
```

```
<213> ORGANISM: Artificial Sequence
<220> FEATURE:
<223> OTHER INFORMATION: synthetic

<400> SEQUENCE: 10
tactgcaggt gtgagcaagg                                                    20

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cacaagcgtc tcgggatt                                                      18

<210> SEQ ID NO 12
<211> LENGTH: 19
<212> TYPE: DNA
<213> ORGANISM: Artificial Sequence
<220> FEATURE:
<223> OTHER INFORMATION: synthetic

<400> SEQUENCE: 12
agtggcaagt cttccgaca                                                     19

<210> SEQ ID NO 13
<211> LENGTH: 20
<212> TYPE: DNA
<213> ORGANISM: Artificial Sequence
<220> FEATURE:
<223> OTHER INFORMATION: synthetic

<400> SEQUENCE: 13
gtgaccaaca tggagtcgtg                                                    20

<210> SEQ ID NO 14
<211> LENGTH: 20
<212> TYPE: DNA
<213> ORGANISM: Artificial Sequence
<220> FEATURE:
<223> OTHER INFORMATION: synthetic

<400> SEQUENCE: 14
tgcttcacag aagaccatgc                                                    20

<210> SEQ ID NO 15
<211> LENGTH: 24
<212> TYPE: DNA
<213> ORGANISM: Artificial Sequence
<220> FEATURE:
<223> OTHER INFORMATION: synthetic

<400> SEQUENCE: 15
gcgattatgc agcgtgcaat gagt                                               24

<210> SEQ ID NO 16
<211> LENGTH: 24
<212> TYPE: DNA
<213> ORGANISM: Artificial Sequence
<220> FEATURE:
<223> OTHER INFORMATION: synthetic

<400> SEQUENCE: 16
aacataaata cgggtgggtg cgtg                                               24
```

<210> SEQ ID NO 17
<211> LENGTH: 24
<212> TYPE: DNA
<213> ORGANISM: Artificial Sequence
<220> FEATURE:
<223> OTHER INFORMATION: synthetic

<400> SEQUENCE: 17
ttcaccaaag atctgctcct cgct                                          24

<210> SEQ ID NO 18
<211> LENGTH: 26
<212> TYPE: DNA
<213> ORGANISM: Artificial Sequence
<220> FEATURE:
<223> OTHER INFORMATION: synthetic

<400> SEQUENCE: 18
ttattactgg tgtggagtgg gtgtgg                                        26

<210> SEQ ID NO 19
<211> LENGTH: 20
<212> TYPE: DNA
<213> ORGANISM: Artificial Sequence
<220> FEATURE:
<223> OTHER INFORMATION: synthetic

<400> SEQUENCE: 19
cccaggactc cctcctatgt                                               20

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
taggaaccct gatgggtctg                                               20

<210> SEQ ID NO 21
<211> LENGTH: 20
<212> TYPE: DNA
<213> ORGANISM: Artificial Sequence
<220> FEATURE:
<223> OTHER INFORMATION: synthetic

<400> SEQUENCE: 21
cagcttgaat gcatgacctg                                               20

<210> SEQ ID NO 22
<211> LENGTH: 20
<212> TYPE: DNA
<213> ORGANISM: Artificial Sequence
<220> FEATURE:
<223> OTHER INFORMATION: synthetic

<400> SEQUENCE: 22
gatgccgacc gtacaagagt                                               20

<210> SEQ ID NO 23
<211> LENGTH: 20
<212> TYPE: DNA
<213> ORGANISM: Artificial Sequence
<220> FEATURE:

<223> OTHER INFORMATION: synthetic

<400> SEQUENCE: 23
accctcttcc tcgctttctc                                                    20

<210> SEQ ID NO 24
<211> LENGTH: 20
<212> TYPE: DNA
<213> ORGANISM: Artificial Sequence
<220> FEATURE:
<223> OTHER INFORMATION: synthetic

<400> SEQUENCE: 24
tgctctcgtt ggaagtcaca                                                    20

<210> SEQ ID NO 25
<211> LENGTH: 20
<212> TYPE: DNA
<213> ORGANISM: Artificial Sequence
<220> FEATURE:
<223> OTHER INFORMATION: synthetic

<400> SEQUENCE: 25
ctcctctgtc acaccccatt                                                    20

<210> SEQ ID NO 26
<211> LENGTH: 20
<212> TYPE: DNA
<213> ORGANISM: Artificial Sequence
<220> FEATURE:
<223> OTHER INFORMATION: synthetic

<400> SEQUENCE: 26
ttgacagctg gaaagatgga                                                    20

<210> SEQ ID NO 27
<211> LENGTH: 20
<212> TYPE: DNA
<213> ORGANISM: Artificial Sequence
<220> FEATURE:
<223> OTHER INFORMATION: synthetic

<400> SEQUENCE: 27
acagagcatt tgcagacagg                                                    20

<210> SEQ ID NO 28
<211> LENGTH: 20
<212> TYPE: DNA
<213> ORGANISM: Artificial Sequence
<220> FEATURE:
<223> OTHER INFORMATION: synthetic

<400> SEQUENCE: 28
gtgctacaca gcagccagat                                                    20

<210> SEQ ID NO 29
<211> LENGTH: 20
<212> TYPE: DNA
<213> ORGANISM: Artificial Sequence
<220> FEATURE:
<223> OTHER INFORMATION: synthetic

<400> SEQUENCE: 29
ttctgctgct cttgctgttt                                                    20

```
<210> SEQ ID NO 30
<211> LENGTH: 20
<212> TYPE: DNA
<213> ORGANISM: Artificial Sequence
<220> FEATURE:
<223> OTHER INFORMATION: synthetic

<400> SEQUENCE: 30
tggctcaagt caaagtcctg                                               20

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
ctccaatcaa cttgccagaa                                               20

<210> SEQ ID NO 32
<211> LENGTH: 20
<212> TYPE: DNA
<213> ORGANISM: Artificial Sequence
<220> FEATURE:
<223> OTHER INFORMATION: synthetic

<400> SEQUENCE: 32
ataccagttg gaggctggtc                                               20

<210> SEQ ID NO 33
<211> LENGTH: 23
<212> TYPE: DNA
<213> ORGANISM: Artificial Sequence
<220> FEATURE:
<223> OTHER INFORMATION: synthetic

<400> SEQUENCE: 33
gaatgagact gctgatcttg gac                                           23

<210> SEQ ID NO 34
<211> LENGTH: 23
<212> TYPE: DNA
<213> ORGANISM: Artificial Sequence
<220> FEATURE:
<223> OTHER INFORMATION: synthetic

<400> SEQUENCE: 34
gaatgagact gctgatcttg gac                                           23

<210> SEQ ID NO 35
<211> LENGTH: 20
<212> TYPE: DNA
<213> ORGANISM: Artificial Sequence
<220> FEATURE:
<223> OTHER INFORMATION: synthetic

<400> SEQUENCE: 35
gtggacctga cctgccgtct                                               20

<210> SEQ ID NO 36
<211> LENGTH: 20
<212> TYPE: DNA
<213> ORGANISM: Artificial Sequence
<220> FEATURE:
<223> OTHER INFORMATION: synthetic
```

```
<400> SEQUENCE: 36
ggaggagtgg gtgtcgctgt                                              20

<210> SEQ ID NO 37
<211> LENGTH: 20
<212> TYPE: DNA
<213> ORGANISM: Artificial Sequence
<220> FEATURE:
<223> OTHER INFORMATION: synthetic

<400> SEQUENCE: 37
ggtcttggtt tctgctggac                                              20

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
aagtcgtgct gcttcatgtg                                              20

<210> SEQ ID NO 39
<211> LENGTH: 20
<212> TYPE: DNA
<213> ORGANISM: Artificial Sequence
<220> FEATURE:
<223> OTHER INFORMATION: synthetic

<400> SEQUENCE: 39
tgaaaagccc ttcagctgtc                                              20

<210> SEQ ID NO 40
<211> LENGTH: 21
<212> TYPE: DNA
<213> ORGANISM: Artificial Sequence
<220> FEATURE:
<223> OTHER INFORMATION: synthetic

<400> SEQUENCE: 40
tgaggaggag tggagagtca g                                            21
```